(12) United States Patent
Starke et al.

(10) Patent No.: US 7,470,678 B2
(45) Date of Patent: Dec. 30, 2008

(54) DIPHENYLAZETIDINONE DERIVATIVES FOR TREATING DISORDERS OF THE LIPID METABOLISM

(75) Inventors: Ingemar Starke, Molndal (SE); Mikael Ulf Johan Dahlstrom, Mölndal (SE); Ann-Margret Lindqvist, Mölndal (SE); Mats Peter Nordberg, Mölndal (SE); Tore Skjaret, Mölndal (SE); Malin Anita Lemurell, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 420 days.

(21) Appl. No.: 10/519,897

(22) PCT Filed: Jul. 1, 2003

(86) PCT No.: PCT/GB03/02811

§ 371 (c)(1), (2), (4) Date: Dec. 31, 2004

(87) PCT Pub. No.: WO2004/005247

PCT Pub. Date: Jan. 15, 2004

(65) Prior Publication Data

US 2005/0239766 A1 Oct. 27, 2005

(30) Foreign Application Priority Data

Jul. 5, 2002 (GB) ................... 0215579.4

(51) Int. Cl.
  C07D 205/08 (2006.01)
  A61K 31/397 (2006.01)
  A61P 3/06 (2006.01)
  A61P 9/10 (2006.01)
  A61P 7/02 (2006.01)

(52) U.S. Cl. .................. 514/210.09; 540/200
(58) Field of Classification Search .......... 540/200; 514/210, 210.02
See application file for complete search history.

(56) References Cited

U.S. PATENT DOCUMENTS

| | | | |
|---|---|---|---|
| 5,306,817 A | 4/1994 | Thiruvengadam et al. | |
| 5,631,365 A | 5/1997 | Rosenblum et al. | |
| 5,633,246 A | 5/1997 | McKittrick et al. | |
| 5,661,145 A | 8/1997 | Davis | |
| 5,739,321 A | 4/1998 | Wu et al. | |
| 5,744,467 A | 4/1998 | McKittrick et al. | |
| 5,756,470 A | 5/1998 | Yumibe et al. | |
| 5,767,115 A | 6/1998 | Rosenblum et al. | |
| 5,846,966 A | 12/1998 | Rosenblum et al. | |
| 5,886,171 A | 3/1999 | Wu et al. | |
| 5,919,672 A | 7/1999 | Homann et al. | |
| RE37,721 E | 5/2002 | Rosenblum et al. | |
| 7,235,543 B2 * | 6/2007 | Burnett et al. ......... | 514/210.02 |
| 2002/0137690 A1 | 9/2002 | Ghosal et al. | |
| 2003/0119428 A1 | 6/2003 | Davis et al. | |
| 2003/0119757 A1 | 6/2003 | Davis | |
| 2004/0018060 A1 | 6/2003 | Kaezek et al. | |
| 2004/0018061 A1 | 1/2004 | Jansson | |
| 2004/0254369 A1 | 12/2004 | Patel | |
| 2005/0096307 A1 | 5/2005 | Graziano | |
| 2005/0267049 A1 | 12/2005 | Goulet et al. | |
| 2006/0046996 A1 | 3/2006 | Aoki et al. | |
| 2006/0069080 A1 | 3/2006 | Veltri | |
| 2007/0049748 A1 | 3/2007 | Uppala et al. | |
| 2007/0078098 A1 | 4/2007 | DEVita et al. | |
| 2007/0129540 A1 | 6/2007 | Framroze et al. | |
| 2007/0142304 A1 * | 6/2007 | Alenfalk et al. ............... | 514/19 |
| 2007/0155674 A1 * | 7/2007 | Burnett et al. ................. | 514/23 |
| 2007/0155675 A1 * | 7/2007 | Burnett et al. ................. | 514/23 |
| 2008/0064676 A1 * | 3/2008 | Alenfalk et al. ......... | 514/210.02 |

FOREIGN PATENT DOCUMENTS

| | | |
|---|---|---|
| EP | 524595 | 1/1993 |
| EP | 1413331 | 9/2001 |
| EP | 0792264 | 2/2002 |
| EP | 1362855 | 11/2003 |
| WO | 9302048 | 2/1993 |
| WO | 9414433 | 7/1994 |
| WO | 9417038 | 8/1994 |
| WO | 95/01961 | 1/1995 |
| WO | 9508532 | 3/1995 |
| WO | 9526334 | 10/1995 |
| WO | 9535277 | 12/1995 |
| WO | 9609827 | 4/1996 |
| WO | 9616037 | 5/1996 |

(Continued)

OTHER PUBLICATIONS

Clader et al., "2-Azetidinone Cholesterol Absorption Inhibitors: Structure-Activity Relationships on the Heterocyclic Nucleus," J. Med Chem (1996) 39:3684-3693.

(Continued)

*Primary Examiner*—Mark L Berch
(74) *Attorney, Agent, or Firm*—Pepper Hamilton LLP

(57) ABSTRACT

Compounds of formula (I): (wherein variable groups are as defined within) pharmaceutically acceptable salts, solvates, solvates of such salts and prodrugs thereof and their use as cholesterol absorption inhibitors for the treatment of hyperlipidaemia are described. Processes for their manufacture and pharmaceutical compositions containing them are also described

37 Claims, No Drawings

FOREIGN PATENT DOCUMENTS

| | | |
|---|---|---|
| WO | 9619450 | 6/1996 |
| WO | 9716424 | 5/1997 |
| WO | 9716455 | 5/1997 |
| WO | 9745406 | 12/1997 |
| WO | 0020623 | 4/2000 |
| WO | 0034240 | 6/2000 |
| WO | 0038725 | 7/2000 |
| WO | 0060107 | 10/2000 |
| WO | 0063703 | 10/2000 |
| WO | 0218432 | 3/2002 |
| WO | 0250027 | 6/2002 |
| WO | 0250060 | 6/2002 |
| WO | 0250068 | 6/2002 |
| WO | 0250090 | 6/2002 |
| WO | 02058685 | 8/2002 |
| WO | 02058696 | 8/2002 |
| WO | 02058732 | 8/2002 |
| WO | 02058733 | 8/2002 |
| WO | 02066464 | 8/2002 |
| WO | 020508734 | 8/2002 |
| WO | 02072104 | 9/2002 |
| WO | 02079174 | 10/2002 |
| WO | 02096415 | 12/2002 |
| WO | 03026643 | 4/2003 |
| WO | 03026644 | 4/2003 |
| WO | 03088962 | 10/2003 |
| WO | 2004000803 | 12/2003 |
| WO | 2004000804 | 12/2003 |
| WO | 2004000805 | 12/2003 |
| WO | 2004005247 | 1/2004 |
| WO | 2004010948 | 2/2004 |
| WO | 2004010993 | 2/2004 |
| WO | 2004014947 | 2/2004 |
| WO | 0403457 | 5/2004 |
| WO | 04043456 | 5/2004 |
| WO | 2004081002 | 9/2004 |
| WO | 04099132 | 11/2004 |
| WO | 04107958 | 12/2004 |
| WO | 05000353 | 1/2005 |
| WO | 2005021495 | 3/2005 |
| WO | WO 2005021497 A2 * | 3/2005 |
| WO | 2005033100 | 4/2005 |
| WO | 05042692 | 5/2005 |
| WO | 2005044256 | 5/2005 |
| WO | 2005047248 | 5/2005 |
| WO | 2005049592 | 6/2005 |
| WO | 2005058316 | 6/2005 |
| WO | 2005061451 | 7/2005 |
| WO | 2005061452 | 7/2005 |
| WO | 2005062824 | 7/2005 |
| WO | 2005062897 | 7/2005 |
| WO | 2005066120 | 7/2005 |
| WO | 2005067903 | 7/2005 |
| WO | 2005069900 | 8/2005 |
| WO | 2005113495 | 12/2005 |
| WO | 2005113496 | 12/2005 |
| WO | 2006017257 | 2/2006 |
| WO | 2006060808 | 6/2006 |
| WO | 2006068990 | 6/2006 |
| WO | 2006072957 | 7/2006 |
| WO | 2006086562 | 8/2006 |
| WO | 2006102674 | 9/2006 |
| WO | 2006107936 | 10/2006 |
| WO | 2006116499 | 11/2006 |
| WO | 2006121861 | 11/2006 |
| WO | 2006122186 | 11/2006 |
| WO | 2006122216 | 11/2006 |
| WO | 2006124713 | 11/2006 |
| WO | 2006127893 | 11/2006 |
| WO | 2006134604 | 12/2006 |
| WO | 2006137080 | 12/2006 |
| WO | 2006137782 | 12/2006 |
| WO | 2006137792 | 12/2006 |
| WO | 2006137793 | 12/2006 |
| WO | 2006137794 | 12/2006 |
| WO | 2006137795 | 12/2006 |
| WO | 2006137796 | 12/2006 |
| WO | 2006137797 | 12/2006 |
| WO | 2006138163 | 12/2006 |
| WO | 2007003365 | 1/2007 |
| WO | 2007008529 | 1/2007 |
| WO | 2007008541 | 1/2007 |
| WO | 2007015161 | 2/2007 |
| WO | 2007016643 | 2/2007 |
| WO | 2007017705 | 2/2007 |
| WO | 2007030721 | 3/2007 |
| WO | 2007058335 | 5/2007 |
| WO | 2007059871 | 5/2007 |
| WO | 2007072088 | 6/2007 |
| WO | 2007075702 | 7/2007 |
| WO | 02058731 | 8/2008 |

OTHER PUBLICATIONS

McKittrick et al., Stereoselective synthesis and biological activity of cis azetidinones as cholesterol absorption inhibitors, Bioorganic & Medicinal Chemistry Letters (1996) 6(16):1947-1950.

Burnett et al., "2-Azetidinones as Inhibitors of Cholesterol Absorption," J. Med Chem (1994) 12:1733-1736.

Castaner et al., "Ezetimibe," Drugs of the Future (2000) 25(7):679-685.

Vaccaro et al., "Sugar-substituted 2-azetidinone cholesterol absorption inhibitors: Enhanced potency by modification of the sugar," Bioorganic & Medicinal Chemistry Letters (1998) 8:313-318.

Fu et al., "Process for preparing Ezetimibe intermediate by an acid enhanced chemo- and enantioselective CBS catalyzed ketone reduction," Tetrahedron Letters (2003) 44:801-804.

Kirkup et al., "(—)-SCH 57939: synthesis and pharmacological properties of a potent, metabolically stable cholesterol absorption inhibitor," Bioorganic & Medicinal Chemistry Letters (1996) 6(17):2069-2072.

Vaccaro et al., "Carboxy-substituted 2-azetidinones as cholesterol absorption inhibitors," Bioorganic & Medicinal Chemistry Letters (1998) 8:319-322.

Rosenblum et al., "Discovery of 1-(4-fluorophenyl)-(3R)-[3-(4-fluorophenyl)-(3S)-hydroxypropyl]-(4S)-(4 - hydroxyphenyl)-2-azetidinone (SCH 58235): a designed, potent, orally active inhibitor of cholesterol absorption.," J. Med Chem (1998) 41:973-980.

Wu et al., "A Novel One-Step Diastereo- and Enantioselective Formation of trans-Azetidinones and Its Application to the Total Synthesis of Cholesterol Absorption Inhibitors," J. Org. Chem (1999) 64:3714-3718.

McKittrick et al., "Synthesis of C3 heteroatom-substituted azetidinones that display potent cholesterol absorption inhibitory activity," J. Med. Chem. (1998) 41(5):752-759.

Kvaerno et al., "Synthesis and in vitro evaluation of inhibitors of intestinal cholesterol absorption," J Med Chem (2005) 48(19):6035-6053.

Burnett "Beta-lactam cholesterol absorption inhibitors," Curr Med Chem (2004) 11:1873-1887.

Seedorf et al., "Cholesterol absorption inhibitor ezetimibe blocks uptake of oxidized LDL in human macrophages," Biochem Biophys Research Commun (2004) 320(4):1337-1341.

Kvaerno et al., "An in vitro assay for evaluation of small-molecule inhibitors of cholesterol absorption," (2004) 43 (35):4653-4656.

Clader "Ezetimibe and other azetidinone cholesterol absorption inhibitors of cholesterol absorption," Curr Topics in Med Chem (2005) 5 (3):243-256.

Carcia-Calvo et al., "The target of ezetimibe is Niemann-Pick C1-Like 1 (NPC1L1)," PNAS (2005) 102(23):8132-8137.

Ritter et al., "Heterocyclic ring scaffolds as small-molecule cholesterol absorption inhibitors," Org Biomol Chem (2005) 3:3514-3523.

Dugar et al., "Gamma-lactams and related compounds as cholesterol absorption inhibitors: homologs of the beta-lactam cholesterol absorption inhibitor SCH 48461," Bioorganic & Medicinal Letters (1995) 5(24):2947-2952.

Mounsey et al., "Diet may slow progression of diabetic nephropathy," The Journal of Family Practice (2003) 52 (9):672-673.

Sobieszczyk et al., "Acute pulmonary embolism: don't ignore the platelet," Circulation (2002) 106(14):1748-1749.

Journal of the American College of Cardiology (2000) 35(1):252A.

van Heek et al., "Comparison of the activity and disposition of the novel cholesterol absorption inhibitor, SCH58235, and its glucuronide, SCH60663," Br. J. Pharmcol (2000) 129(8):1748-1754.

Yang et al., "Allelic Variants in Long-QT Disease Genes in Patients With Drug-Associated Torsades de Pointes," Circulation (2002) 105(16):1943-1948.

Zaks et al., Enzymatic glucuronidation of a novel cholesterol absorption inhibitor, Sch 58235, Appl Biochem Biotechnol. (1998) 73(2-3):205-214.

Clader "The discovery of ezetimibe: a view from outside the receptor," J Med Chem (2004) 47(1):1-9.

Altmann et al., "Niemann-pick C1 like 1 protein is critical for intestinal cholesterol absorption," Science (2004) 303:1201-1204.

* cited by examiner

DIPHENYLAZETIDINONE DERIVATIVES FOR TREATING DISORDERS OF THE LIPID METABOLISM

RELATED APPLICATIONS

This application is a national stage filing under 35 U.S.C. 371 of International Application PCT/GB2003/002811, filed Jul. 1, 2003, which claims priority from United Kingdom Application No. 0215579.4, filed Jul. 5, 2002 the specifications of each of which are incorporated by reference herein. International Application PCT/GB2003/002811 was published under PCT Article 21(2) in English.

This invention relates to 2-azetidinone derivatives, or pharmaceutically acceptable salts, solvates, solvates of such salts and prodrugs thereof. These 2-azetidinones possess cholesterol absorption inhibitory activity and are accordingly of value in the treatment of disease states associated with hyperlipidaemic conditions. They are therefore useful in methods of treatment of a warm-blooded animal, such as man. The invention also relates to processes for the manufacture of said 2-azetidinone derivatives, to pharmaceutical compositions containing them and to their use in the manufacture of medicaments to inhibit cholesterol absorption in a warm-blooded animal, such as man. A further aspect of this invention relates to the use of the compounds of the invention in the treatment of dyslipidemic conditions.

Atherosclerotic coronary artery disease is a major cause of death and morbidity in the western world as well as a significant drain on healthcare resources. It is well-known that hyperlipidaemic conditions associated with elevated concentrations of total cholesterol and low density lipoprotein (LDL) cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46).

The concentration of plasma cholesterol depends on the integrated balance of endogenous and exogenous pathways of cholesterol metabolism. In the endogenous pathway, cholesterol is synthesized by the liver and extra hepatic tissues and enters the circulation as lipoproteins or is secreted into bile. In the exogenous pathway cholesterol from dietary and biliary sources is absorbed in the intestine and enters the circulation as component of chylomicrons. Alteration of either pathway will affect the plasma concentration of cholesterol.

The precise mechanism by which cholesterol is absorbed from the intestine is however not clear. The original hypothesis has been that cholesterol is crossing the intestine by unspecific diffusion. But more recent studies are suggesting that there are specific transporters involved in the intestinal cholesterol absorption. (See for instance New molecular targets for cholesterol-lowering therapy Izzat, N. N., Deshazer, M. E. and Loose-Mitchell D. S. JPET 293:315-320, 2000.)

A clear association between reduction of total cholesterol and (LDL) cholesterol and decreased instance of coronary artery disease has been established, and several classes of pharmaceutical agents are used to control serum cholesterol. There major options to regulate plasma cholesterol include (i) blocking the synthesis of cholesterol by agents such as HMG-CoA reductase inhibitors, for example statins such as simvastatin and fluvastatin, which also by up-regulation of LDL-receptors will promote the cholesterol removal from the plasma; (ii) blocking the bile acid reabsorption by specific agents resulting in increased bile acid excretion and synthesis of bile acids from cholesterol with agents such as bile acid binders, such as resins e.g. cholestyramine and cholestipol; and (iii) by blocking the intestinal uptake of cholesterol by selective cholesterol absorption inhibitors. High density lipoprotein (HDL) elevating agents such as fibrates and nicotinic acid analogues have also been employed.

Even with the current diverse range of therapeutic agents, a significant proportion of the hypercholesterolaemic population is unable to reach target cholesterol levels, or drug interactions or drug safety preclude the long term use needed to reach the target levels. Therefore there is still a need to develop additional agents that are more efficacious and are better tolerated.

Compounds possessing such cholesterol absorption inhibitory activity have been described, see for instance the compounds described in WO 93/02048, WO 94/17038, WO 95/08532, WO 95/26334, WO 95/35277, WO 96/16037, WO 96/19450, WO 97/16455, WO 02/50027, WO 02/50060, WO 02/50068, WO 02/50090, WO 02/66464, U.S. Pat. No. 5,756,470, U.S. Pat. No. 5,767,115 and US RE37721.

The present invention is based on the discovery that certain benzothiazepine and benzothiadiazepine compounds surprisingly inhibit cholesterol absorption. Such properties are expected to be of value in the treatment of disease states associated with hyperlipidaemic conditions. The compounds of the present invention are not disclosed in any of the above applications and we have surprisingly found that these compound possess beneficial efficacious, metabolic and toxicological profiles that make them particularly suitable for in vivo administration to a warm blooded animal, such as man. In particular certain compounds of the present invention have a low degree of absorption compared to the compounds of the prior art whilst retaining their ability to inhibit cholesterol absorption.

Accordingly there is provided a compound of formula (I):

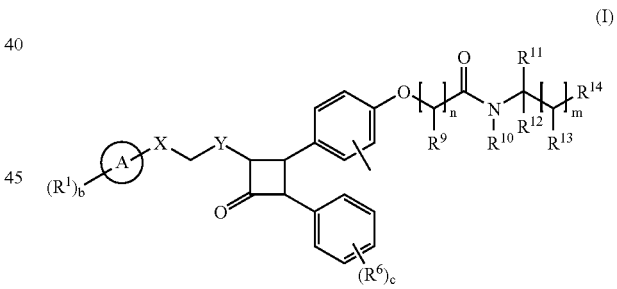

wherein:

Ring A is selected from phenyl or thienyl;

X is selected from —$CR^2R^3$—, —O—, —$NR^x$— and —$S(O)_a$—; wherein $R^x$ is hydrogen or $C_{1-6}$alkyl, and a is 0-2;

Y is selected from —$CR^4R^5$—, —O—, —$NR^z$— and —$S(O)_a$—; wherein $R^z$ is hydrogen or $C_{1-6}$alkyl, and a is 0-2; wherein there is at least one —$CR^2R^3$— or —$CR^4R^5$— group;

$R^1$ is independently selected from halo, hydroxy, $C_{1-6}$alkyl, $C_{1-6}$alkoxy and $C_{1-6}$-alkylS(O)$_a$ wherein a is 0 to 2; wherein $R^1$ is independently optionally substituted on carbon by one or more halo, $C_{1-6}$alkoxy and hydroxy;

b is 0-3; wherein the values of $R^1$ may be the same or different;

$R^2$ and $R^3$ are independently selected from hydrogen, hydroxy, $C_{1-6}$alkyl, $C_{1-6}$alkoxy and $C_{1-6}$alkanoyloxy;

wherein $R^2$ and $R^3$ may be independently optionally substituted on carbon by one or more halo or hydroxy; or $R^2$ and $R^3$ together form an oxo group;

$R^4$ and $R^5$ are independently selected from hydrogen, hydroxy, $C_{1-6}$alkyl, $C_{1-6}$alkoxy and $C_{1-6}$alkanoyloxy; or $R^4$ and $R^5$ together form an oxo group;

$R^6$ is independently selected from halo, nitro, cyano, hydroxy, amino, carboxy, formyl, carbamoyl, carbamoyloxy, mercapto, sulphamoyl, $C_{1-6}$alkyl, $C_{2-6}$alkenyl, $C_{2-6}$alkenyloxy, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, $C_{1-6}$-alkanoyl-N-($C_{1-6}$alkyl)amino, $C_{1-6}$alkylsulphonylamino, $C_{1-6}$alkylsulphonyl-N-($C_{1-6}$alkyl)amino, N-($C_{1-6}$alkyl)carbamoyl, N,N-($C_{1-6}$alkyl)$_2$carbamoyl, N-($C_{1-6}$alkyl)carbamoyloxy, N,N-($C_{1-6}$alkyl)$_2$carbamoyloxy, $C_{1-6}$alkylS(O)$_a$ wherein a is 0 to 2, $C_{1-6}$alkoxycarbonyl, $C_{1-6}$alkoxycarbonylamino, $C_{1-6}$alkoxycarbonyl-N-($C_{1-6}$alkyl)amino, $C_{1-6}$alkoxycarbonyloxy, $C_{1-6}$alkoxycarbonylamino, ureido, N'-($C_{1-6}$alkyl)ureido, N-($C_{1-6}$alkyl)ureido, N',N'-($C_{1-6}$alkyl)$_2$ureido, N'-($C_{1-6}$alkyl)-N-($C_{1-6}$alkyl)ureido, N',N'-($C_{1-6}$alkyl)$_2$-N-($C_{1-6}$alkyl)ureido, N-($C_{1-6}$alkyl)sulphamoyl, N,N-($C_{1-6}$alkyl)$_2$sulphamoyl and phenyl; wherein $R^7$ is independently optionally substituted on carbon by one or more halo, $C_{1-6}$alkoxy, hydroxy, amino, carboxy, $C_{1-6}$alkoxycarbonyl, carbamoyl, N-($C_{1-6}$alkyl)carbamoyl, N,N-($C_{1-6}$alkyl)$_2$carbamoyl, $C_{1-6}$alkanoylamino, $C_{1-6}$alkanoyl-N-($C_{1-6}$alkyl)amino, phenyl, phenoxy, benzoyl, phenyl$C_{1-6}$alkyl and phenyl$C_{1-6}$alkoxy;

c is 0-5; wherein the values of $R^6$ may be the same or different;

$R^7$ is independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

d is 0-4; wherein the values of $R^7$ may be the same or different;

$R^9$ is hydrogen, $C_{1-4}$alkyl, carbocyclyl or heterocyclyl; wherein $R^9$ may be optionally substituted on carbon by one or more substituents selected from $R^{23}$; and wherein if said heterocyclyl contains an —NH— group, that nitrogen may be optionally substituted by a group selected from $R^{24}$;

$R^{10}$ is hydrogen or $C_{1-4}$alkyl;

$R^{11}$ and $R^{12}$ are independently selected from hydrogen, $C_{1-4}$alkyl, carbocyclyl or heterocyclyl; or $R^{11}$ and $R^{12}$ together form $C_{2-6}$alkylene; wherein $R^{11}$ and $R^{12}$ or $R^{11}$ and $R^{12}$ together may be independently optionally substituted on carbon by one or more substituents selected from $R^{25}$; and wherein if said heterocyclyl contains an —NH— moiety, that nitrogen may be optionally substituted by one or more $R^{26}$;

$R^{13}$ is hydrogen, $C_{1-4}$alkyl, carbocyclyl or heterocyclyl; wherein $R^{13}$ may be optionally substituted on carbon by one or more substituents selected from $R^{27}$; and wherein if said heterocyclyl contains an —NH— moiety, that nitrogen may be optionally substituted by one or more $R^{28}$;

$R^{14}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_e$-$R^{29}$—($C_{1-10}$alkylene)$_f$-, heterocyclyl-($C_{1-10}$alkylene)$_g$-$R^{30}$—($C_{1-10}$alkylene)$_h$-, carboxy, sulpho, sulphino, phosphono, —P(O)(OR$^{31}$)(OR$^{32}$), —P(O)(OH)(OR$^{31}$), —P(O)(OH)(R$^{31}$) or —P(O)(OR$^{31}$)(R$^{32}$) wherein $R^{31}$ and $R^{32}$ are independently selected from $C_{1-6}$alkyl; wherein $R^{14}$ may be optionally substituted on carbon by one or more substituents selected from $R^{33}$; and wherein if said heterocyclyl contains an —NH— group, that nitrogen may be optionally substituted by a group selected from $R^{34}$; or $R^{14}$ is a group of formula (IA):

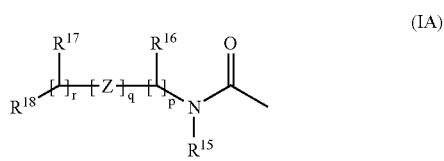

(IA)

wherein:

Z is —N(R$^{35}$)—, —N(R$^{35}$)C(O)—, —O—, and —S(O)$_a$—; wherein a is 0-2 and $R^{35}$ is hydrogen or $C_{1-4}$alkyl;

$R^{15}$ is hydrogen or $C_{1-4}$alkyl;

$R^{16}$ and $R^{17}$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl, heterocyclyl, sulpho, sulphino, amidino, phosphono, —P(O)(OR$^{36}$)(OR$^{37}$), —P(O)(OH)(OR$^{36}$), —P(O)(OH)(R$^{36}$) or —P(O)(OR$^{36}$)(R$^{37}$), wherein $R^{36}$ and $R^{37}$ are independently selected from $C_{1-6}$alkyl; wherein $R^{16}$ and $R^{17}$ may be independently optionally substituted on carbon by one or more substituents selected from $R^{38}$; and wherein if said heterocyclyl contains an —NH— group, that nitrogen may be optionally substituted by a group selected from $R^{39}$;

$R^{18}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, $C_{1-10}$alkoxycarbonyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$ sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_e$-$R^{40}$—($C_{1-10}$alkylene)$_f$- or heterocyclyl-($C_{1-10}$alkylene)$_g$-$R^{41}$—($C_{1-10}$alkylene)$_h$-, carboxy, sulpho, sulphino, phosphono, —P(O)(OR$^{42}$)(OR$^{43}$), —P(O)(OH)(OR$^{42}$), —P(O)(OH)R$^{42}$) or —P(O)(OR$^{42}$)(R$^{43}$) wherein $R^{42}$ and $R^{43}$ are independently selected from $C_{1-6}$alkyl; wherein $R^{18}$ may be optionally substituted on carbon by one or more substituents selected from $R^{44}$; and wherein if said heterocyclyl contains an —NH— group, that nitrogen may be optionally substituted by a group selected from $R^{45}$; or $R^{18}$ is a group of formula (IB):

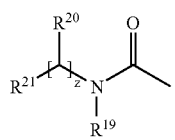

wherein:

$R^{19}$ is selected from hydrogen or $C_{1-4}$alkyl;

$R^{20}$ is selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl, heterocyclyl, sulpho, sulphino, amidino, phosphono, —P(O)(OR$^{46}$)(OR$^{47}$), —P(O)(OH)(OR$^{46}$), —P(O)(OH)(R$^{46}$) or —P(O)(OR$^{46}$)(R$^{47}$), wherein $R^{46}$ and $R^{47}$ are independently selected from $C_{1-6}$alkyl; where $R^{20}$ may be independently optionally substituted on carbon by one or more substituents selected from $R^{48}$; and wherein if said heterocyclyl contains an —NH— group, that nitrogen may be optionally substituted by a group selected from $R^{49}$;

$R^2$ is selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_e$-R$^{50}$—($C_{1-10}$alkylene)$_f$-, heterocyclyl-($C_{1-10}$alkylene)$_g$-R$^{51}$-($C_{1-10}$alkylene)$_h$-, carboxy, sulpho, sulphino, phosphono, —P(O)(OR$^{52}$)(OR$^{53}$), —P(O)(OH)(OR$^{52}$), —P(O)(OH)(R$^{52}$) or —P(O)(OR$^{53}$)(R$^{53}$) wherein $R^{52}$ and $R^{53}$ are independently selected from $C_{1-6}$alkyl; wherein $R^{21}$ may be independently optionally substituted on carbon by one or more $R^{54}$; and wherein if said heterocyclyl contains an —NH— group, that nitrogen may be optionally substituted by a group selected from $R^{55}$;

p is 1-3; wherein the values of $R^6$ may be the same or different;

q is 0-1;

r is 0-3; wherein the values of $R^{17}$ may be the same or different;

m is 0-2; wherein the values of $R^{13}$ may be the same or different;

n is 1-2; wherein the values of $R^9$ may be the same or different;

z is 0-3; wherein the values of $R^{20}$ may be the same or different;

$R^{23}$, $R^{25}$, $R^{27}$, $R^{33}$, $R^{38}$, $R^{44}$, $R^{48}$ and $R^{54}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, $C_{1-10}$alkoxycarbonyl, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_e$-R$^{56}$—($C_{1-10}$alkylene)$_f$-, heterocyclyl-($C_{1-10}$alkylene)$_g$-R$^{57}$-($C_{1-10}$alkylene)$_h$-, carboxy, sulpho, sulphino, amidino, phosphono, —P(O)(OR$^{58}$)(OR$^{59}$), —P(O)(OH)(OR$^{58}$), —P(O)(OH)(R$^{58}$) or —P(O)(OR$^{59}$)(R$^{59}$), wherein $R^{58}$ and $R^{59}$ are independently selected from $C_{1-6}$alkyl; wherein $R^{23}$, $R^{25}$, $R^{27}$, $R^{33}$, $R^{38}$, $R^{44}$, $R^{48}$ and $R^{54}$ may be independently optionally substituted on carbon by one or more $R^{60}$; and wherein if said heterocyclyl contains an —NH— group, that nitrogen may be optionally substituted by a group selected from $R^{61}$;

$R^{24}$, $R^{26}$, $R^{28}$, $R^{34}$, $R^{39}$, $R^{45}$, $R^{49}$, $R^{55}$ and $R^{61}$ are independently selected from $C_{1-6}$alkyl, $C_{1-6}$alkanoyl, $C_{1-6}$alkylsulphonyl, sulphamoyl, N-($C_{1-6}$alkyl)sulphamoyl, N,N-($C_{1-6}$alkyl)$_2$sulphamoyl, $C_{1-6}$alkoxycarbonyl, carbamoyl, N-($C_{1-6}$alkyl)carbamoyl, N,N-($C_{1-6}$alkyl)$_2$carbamoyl, benzyl, phenethyl, benzoyl, phenylsulphonyl and phenyl;

$R^{29}$, $R^{30}$, $R^{40}$, $R^{41}$, $R^{50}$, $R^{51}$, $R^{56}$ and $R^{57}$ are independently selected from —O—, —NR$^{62}$—, —S(O)$_x$—, —NR$^{62}$C(O)NR$^{63}$—, —NR$^{62}$C(S)NR$^{63}$—, —OC(O)N=C—, —NR$^{62}$C(O)— or —C(O)NR$^{62}$—; wherein $R^{62}$ and $R^{63}$ are independently selected from hydrogen or $C_{1-6}$alkyl, and x is 0-2;

$R^{60}$ is selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2;

or a pharmaceutically acceptable salt, solvate, solvate of such a salt or a prodrug thereof.

In this specification the term "alkyl" includes both straight and branched chain alkyl groups but references to individual alkyl groups such as "propyl" are specific for the straight chain version only. For example, "$C_{1-10}$alkyl", "$C_{1-6}$alkyl" and "$C_{1-4}$alkyl" include propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Particularly a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1] heptyl, 4thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3-12 atoms; wherein a —CH$_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. More particularly "carbocyclyl" is cyclopropyl, cyclobutyl, 1-oxoyclopentyl, cyclopentyl, cyclopentenyl, cyclohexyl, cyclohexenyl, phenyl or 1-oxoindanyl.

An example of "$C_{1-10}$alkanoyloxy" and "$C_{1-6}$alkanoyloxy" is acetoxy. Examples of "$C_{1-10}$alkoxycarbonyl" and "$C_{1-6}$alkoxycarbonyl" include methoxycarbonyl, ethoxycarbonyl, n- and t-butoxycarbonyl. Examples of "$C_{1-10}$alkoxy" and "$C_{1-6}$alkoxy" include methoxy, ethoxy and propoxy. Examples of "$C_{1-10}$alkanoylamino" and "$C_{1-6}$alkanoylamino" include formamido, acetamido and propionylamino. Examples of "$C_{1-6}$alkanoyl-N—($C_{1-6}$alkyl)amino" include acetyl-N-methylamino and propionyl-N-ethyl-amino. Examples of "$C_{1-10}$alkylS(O)$_a$ wherein a is 0 to 2" and "$C_{1-6}$alkylS(O)$_a$ wherein a is 0 to 2" include methylthio, ethylthio, methylsulphinyl, ethylsulphinyl, mesyl and ethylsulphonyl. Examples of "$C_{1-10}$alkanoyl" and "$C_{1-6}$alkanoyl" include $C_{1-3}$alkanoyl, propionyl and acetyl. Examples of "N-($C_{1-10}$alkyl)amino" and "N-($C_{1-6}$alkyl)amino" include methylamino and ethylamino. Examples of "N,N-($C_{1-10}$alkyl)$_2$amino" and "N,N-($C_{1-6}$alkyl)$_2$amino" include di-N-methylamino, di-(N-ethyl)amino and N-ethyl-N-methylamino. Examples of "$C_{2-10}$alkenyl" and "$C_{2-6}$alkenyl" are vinyl, allyl and 1-propenyl. Examples of "$C_{2-10}$alkynyl" and "$C_{2-6}$alkynyl" are ethynyl, 1-propynyl and 2-propynyl. Examples of "$C^{2-6}$alkylene" are ethylene, propylene and butylene. Examples of "$C_{2-6}$alkenyloxy" are vinyloxy, allyloxy and 1-propenyloxy. Examples of "N-($C_{1-10}$alkyl)sulphamoyl" and "N-($C_{1-6}$alkyl)sulphamoyl" are N-($C_{1-3}$alkyl)sulphamoyl, N-(methyl)sulphamoyl and N-(ethyl)sulphamoyl. Examples of "N-($C_{1-10}$alkyl)$_2$sulphamoyl" and "N-($C_{1-6}$alkyl)$_2$sulphamoyl" are N,N-(dimethyl)sulphamoyl and N-(methyl)-N-(ethyl)sulphamoyl. Examples of "N-($C_{1-10}$alkyl)carbamoyl" and "N-($C_{1-6}$alkyl)carbamoyl" are methylaminocarbonyl and ethylaminocarbonyl. Examples of "N,N-($C_{1-10}$alkyl)$_2$carbamoyl" and "N,N-($C_{1-6}$alkyl)$_2$carbamoyl" are dimethylaminocarbonyl and methylethylaminocarbonyl. Examples of "N-($C_{1-10}$alkyl)carbamoyl" and "N-($C_{1-6}$alkyl)carbamoyloxy" are methylaminocarbonyloxy and ethylaminocarbonyloxy. Examples of "N,N-($C_{1-10}$alkyl)$_2$carbamoyl" and "N,N-($C_{1-6}$alkyl)$_2$carbamoyloxy" are dimethylaminocarbonyloxy and methylethylaminocarbonyloxy.

Examples of "$C_{1-6}$alkylsulphonyl" are mesyl and ethylsulphonyl. Examples of "$C_{1-10}$alkylsulphonylamino" and "$C_{1-6}$alkylsulphonylamino" are mesylamino and ethylsulphonylamino. Examples of "$C_{1-6}$alkylsulphonyl-N-($C_{1-6}$alkyl)amino" are mesyl-N-methylamino and ethylsulphonyl-N-propylamino. Examples of "N'-($C_{1-6}$alkyl)ureido" are N'-methylureido and N'-i-propylureido. Examples of "N-($C_{1-6}$alkyl)ureido" are N-methylureido and N-i-propylureido. Examples of "N',N'-($C_{1-6}$alkyl)$_2$ureido" are N',N'-dimethylureido and N'-methyl-N'-ethylureido. Examples of "N'-($C_{1-6}$alkyl)-N-($C_{1-6}$alkyl)ureido" are N',N-dimethylureido and N'-methyl-N-ethylureido. Examples of "N',N'-($C_{1-6}$alkyl)$_2$-N-($C_{1-6}$alkyl)ureido" are N',N'-dimethyl-N-methylureido and N'-methyl-N'-ethyl-N-t-butylureido. Examples of "N,N,N-($C_{1-10}$alkyl)$_3$ammonio" are trimethylamino and methyldiethylamino. Examples of "$C_{1-10}$alkoxycarbonylamino" and "$C_{1-6}$alkoxycarbonylamino" are methoxycarbonylamino and t-butoxycarbonylamino. Examples of "N-($C_{1-10}$alkyl)sulphamoylamino" are N-methylsulphamoylamino and N-ethylsulphamoylamino. Examples of "N,N-($C_{1-10}$alkyl)$_2$sulphamoylamino" are N,N-dimethylsulphamoylamino and N-methyl-N-ethylsulphamoylamino. Examples of "carbocyclyl$C_{1-10}$alkyl" include benzyl and phenethyl. Examples of "heterocyclyl$C_{1-10}$alkyl" include 2-morphoinopropyl and pyridylmethyl. Examples of "phenyl$C_{1-6}$alkoxy" include 2-phenylethoxy and 2-phenylpropoxy.

A suitable pharmaceutically acceptable salt of a compound of the invention, or other compounds disclosed herein, is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I), or other compounds disclosed herein, may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I), or other compounds disclosed herein, containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I), or other compounds disclosed herein, containing a hydroxy group includes inorganic esters such as phosphate esters and α-acyloxyalkyl ethers and related compounds which as a result of the in viva hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I), or other compounds disclosed herein, containing a carboxy group is, for example, a N-$C_{1-6}$ alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess cholesterol absorption inhibitory activity.

The invention relates to any and all tautomeric forms of the compounds of the formula (I) that possess cholesterol absorption inhibitory activity.

It is also to be understood that certain compounds of the formula (I) can exist in solvated as well as unsolvated forms such as, for example, hydrated forms. It is to be understood that the invention encompasses all such solvated forms which possess cholesterol absorption inhibitory activity.

Particular values are as follows. Such values may be used where appropriate with any of the definitions, claims or embodiments defined hereinbefore or hereinafter.

Ring A is selected from thienyl.
Ring A is selected from phenyl.
X is —$CR^2R^3$—.
X is —O—.
X is —$NR^x$—; wherein $R^x$ is hydrogen or $C_{1-6}$alkyl.
X is —$S(O)_a$—; wherein a is 0-2.
X is —$CR^2R^3$— wherein one of $R^2$ and $R^3$ is hydrogen and the other is hydroxy.
X is —$CH_2$—.
X is —CH(OH)—.
X is —C(O)—.
X is —S—.
X is —S(O)—.
X is —$S(O)_2$—.
X is selected from —$CR^2R^3$—, —O— and —$S(O)_a$—; wherein a is 0-2.
X is selected from —$CR^2R^3$—, —O— and —$S(O)_a$—; wherein a is 0-2; and $R^2$ and $R^3$ are independently selected from hydrogen and hydroxy; or $R^2$ and $R^3$ together form an oxo group.
X is selected from —$CH_2$—, —CH(OH)—, —C(O)—, —O—S—, —S(O)— and —$S(O)_2$—.
Y is —$CR^4R^5$—.
Y is —O—.
Y is —$NR^z$—; wherein $R^z$ is hydrogen or $C_{1-6}$alkyl.
Y is —$S(O)_a$—; wherein a is 0-2.
Y is —$CR^4R^5$— wherein $R^4$ and $R^5$ are both hydrogen.
Y is —$CH_2$—.
Y is —S—.
Y is —S(O)—.
Y is selected from —$CR^4R^5$— and —$S(O)_a$—; a is 0 or 1.
Y is selected from —$CR^4R^5$— and —$S(O)_a$—; a is 0 or 1; wherein $R^4$ and $R^5$ are both hydrogen.
Y is —$CH_2$—, —S— or —S(O)—.
X is —$CR^2R^3$— and Y is —$CR^4R^5$— wherein one of $R^2$ and $R^3$ is hydrogen and the other is hydroxy; and wherein $R^4$ and $R^5$ are both hydrogen.
X is —$CH_2$— and Y is —S—.
X is —C(O)— and Y is —S—.
X is —$CH_2$— and Y is —S(O)—.
X is —C(O)— and Y is —S(O)—.
X is —$CH_2$— and Y is —$S(O)_2$—.
X is —C(O)— and Y is —$S(O)_2$—.
X is —O— and Y is —$CH_2$—.
X is —CHOH— and Y is —$S(O)_a$—; wherein a is 0-2.
X is —CHOH— and Y is —S—.
X is —CHOH— and Y is —S(O)—.
X is —CHOH— and Y is —$S(O)_2$—.
$R^1$ is halo.
$R^1$ is fluoro.
$R^1$ is 4 fluoro if Ring A is phenyl.
b is 0-2; wherein the values of $R^1$ may be the same or different.
b is 0-1.
b is 1.
b is 0.
b is 1; wherein the substituent is para to the X group if Ring A is phenyl.
$R^2$ and $R^3$ are independently selected from hydrogen and hydroxy; or $R^2$ and $R^3$ together form an oxo group.
$R^2$ and $R^3$ are independently selected from hydrogen and hydroxy.
One of $R^2$ and $R^3$ is hydrogen and the other is hydroxy.
$R^4$ and $R^5$ are both hydrogen.
$R^6$ is halo or $C_{1-6}$alkoxy.
$R^6$ is halo.
$R^6$ is fluoro or methoxy.
$R^6$ is fluoro.
$R^6$ is 4-fluoro or 4-methoxy.
$R^6$ is 4-fluoro.
c is 0-2; wherein the values of $R^6$ may be the same or different.
c is 0-1.
c is 1.
c is 0.
c is 1; wherein the substituent is para to the nitrogen of the azetidin-2-one ring.
$R^7$ is halo, methoxy or ethoxy.
$R^7$ is fluoro or methoxy.
d is 0-2; wherein the values of $R^7$ may be the same or different.
d is 0-1.
d is 0.
$R^9$ is hydrogen.
$R^{10}$ is hydrogen.
$R^{11}$ and $R^{12}$ are independently selected from hydrogen or carbocyclyl.
$R^{11}$ and $R^{12}$ are independently selected from hydrogen or phenyl.
One of $R^{11}$ and $R^{12}$ is hydrogen and the other is phenyl or both $R^{11}$ and $R^{12}$ are hydrogen.
$R^{11}$ and $R^{12}$ are independently selected from hydrogen, $C_{1-4}$alkyl or carbocyclyl; wherein $R^{11}$ and $R^{12}$ may be independently optionally substituted on carbon by one or more substituents selected from $R^{25}$.
$R^{11}$ and $R^{12}$ are independently selected from hydrogen, methyl, ethyl, butyl, isobutyl or phenyl; wherein $R^{11}$ and $R^{12}$ may be independently optionally substituted on carbon by one or more substituents selected from $R^{25}$.
$R^{11}$ and $R^{12}$ are independently selected from hydrogen, $C_{1-4}$alkyl or carbocyclyl; wherein $R^{11}$ and $R^{12}$ may be independently optionally substituted on carbon by one or more substituents selected from $R^{25}$; wherein $R^{25}$ is selected from hydroxy, amino, carbamoyl, $C_{1-10}$alkoxycarbonyl, $C_{1-10}$alkoxycarbonylamino, carbocyclyl or carboxy; wherein $R^{25}$ may be optionally substituted on carbon by one or more $R^{60}$; wherein $R^{60}$ is hydroxy.

$R^{11}$ and $R^{12}$ are independently selected from hydrogen, methyl, ethyl, butyl, isobutyl or phenyl; wherein $R^{11}$ and $R^{12}$ may be independently optionally substituted on carbon by one or more substituents selected from $R^{25}$; wherein $R^{25}$ is selected from hydroxy, amino, carbamoyl, ethoxycarbonyl, t-butoxycarbonylamino, phenyl or carboxy; wherein $R^{25}$ may be optionally substituted on carbon by one or more $R^{60}$; wherein $R^{60}$ is hydroxy.

$R^{11}$ and $R^{12}$ are independently selected from hydrogen, methyl, hydroxymethyl, 2-carbamoylethyl, 2-(ethoxycarbonyl)ethyl, 2-carboxyethyl, 4-(t-butoxycarbonylamino)butyl, 4-aminobutyl, isobutyl, phenyl, 4-hydroxyphenyl and 4-hydroxybenzyl.

One of $R^{11}$ and $R^{12}$ is hydrogen and the other is selected from hydrogen, methyl, hydroxymethyl, 2-carbamoylethyl, 2-(ethoxycarbonyl)ethyl, 2-carboxyethyl, 4-(t-butoxycarbonylamino)butyl, 4-aminobutyl, isobutyl, phenyl, 4-hydroxyphenyl and 4-hydroxybenzyl.

$R^{13}$ is hydrogen.

$R^{14}$ is $C_{1-10}$alkyl, $C_{1-10}$alkoxycarbonyl or carboxy; wherein $R^{14}$ may be optionally substituted on carbon by one or more substituents selected from $R^{33}$; or $R^{14}$ is a group of formula (IA) as depicted above.

$R^{14}$ is $C_{1-6}$alkyl, $C_{1-6}$alkoxycarbonyl or carboxy; wherein $R^{14}$ may be optionally substituted on carbon by one or more hydroxy; or $R^{14}$ is a group of formula (IA) as depicted above.

$R^{14}$ is 1,2,3,4,5-pentahydroxypentyl, t-butoxycarbonyl or carboxy; or $R^{14}$ is a group of formula (IA) as depicted above.

$R^{14}$ is hydroxy, $C_{1-10}$alkyl, $C_{1-10}$alkoxy, $C_{1-10}$alkoxycarbonyl, carboxy or sulpho;

wherein $R^{14}$ may be optionally substituted on carbon by one or more substituents selected from $R^{33}$; or $R^{14}$ is a group of formula (IA) (as depicted above).

$R^{14}$ is hydroxy, pentyl, methoxy, ethoxycarbonyl, t-butoxycarbonyl, carboxy or sulpho; wherein $R^{14}$ may be optionally substituted on carbon by one or more substituents selected from $R^{33}$; or $R^{14}$ is a group of formula (IA) (as depicted above).

$R^{15}$ is hydrogen.

$R^{16}$ and $R^{17}$ are independently selected from hydrogen, carboxy or $C_{1-6}$alkoxycarbonyl.

$R^{16}$ and $R^{17}$ are independently selected from hydrogen, carboxy or t-butoxycarbonyl.

One of $R^{16}$ and $R^{17}$ is hydrogen, and the other is hydrogen, carboxy or t-butoxycarbonyl.

$R^{16}$ and $R^{17}$ are independently selected from hydrogen, carboxy, $C_{1-6}$alkyl and $C_{1-6}$alkoxycarbonyl.

$R^{16}$ and $R^{17}$ are independently selected from hydrogen, carboxy, $C_{1-6}$alkyl and t-butoxycarbonyl.

$R^{18}$ is selected from hydroxy, $C_{1-10}$alkoxy, $C_{1-10}$alkoxycarbonyl or carboxy.

$R^{18}$ is selected from hydroxy, $C_{1-6}$alkoxy, $C_{1-6}$alkoxycarbonyl or carboxy.

$R^{18}$ is selected from hydroxy, t-butoxy, t-butoxycarbonyl or carboxy.

$R^{18}$ is selected from hydroxy, $C_{1-10}$alkyl, $C_{1-10}$alkoxy, $C_{1-10}$alkoxycarbonyl, carboxy and sulpho.

$R^{18}$ is selected from hydroxy, methyl, t-butoxy, ethoxycarbonyl, t-butoxycarbonyl, carboxy and sulpho.

p is 1.

q is 0.

r is 0 or 1.

m is 0.

m is 1.

m is 0 or 1.

n is 1.

$R^{14}$ is hydroxy, $C_{1-10}$alkyl, $C_{1-10}$alkoxy, $C_{1-10}$alkoxycarbonyl, carboxy or sulpho; wherein $R^{14}$ may be optionally substituted on carbon by one or more substituents selected from $R^{33}$; or $R^{14}$ is a group of formula (IA) (as depicted above) wherein:

$R^{15}$ is hydrogen;

$R^{16}$ and $R^{17}$ are independently selected from hydrogen, carboxy, $C_{1-6}$alkyl and $C_{1-6}$alkoxycarbonyl;

$R^{18}$ is selected from hydroxy, $C_{1-10}$alkyl, $C_{1-10}$alkoxy, $C_{1-10}$alkoxycarbonyl, carboxy and sulpho;

p is 1;

q is 0;

r is 0 or 1;

m is 0 or 1;

n is 1; and $R^{33}$ is hydroxy.

$R^{14}$ is hydroxy, pentyl, methoxy, ethoxycarbonyl, t-butoxycarbonyl, carboxy or sulpho; wherein $R^{14}$ may be optionally substituted on carbon by one or more substituents elected from $R^{33}$; or $R^{14}$ is a group of formula (IA) (as depicted above) wherein:

$R^{15}$ is hydrogen;

$R^{16}$ and $R^{17}$ are independently selected from hydrogen, carboxy, $C_{1-6}$alkyl and t-butoxycarbonyl;

$R^{18}$ is selected from hydroxy, methyl, t-butoxy, ethoxycarbonyl, t-butoxycarbonyl, carboxy and sulpho;

p is 1;

q is 0;

r is 0 or 1;

m is 0 or 1;

n is 1; and $R^{33}$ is hydroxy.

$R^{25}$ is selected from hydroxy, amino, carbamoyl, $C_{1-10}$alkoxycarbonyl, $C_{1-10}$alkoxycarbonylamino, carbocyclyl or carboxy; wherein $R^{25}$ may be optionally substituted n carbon by one or more $R^{60}$.

$R^{25}$ is selected from hydroxy, amino, carbamoyl, ethoxycarbonyl, t-butoxycarbonylamino, phenyl or carboxy; wherein $R^{25}$ may be optionally substituted on carbon by one or more $R^{60}$.

$R^{25}$ is selected from hydroxy, amino, carbamoyl, $C_{1-10}$alkoxycarbonyl, $C_{1-10}$alkoxycarbonylamino, carbocyclyl or carboxy; wherein $R^{25}$ may be optionally substituted on carbon by one or more $R^{60}$; wherein $R^{60}$ is hydroxy.

$R^{25}$ is selected from hydroxy, amino, carbamoyl, ethoxycarbonyl, t-butoxycarbonylamino, phenyl or carboxy; wherein $R^{25}$ may be optionally substituted on carbon by one or more $R^{60}$; wherein $R^{60}$ is hydroxy.

$R^{33}$ is hydroxy.

$R^{60}$ is hydroxy.

The side chain $R_{14}$—$[C(R^{13})]_m$—$C(R^{11})(R^{12})$—$N(R^{10})$—$C(O)$—$[C(R^9)]_n$—$O$— is N-(2-sulphoethyl)carbamoylmethoxy; N-(carboxymethyl)carbamoylmethoxy;

N-(2-hydroxyethyl)carbamoylmethoxy; N-(2-methoxyethyl)carbamoylmethoxy;

N-[2-(carboxy)ethyl]carbamoylmethoxy; N-[(S)-1-(carboxy)ethyl]carbamoylmethoxy;

N-[(R)-1-(carboxy)ethyl]carbamoylmethoxy; N-[(S )-α-(carboxy)benzyl]carbamoylmethoxy;

N-[(R)-α-(carboxy)benzyl]carbamoylmethoxy;

N-(t-butoxycarbonylmethyl)carbamoylmethoxy;

N-[2-(t-butoxycarbonyl)ethyl]carbamoylmethoxy;

N-[(S)-1,3-bis-(carboxy)propyl]carbamoylmethoxy;

N-((R)-1-carboxy-3-methylbutyl)carbamoylmethoxy;

N-[(S)-1-(t-butoxycarbonyl)ethyl]carbamoylmethoxy;

N-[(R)-1-(t-butoxycarbonyl)ethyl]carbamoylmethoxy;

N-[(R)-α-(t-butoxycarbonyl)benzyl]carbamoylmethoxy;

N-[(S)-1-(carboxy)-5-(amino)pentyl]carbamoylmethoxy;

N-[(R)-1-(carboxy)-2-(hydroxy)ethyl]carbamoylmethoxy;

N-[(S)-1,3-bis-(ethoxycarbonyl)propyl]carbamoylmethoxy;

N-[(R)-α-(carboxy)-4-(hydroxy)benzyl]carbamoylmethoxy;

N-[N-(carboxymethyl)carbamoylmethyl]carbamoylmethoxy;

N-[(S)-1-(carboxy)-3-(carbamoyl)propyl]carbamoylmethoxy;

N-{(R)-α-[N-(carboxymethyl)carbamoyl]benzyl}carbamoylmethoxy;

N-[N-(methoxycarbonylmethyl)carbamoylmethyl]carbamoylmethoxy;

N-((S)-1-{N-[(S)-1-(carboxy)ethyl]carbamoyl}ethyl)carbamoylmethoxy;

N-((2-(S)-3-(R)-4-(R)-5-(R)-2,3,4,5,6-pentahydroxyhexyl)carbamoylmethoxy;

N-{(R)-α-[N-(t-butoxycarbonylmethyl)carbamoyl]benzyl}carbamoylmethoxy;

N-{(R)-α-[N-(2-sulphoethyl)carbamoyl]-4-hydroxybenzyl}carbamoylmethoxy;

N-{N-[(R)-1-(carboxy)-2-(hydroxy)ethyl]carbaoylrethyl}carbamoylmethoxy;

N-[(S)-1-(t-butoxycarbonyl)-5-(t-butoxycarbonylamino)pentyl]carbamoylmethoxy;

N-((S)-1-{N-[(S)-1-(t-butoxycarbonyl)ethyl]carbamoyl}ethyl)carbamoylmethoxy;

N-{(R)-α-[N-((S)-1-carboxypropyl)carbamoyl]4-hydroxybenzyl}carbamoylmethoxy;

N-((R)-α-{N-[(S)-1-(carboxy)-2-(hydroxy)ethyl]carbamoyl}benzyl)carbamoylmethoxy;

N-{N-[(R)-1-(t-butoxycarbonyl)-2-(t-butoxy)ethyl]carbamoylmethyl}carbamoylmethoxy; or N-((R)-α-{N-(S)-[1-(t-butoxycarbonyl)-2-(t-butoxy)ethyl]carbamoyl}benzyl)carbamoylmetho xy.

Therefore in another aspect of the invention, there is provided a compound of formula (I) (as depicted above) wherein:
Ring A is phenyl;
X is —$CR^2R^3$—;
Y is —$CR^4R^5$—;
$R^1$ is halo;
b is 1;
One of $R^2$ and $R^3$ is hydrogen and the other is hydroxy;

$R^4$ and $R^5$ are both hydrogen;
$R^6$ is halo;
c is 1;
d is 0;
$R^9$ is hydrogen;
$R^{10}$ is hydrogen;
$R^{11}$ and $R^{12}$ are independently selected from hydrogen or carbocyclyl;
$R^{14}$ is $C_{1-10}$alkyl, $C_{1-10}$alkoxycarbonyl or carboxy; wherein $R^{14}$ may be optionally substituted on carbon by one or more substituents selected from $R^{33}$; or $R^{14}$ is a group of formula (IA) as depicted above;
$R^{15}$ is hydrogen;
$R^{16}$ and $R^{17}$ are independently selected from hydrogen, carboxy or $C_{1-6}$alkoxycarbonyl;
$R^{18}$ is selected from hydroxy, $C_{1-10}$alkoxy, $C_{1-10}$alkoxycarbonyl or carboxy;
p is 1;
q is 0;
r is 0 or 1;
m is 0;
n is 1;
$R^{33}$ is hydroxy;

or a pharmaceutically acceptable salt, solvate, solvate of such a salt or a prodrug thereof.

Therefore in another aspect of the invention, there is provided a compound of formula (I) (as depicted above) wherein:
Ring A is selected from phenyl;
X is —$CR^2R^3$— and Y is —$CR^4R^5$— wherein one of $R^2$ and $R^3$ is hydrogen and the other is hydroxy; and wherein $R^4$ and $R^5$ are both hydrogen;
$R^1$ is 4-fluoro;
b is 1;
$R^6$ is 4-fluoro;
c is 1;
d is 0;
$R^9$ is hydrogen;
$R^{10}$ is hydrogen;
One of $R^{11}$ land $R^{12}$ is hydrogen and the other is phenyl or both $R^{11}$ land $R^{12}$ are hydrogen;
$R^{14}$ is 1,2,3,4,5-pentahydroxypentyl, t-butoxycarbonyl or carboxy; or $R^{14}$ is a group of formula (IA) as depicted above;
$R^{15}$ is hydrogen;
One of $R^{16}$ and $R^{17}$ is hydrogen, and the other is hydrogen, carboxy or t-butoxycarbonyl;
$R^{18}$ is selected from hydroxy, t-butoxy, t-butoxycarbonyl or carboxy;
p is 1;
q is 0;
r is 0 or 1;
m is 0;
n is 1;
$R^{33}$ is hydroxy;

or a pharmaceutically acceptable salt, solvate, solvate of such a salt or a prodrug thereof.

Therefore in another aspect of the invention, there is provided a compound of formula (I) (as depicted above) wherein:
Ring A is selected from phenyl or thienyl;
X is selected from —$CR^2R^3$—, —O— and —$S(O)_a$—; wherein a is 0-2; and $R^2$ and $R^3$ are independently selected from hydrogen and hydroxy; or $R^2$ and $R^3$ together form an oxo group;
Y is selected from —$CR^4R^5$— and —$S(O)_a$—; a is 0 or 1; wherein $R^4$ and $R^5$ are both hydrogen;
$R^1$ is halo;
b is 0-1;

$R^6$ is halo;
c is 0-1;
d is 0;
$R^9$ is hydrogen;
$R^{10}$ is hydrogen;
$R^{11}$ and $R^{12}$ are independently selected from hydrogen, $C_{1-4}$alkyl or carbocyclyl;

wherein $R^{11}$ and $R^{12}$ may be independently optionally substituted on carbon by one or more substituents selected from $R^{25}$; wherein $R^{25}$ is selected from hydroxy, amino, carbamoyl, $C_{1-10}$alkoxycarbonyl, $C_{1-10}$alkoxycarbonylamino, carbocyclyl or carboxy; wherein $R^{25}$ may be optionally substituted on carbon by one or more $R^{60}$; wherein $R^{60}$ is hydroxy;
$R^{13}$ is hydrogen;
$R^{14}$ is hydroxy, $C_{1-10}$alkyl, $C_{1-10}$alkoxy, $C_{1-10}$alkoxycarbonyl, carboxy or sulpho; wherein $R^{14}$ may be optionally substituted on carbon by one or more substituents selected from $R^{33}$; or $R^{14}$ is a group of formula (IA) (as depicted above) wherein:
$R^{15}$ is hydrogen;
$R^{16}$ and $R^{17}$ are independently selected from hydrogen, carboxy, $C_{1-6}$alkyl and $C_{1-6}$alkoxycarbonyl;
$R^{18}$ is selected from hydroxy, $C_{1-10}$alkyl, $C_{1-10}$alkoxy, $C_{1-10}$alkoxycarbonyl, carboxy and sulpho;
p is 1;
q is 0;
r is 0 or 1;
m is 0 or 1;
n is 1; and
$R^{33}$ is hydroxy;

or a pharmaceutically acceptable salt, solvate, solvate of such a salt or a prodrug thereof.

Therefore in another aspect of the invention, there is provided a compound of formula (I) (as depicted above) wherein:
Ring A is selected from phenyl or thienyl;
X is selected from —$CH_2$—, —CH(OH)—, —C(O)—, —O—S—, —S(O)— and —$S(O)_2$—;
Y is —$CH_2$—, —S— or —S(O)—;
$R^1$ is fluoro;
b is 0-1;
$R^6$ is fluoro;
c is 0-1;
d is 0;
$R^9$ is hydrogen;
$R^{10}$ is hydrogen;
One of $R^{11}$ and $R^{12}$ is hydrogen and the other is selected from hydrogen, methyl, hydroxymethyl, 2-carbamoylethyl, 2-(ethoxycarbonyl)ethyl, 2-carboxyethyl, 4-(t-butoxycarbonylamino)butyl, 4-aminobutyl, isobutyl, phenyl, 4-hydroxyphenyl and 4-hydroxybenzyl;
$R^{13}$ is hydrogen;
$R^{14}$ is hydroxy, pentyl, methoxy, ethoxycarbonyl, t-butoxycarbonyl, carboxy or sulpho; wherein $R^{14}$ may be optionally substituted on carbon by one or more substituents selected from $R^{33}$; or $R^{14}$ is a group of formula (IA) (as depicted above) wherein:
$R^{15}$ is hydrogen;
$R^{16}$ and $R^{17}$ are independently selected from hydrogen, carboxy, $C_{1-6}$alkyl and t-butoxycarbonyl;
$R^{18}$ is selected from hydroxy, methyl, t-butoxy, ethoxycarbonyl, t-butoxycarbonyl, carboxy and sulpho;
p is 1;
q is 0;
r is 0 or 1;
m is 0 or 1;
n is 1; and
$R^{33}$ is hydroxy;

or a pharmaceutically acceptable salt, solvate, solvate of such a salt or a prodrug thereof.

In another aspect of the invention, preferred compounds of the invention are any one of the examples or a pharmaceutically acceptable salt, solvate, solvate of such a salt or a prodrug thereof.

In another aspect of the invention, preferred compounds of the invention are:

1-(4-fluorophenyl)-3-[3-(4-fluorophenyl)-3-hydroxypropyl]-4-{4-[N-((R)-α-{N-(S)-[1-(carboxy)-2-(hydroxy)ethyl]carbamoyl}benzyl)carbamoylmethoxy]phenyl}azetidin-2-one;

1-(4-fluorophenyl)-3-[3-(4-fluorophenyl)-3-hydroxypropyl]-4-(4-{N-[(R)-α-(carboxy)benzyl]carbamoylmethoxy}phenyl)azetidin-2-one;

1-(4-fluorophenyl)-3-[3-(4-fluorophenyl)-3-hydroxypropyl]-4-{4-[N-(carboxymethyl)carbamoylmethoxy]phenyl}azetidin-2-one;

1-(4-fluorophenyl)-3-[3-(4-fluorophenyl)-3-hydroxypropyl]-4-(4-{N-[N-(carboxymethyl)carbamoylmethyl]carbamoylmethoxy}phenyl)azetidin-2-one;

1-(4-fluorophenyl)-3-[3-(4-fluorophenyl)-3-hydroxypropyl]-4-{4-[N-(2-hydroxyethyl)carbamoylmethoxy]phenyl}azetidin-2-one;

1-(4-fluorophenyl)-3-[3-(4-fluorophenyl)-3-hydroxypropyl]-4-{4-[N-(2-methoxyethyl)carbamoylmethoxy]phenyl}azetidin-2-one;

3-(R)-4-(R)-1-(phenyl)-3-(4-fluorobenzoylmethylsulphanyl)-4-{4-[N-(carboxymethyl)carbamoylmethoxy]phenyl}azetidin-2-one;

3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one;

3-(R)-4-(R)-1-(phenyl)-3-[2-(thien-3-yl)-2-hydroxyethylsulphanyl]-4-{4-[N-(carboxymethyl)carbamoylmethoxy]phenyl}azetidin-2-one;

3-(R)-4-(R)-1-(phenyl)-3-[2-(thien-3-yl)-2-hydroxyethylsulphanyl]-4-{4-[N-((R)-α-{N-[(S)-1-(carboxy)-2-(hydroxy)ethyl]carbamoyl}benzyl)carbamoylmethoxy]phenyl}azetidin-2-one;

3-(R)-4-(R)-1-(phenyl)-3-(4-fluorobenzoylmethylsulphanyl)-4-{4-[N-(R)-α-{N-[(S)-1-(carboxy)-2-(hydroxy)ethyl]carbamoyl}benzyl)carbamoylmethoxy]phenyl}azetidin-2-one; and 3-(R)-4-(R)-1-(phenyl)-3-[2-(4-fluorophenyl)-2-hydroxyethylsulphanyl]-4-{4-[N-((R)-α-{N-[(S)-1-(carboxy)-2-(hydroxy)ethyl]carbamoyl}benzyl)carbamoylmethoxy]phenyl}azetidin-2-one;

or a pharmaceutically acceptable salt, solvate, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1) reacting a compound of formula (II):

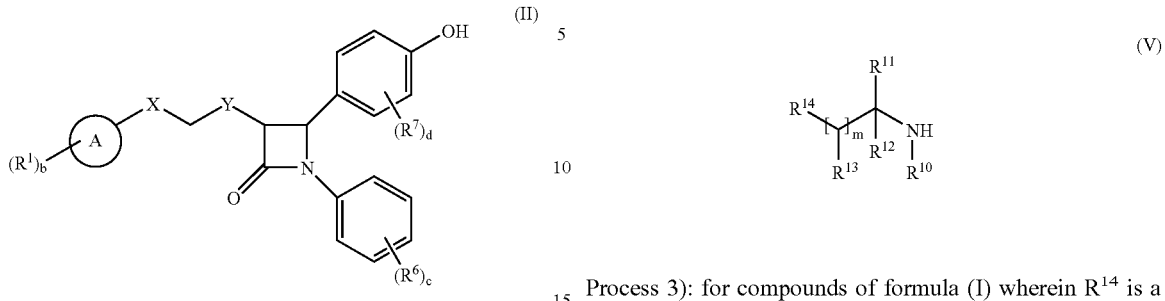

with a compound of formula (III):

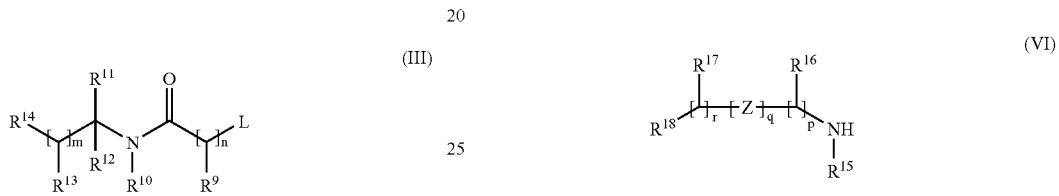

wherein L is a displaceable group;

Process 2) reacting an acid of formula MV):

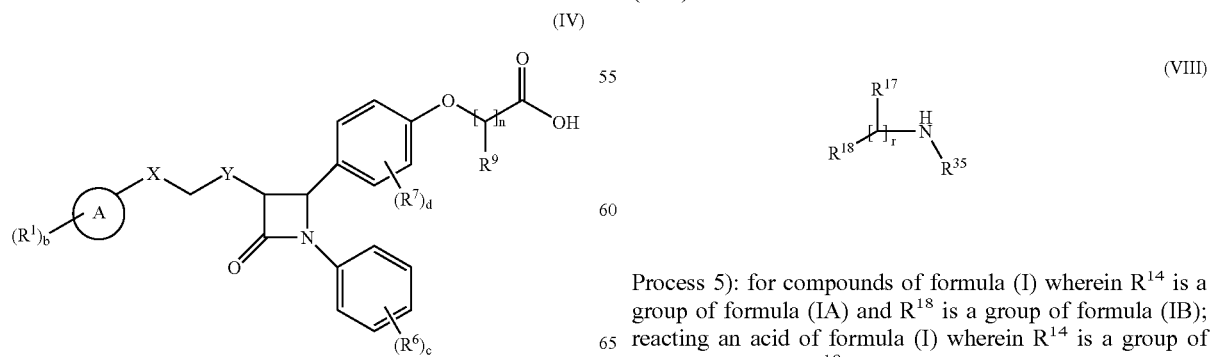

or an activated derivative thereof; with an amine of formula (V):

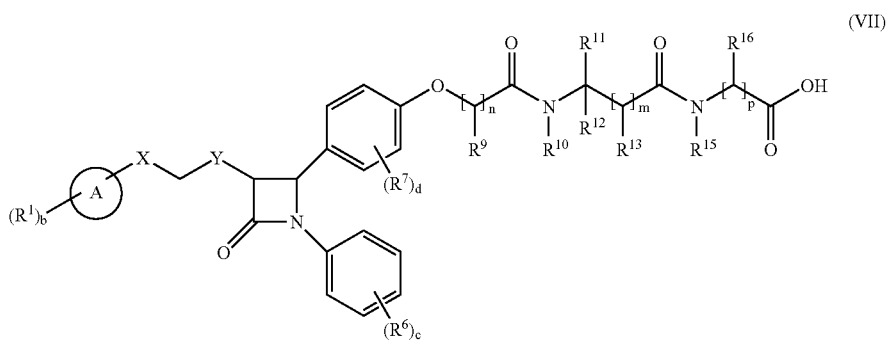

Process 3): for compounds of formula (I) wherein $R^{14}$ is a group of formula (IA); reacting a compound of formula (VI) wherein $R^{14}$ is carboxy, or an activated derivative thereof, with an amine of formula (VI):

Process 4): for compounds of formula (I) wherein $R^{14}$ is a group of formula (IA), Z is —N($R^{35}$)C(O)— and q is 1; reacting an acid of formula (VII):

or an activated derivative thereof; with an amine of formula (VIII):

Process 5): for compounds of formula (I) wherein $R^{14}$ is a group of formula (IA) and $R^{18}$ is a group of formula (IB); reacting an acid of formula (I) wherein $R^{14}$ is a group of formula (IA) and $R^{18}$ is carboxy, or an activated derivative thereof, with an amine of formula (IX)

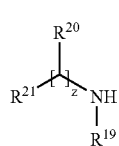
(IX)

Process 6): reacting a compound of formula (X):

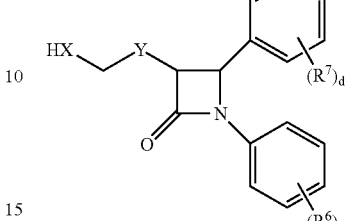
(XIV)

with a compound of formula (XI):

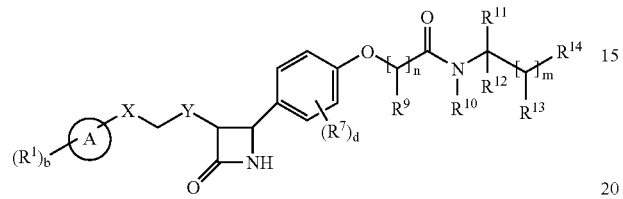
(XII)

with a compound of formula (XV):

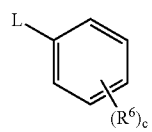
(XI)

wherein L is a displaceable group;

Process 7): for compounds of formula (I) wherein X is selected from —O—, —NR$^x$— and —S(O)$_a$— wherein a is 0; reacting a compound of formula (XII):

(XV)

wherein L is a displaceable group;

Process 9): for compounds of formula (I) wherein Y is selected from —O—, —NR$^z$— and —S(O)$_a$— wherein a is 0; reacting a compound of formula (XVI):

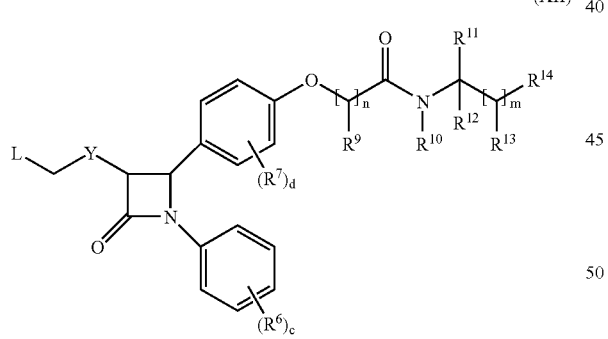
(XII)

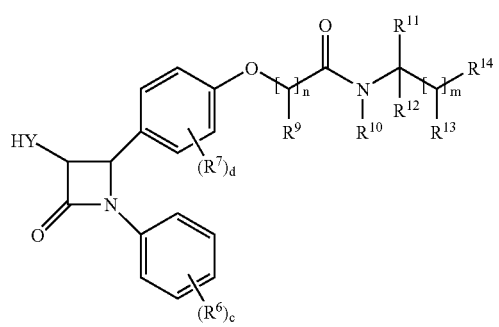
(XVI)

with a compound of formula (XVII):

wherein L is a displaceable group; with a compound of formula (XIII):

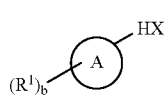
(XIII)

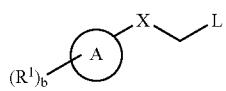
(XVII)

wherein L is a displaceable group;

Process 8): for compounds of formula (I) wherein X is selected from —O—, —NR$^x$— and —S(O)$_a$— wherein a is 0; reacting a compound of formula (XIV):

Process 10): for compounds of formula (I) wherein Y is selected from —O—, —NR$^z$— and —S(O)$_a$— wherein a is 0; reacting a compound of formula (XVIII):

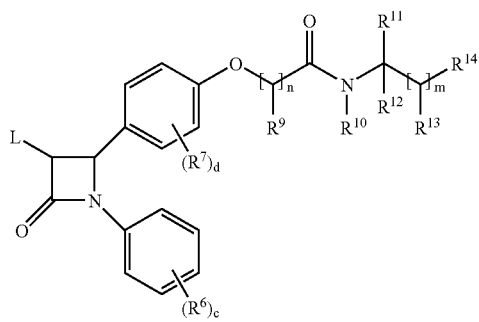

wherein L is a displaceable group; with a compound of formula (XIX):

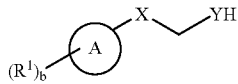

Process 11): for compounds of formula (I) wherein X or Y is —S(O)$_a$— and a is 1 or 2; oxidizing a compound of formula (I) Wherein X or Y is —S(O)$_a$— and a is 0 (for compounds of formula (I) wherein and a is 1 or 2) or a is 1 (for compounds of formula (I) wherein and a is 2);

and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug; or iv) separating two or more enantiomers.

L is a displaceable group, suitable values for L are for example, a halogeno or sulphonyloxy group, for example a chloro, bromo, methanesulphonyloxy or toluenesulphonyloxy group.

Specific reaction conditions for the above reactions are as follows. Process 1): Alcohols of formula (II) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (II wherein X is —CR$^2$R$^3$—, Y is selected from —CR$^4$R$^5$—, R$^2$ and R$^3$ together form an oxo group and R$^4$ and R$^5$ are both hydrogen; may be prepared according to the following scheme:

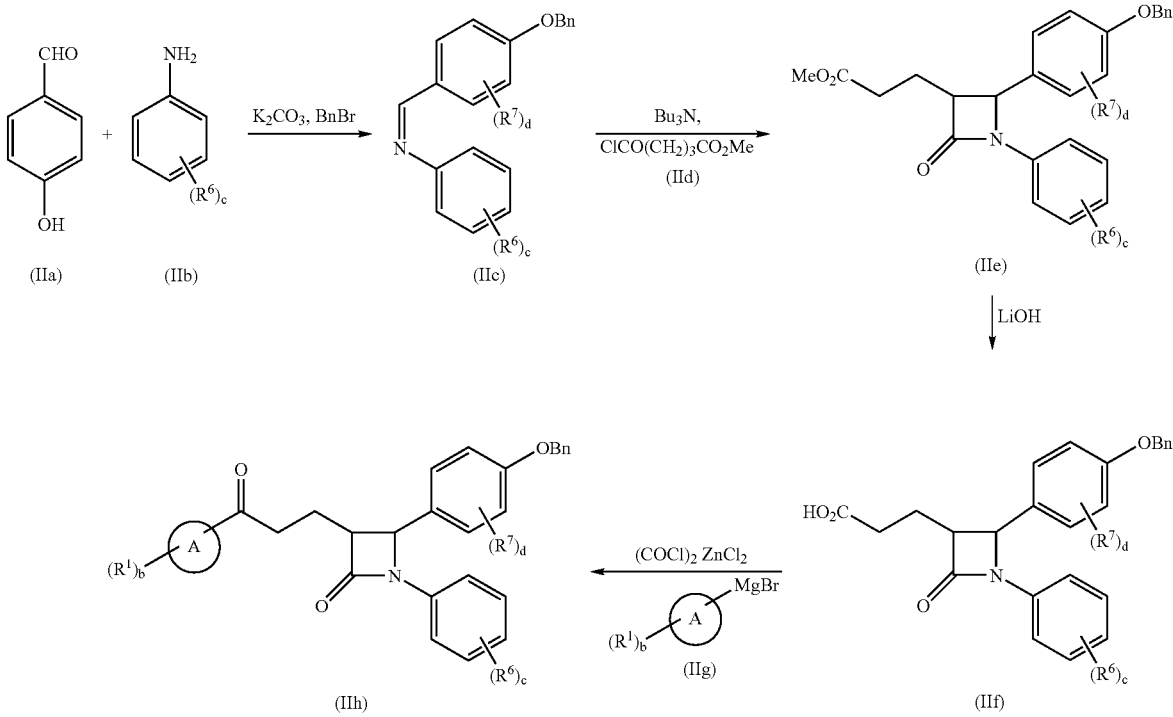

Followed by removal of the benzyl protecting group.

Compounds of formula (II) with different values of X and Y may be prepared by the above scheme, but with modifications that would be known to the skilled man. For example compound (IIh) could be modified to give other values of $R^2$ and $R^3$ or compound (IId) could be substituted for an alternative compound that had the desired functionality, this compound could potentially include Ring A.

Compounds of formula (III) are commercially available compounds, or they are known in the literature, or they are prepared by standard processes known in the art. Process 2), Process 3), Process 4) and Process 5): Acids and amines may be coupled together in the presence of a suitable coupling reagent. Standard peptide coupling reagents known in the art can be employed as suitable coupling reagents, for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6 di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Acids of formula (IV) and (VII) may be prepared from compounds of formula (II) by reacting them with the appropriate, optionally protected, side chain using the conditions of Process 1).

Amines of formula (V), (VI), (VII) and (IX) are commercially available compounds, or they are known in the literature, or they are prepared by standard processes known in the art.

Process 6): Compounds of formula (X) may be reacted with compounds of formula (XI) in the presence of a base for example an inorganic base such as sodium carbonate, or an organic base such as Hunigs base, in the presence of a suitable solvent such as acetonitrile, dichloromethane, DMF or tetrahydrofuran at a temperature in the range of 0° C. to reflux, preferably at or near reflux. Alternatively this reaction may be performed using transition metal chemistry known to the skilled person, for example copper or palladium chemistry.

Compounds of formula (X) may be prepared according to Scheme 1 with a suitable replacement for compound (IIb), for example benzylamine, followed by debenzylation at an appropriate point in the synthetic scheme.

Compounds of formula (XI) are commercially available compounds, or they are known in the literature, or they are prepared by standard processes known in the art. Process 7), Process 8), Process 9) and Process 10): these compounds may be reacted together in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (XII), (XIV), (XVI) and (XVIII) may be prepared according to Scheme 1 with a suitable replacement for compound (IId).

Compounds of formula (XIII), (XV), (XVII) and (XIX) are commercially available compounds, or they are known in the literature, or they are prepared by standard processes known in the art.

Process 11): These compounds may be oxidised under standard sulphur oxidation conditions; for example using hydrogen peroxide and trifluoroacetic acid at a temperature in the range of 0° C. to reflux, preferably at or near room temperature.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess cholesterol absorption inhibitory activity These properties may be assessed, using the following biological test.

In Vivo Testing of Cholesterol Absorption Inhibitors

C57BL/6 female mice were maintained on regular chow diet and housed in individual cages to collect faeces. Mice were fasted for 3 hours and then gavaged with vehicle or compound. Half an hour later the mice were gavaged with radiolabelled cholesterol. Two or six hours after the $^{14}C$-cholesterol gavage blood samples were taken via the tail and plasma prepared to determine how much cholesterol were absorbed. 24 hours after the gavage of $^{14}C$-cholesterol the mice were bled to death and plasma were prepared for analysis. Faeces were collected for 24 hours to assess absorption efficiency.

References

1. E. A. Kirk, G. L. Moe, M. T. Caldwell, J. Å. Lernmark, D. L. Wilson, R. C. LeBoeuf. Hyper- and hypo-responsiveness to dietary fat and cholesterol among inbred mice: searching for level and variability genes. J. Lipid Res. 1995 36:1522-1532.

2. C. P. Carter, P. N. Howles, D. Y. Hui. Genetic variation in cholesterol absorption efficiency among inbred strains of mice. J. Nutr. 1997 127:1344-1348.

3. C. D. Jolley, J. M. Dietschy, S. D. Turley. Genetic differences in cholesterol absorption in 129/Sv and C57BL/6 mice: effect on cholesterol responsiveness. Am. J. Physiol. 1999 276:G1117-G1124.

Absorption

The absorption of the compounds of formula (I) was tested in a Caco-2 cells model (Gastroenterology 1989, 96, 736).

The data below shoes that Example 24 shows much lower absorption compared with ezetimibe (US RE37721).

| Compound | Example 24 | Ezetimibe |
|---|---|---|
| Apparent partition coefficient; $P_{app}$ [cm/s] | $0.24 \times 10^{-06}$ | $21 \times 10^{-06}$ |

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range of approximately 0.02-100 mg/kg, preferably 0.02-50 mg/kg, and this normally provides a therapeutically-effective dose. A unit dose form such as a tablet or capsule will usually contain, for example 1-250 mg of active ingredient. Preferably a daily dose in the range of 1-50 mg/kg, particularly 0.1-10 mg/kg is employed. In another aspect a daily dose in the rage of 0.01-20 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective cholesterol absorption inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of a cholesterol absorption inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the production of a cholesterol absorption inhibitory effect in a warm-blooded animal, such as man.

Herein, where the production of a cholesterol absorption inhibitory effect or a cholesterol lowering effect is stated, suitably this relates to the treatment of hyperlipidaemic conditions in a warm-blooded animal, such as man. Additionally is relates to the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man. Furthermore it relates to the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man. It also relates to the treatment of atherosclerosis, coronary heart diseases, myocardial infarction, angina pectoris, peripheral vascular diseases, stroke and transient ischaemic attacks in a warm-blooded animal, such as man.

The production of a cholesterol absorption inhibitory effect or a cholesterol lowering effect also relates to a method of treating and/or preventing atherosclerotic lesions, a method of preventing plaque rupture and a method of promoting lesion regression. Furthermore it relates to a method of inhibiting monocytes-macrophage accumulation in atherosclerotic lesions, a method of inhibiting expression of matrix metalloproteinases in atherosclerotic lesions, a method of inhibiting the destabilization of atherosclerotic lesions, a method for preventing atherosclerotic plaque rupture and a method of treating unstable angina The production of a cholesterol absorption inhibitory effect or a cholesterol lowering effect also relates to a method of treating sitosterolemia.

Compounds of formula (I), or a pharmaceutically acceptable salt, solvate, solvate of such a salt or a prodrug thereof may also have value in the treatment or prevention of Alzeheimer's Disease (see for example WO 02/096415). Therefore in a further aspect of the invention, there is provided a compound of formula (I), or a pharmaceutically acceptable salt, solvate, solvate of such a salt or a prodrug thereof, for use in the treatment or prevention of Alzeheimer's Disease.

Compounds of formula (I), or a pharmaceutically acceptable salt, solvate, solvate of such a salt or a prodrug thereof may also have value in the treatment or prevention of vascular inflammation (see for example WO 03/026644). Therefore in a further aspect of the invention, there is provided a compound of formula (I), or a pharmaceutically acceptable salt, solvate, solvate of such a salt or a prodrug thereof, for use in the treatment or prevention of vascular inflammation.

According to a further feature of this aspect of the invention there is provided a method for producing a cholesterol absorption inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

The cholesterol absorption inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional cholesterol absorption inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with cholesterol biosynthesis inhibitors, or pharmaceutically acceptable salts, solvates, solvates of such salts or prodrugs thereof. Suitable cholesterol biosynthesis inhibitors include HMG Co-A reductase inhibitors, squalene synthesis inhibitors and squalene epoxidase inhibitors. A suitable squalene synthesis inhibitor is squalestatin 1 and a suitable squalene epoxidase inhibitor is NB-598.

In this aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and rosuvastatin, or a pharmaceutically acceptable salt, solvate, solvate of such a salt or a prodrug thereof. A further particular statin is pitvastatin, or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is rosuvastatin, or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an HMG Co-A reductase inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an HFG Co-A reductase inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of a cholesterol lowering effect.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an H-MG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of a matrix metalloproteinase inhibitor.

In another aspect of the invention, the compound of formula (I), or a pharmaceutically acceptable salt, solvate, solvate of such a salt or a prodrug thereof, may be administered in association with an ileal bile acid (IBAT) inhibitor or a pharmaceutically acceptable salt solvate, solvate of such a salt or a prodrug thereof. Suitable compounds possessing such IBAT inhibitory activity have been described, see for instance hypolipidaemic compounds described in WO 93/16055, WO 94/18183, WO 94/18184, WO 96/05188, WO 96/08484, WO 15 96/16051, WO 97/33882, WO 98/38182, WO 99/35135, WO 98/40375, WO 99/64409, WO 99/64410, WO 00/01687, WO 00/47568, WO 00/61568, DE 19825804, WO 00/38725, WO 00/38726, WO 00/38727, WO 00/38728, WO 00/38729, WO 01/66533, WO 02/50051 and EP 0 864 582 and the compound described in these patent applications, particularly claim 1, are incorporated herein by reference.

Further suitable compounds possessing IBAT inhibitory activity have been described in WO 94/24087, WO 98/07749, WO 98/56757, WO 99/32478, WO 99/35135, WO 00/20392, WO 00/20393, WO 00/20410, WO 00/20437, WO 01/34570, WO 00/35889, WO 01/68637, WO 01/68096, WO 02/08211, WO 03/020710, WO 03/022825, WO 03/022830, WO 03/022286, JP 10072371, U.S. Pat. No. 5,070,103, EP 251 315, EP 417 725, EP 489 423, EP 549 967, 25 EP 573 848, EP 624 593, EP 624 594, EP 624 595, EP 869 121 and EP 1 070 703, and the contents of these patent applications, particularly the compounds described in claim 1 and the named examples, are incorporated herein by reference.

Particular classes of IBAT inhibitors suitable for use in the present invention are benzothiepines. Other suitable classes of IBAT inhibitors are the 1,2-benzothiazepines, 1,4-benzothiazepines and/or 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582).

A further suitable compound possessing IBAT inhibitory activity is S-8921 (EP 597 107).

A further suitable IBAT inhibitor is the compound:

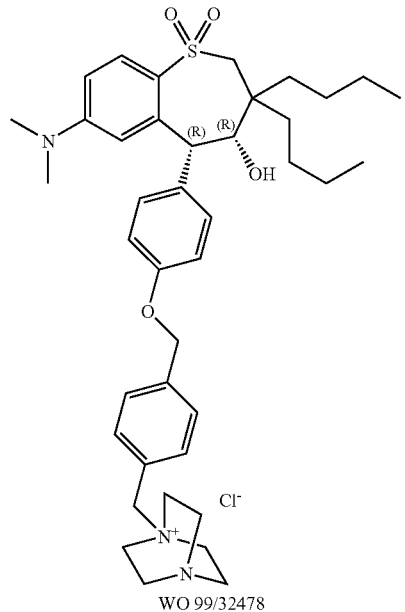

WO 99/32478

Other particular suitable compound possessing IBAT inhibitory activity include:

1,1-dioxo-3,3-dibutyl-5-phenyl-7-methylthio-8-(N-{(R)-1'-phenyl-1'-[N'-(carboxymethyl)carbamoyl]methyl }carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(carboxymethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3-butyl-3-ethyl-5-phenyl-7-methylthio-8-(N-{(R)-1'-phenyl-1'-[N'-(2-sulphoethyl)carbamoyl]methyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-sulphoethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]-4-hydroxybenzyl}carbamoylmethoxy)-2,3,4,5-tetrahydro-1,5-benzothiazepine;

1,1-dioxo-3-butyl-3-ethyl-5-phenyl-7-methylthio-8-(N-{(R)-α-[N'-(5-carboxypentyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(2-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{α-[N'-(2-sulphoethyl)carbamoyl]-2-fluorobenzyl}carbamoylmethoxy)-2,3,4,5-tetrahydro-1,5-benzothiazepine;

1,1 dioxo-3-butyl-3-ethyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-(R)-(2-hydroxy-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{(R)-1-[N''-(R)-(2-hydroxy-1-carboxyethyl)carbamoyl]-2-hydroxyethyl}carbamoyl)benzyl]carbamoylmethoxy}-2,3,4,5-tetrahydro-1,5-benzothiazepine;

1,1-dioxo-3-butyl-3-ethyl-5-phenyl-7-methylthio-8-(N-{α-[N'-(carboxymethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{α-[N'-((ethoxy)(methyl)phosphoryl-methyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-{N-[(R)-α-(N'-{2-[(hydroxy)(methyl)phosphoryl]ethyl}carbamoyl)benzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[N'-(2-methylthio-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-{N-[(R)-α-(N'-{2-[(methyl)(ethyl)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-{N-[(R)-α-(N'-{2-[(methyl)(hydroxy)phosphoryl]ethyl}carbamoyl)-4-hydroxybenzyl]carbamoylmethoxy}-2,3,4,5-tetrahydro-1,5-benzothiazepine;

1,1-dioxo-3,3-dibutyl-5-phenyl-7-methylthio-8-(N-{(R)-α-[(R)-N'-(2-methylsulphinyl-1-carboxyethyl)carbamoyl]benzyl}carbamoylmethoxy)-2,3,4,5-tetrahydro-1,5-benzothiazepine; and 1,1-dioxo-3,3-dibutyl-5-phenyl-7-methoxy-8-[N-{(R)-α-[N'-(2-sulphoethyl)carbamoyl]-4-hydroxybenzyl}carbamoylmethoxy]-2,3,4,5-tetrahydro-1,5-benzothiazepine;

or a pharmaceutically acceptable salt, solvate, solvate of such a salt or a prodrug thereof.

Additional suitable IBAT inhibitors for combination with compounds of the present invention are those described in WO 03/020710. Further suitable compounds possessing IBAT inhibitory activity have the following structure of formula (AI):

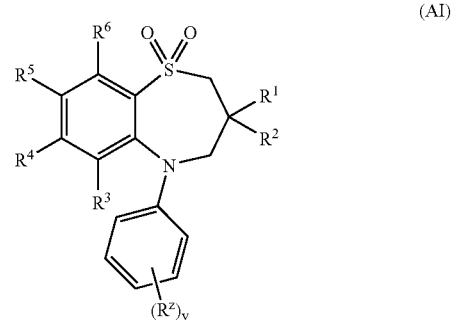

(AI)

wherein:

One of $R^1$ and $R^2$ are selected from hydrogen or $C_{1-6}$alkyl and the other is selected from $C_{1-6}$alkyl;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of $R^4$ and $R^5$ is a group of formula (AIA):

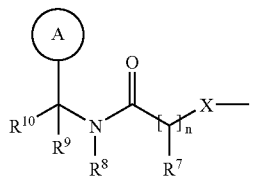

(AIA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^a$ is hydrogen or $C_{1-6}$alkyl and b is 0-2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$alkyl;

$R^9$ is hydrogen or $C_{1-6}$alkyl;

$R^{10}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (AIB):

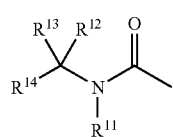

(AIB)

wherein:

$R^{11}$ is hydrogen or $C_{1-6}$alkyl;

$R^{12}$ and $R^{13}$ are independently selected from hydrogen, halo, nitro, cyano, hydroxy, amino, carbamoyl, mercapto, sulphamoyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$-alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (AIC):

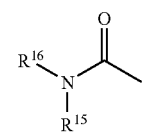

(AIC)

$R^{15}$ is hydrogen or $C_{1-6}$alkyl;

$R^{16}$ is hydrogen or $C_{1-6}$alkyl; wherein $R^{16}$ may be optionally substituted on carbon by one or more groups selected from $R^{31}$;

n is 1-3; wherein the values of $R^7$ may be the same or different;

$R^{17}$, $R^{18}$, $R^{19}$, $R^{23}$, $R^{25}$, $R^{29}$ or $R^{31}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —N$R^{36}$—, —S(O)$_x$—, —N$R^{36}$C(O)N$R^{36}$—, —N$R^{36}$C(S)N$R^{36}$—, —OC(O)N=C—, —N$R^{36}$C(O)— or —C(O)N$R^{36}$-; wherein $R^{36}$ is selected from hydrogen or $C_{1-6}$alkyl, and x is 0-2;

p, q, r and s are independently selected from 0-2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$ or $R^{35}$ are independently selected from $C_{1-6}$alkyl, $C^{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl) carbamoyl, benzyl, benzyloxycarbonyl, benzoyl and phenylsulphonyl; or a pharmaceutically acceptable salt, solvate, solvate of such a salt or a prodrug thereof.

A particular IBAT inhibitor is selected from any one of Examples 1-44 of WO 03/020710, or a pharmaceutically acceptable salt, solvate, solvate of such a salt or a prodrug thereof, and the compounds of Examples 1-44 are incorporated herein by reference. Claims 1-10 of WO 03/020710 are also incorporated herein by reference. A particular IBAT inhibitor selected from WO 03/020710 is selected from any one of:

1,1-dioxo-3,3-dibutyl-5-phenyl-7-methylthio-8-(N-{(R)-α-[N'-(2-(S)-3-(R)-4-(R)-5-(R)-2,3,4,5,6-pentahydroxyhexyl) carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{ (R)-α-[N'-(2-(S)-3-(R)-4-(R)-5-(R)-2,3,4,5,6-pentahydroxyhexyl)carbamoyl]benzyl}carbamoylmethoxy)-2,3,4, 5-tetrahydro-1,5-benzothiazepine;

1,1-dioxo-3-butyl-3-ethyl-5-phenyl-7-methylthio-8-(N-{ (R)-α-[N'-((S)-1-carbamoyl-2-hydroxyethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{ (R)-α-[N'-(hydroxycarbamoyl-methyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-[N-{ (R)-α-{N'-[2-(N'-pyrimidin-2-ylureido)ethyl] carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-[N-((R)-α-{N'-[2-(N'-pyridin-2-ylureido)ethyl] carbamoyl}benzyl)carbamoylmethoxy]-2,3,4,5-tetrahydro-1,5-benzothiazepine;

1,1-dioxo-3-butyl-3-ethyl-5-phenyl-7-methylthio-8-(N-{ (R)-α-[N'-(1-t-butoxycarbonylpiperidin-4-ylmethyl)carbamoyl]benzyl}carbamoylmethoxy)-2,3,4,5-tetrahydro-1,5-benzothiazepine;

1,1-dioxo-3-butyl-3-ethyl-5-phenyl-7-methylthio-8-(N-{ (R)-α-[N'-(2,3-dihydroxypropyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-[N-((R)-α-{N'-[2-(3,4-dihydroxyphenyl)-2-methoxyethyl] carbamoyl}benzyl)carbamoylmethoxy]-2,3,4,5-tetrahydro-1,5-benzothiazepine 1,1-dioxo-3-butyl-3-ethyl-5-phenyl-7-methylthio-8-(N-{ (R)-α-[N'-(2-aminoethyl)carbamoyl] benzyl}carbamoylmethoxy)-2,3,4,5-tetrahydro-1,5-benzothiazepine;

1,1-dioxo-3-butyl-3-ethyl-5-phenyl-7-methylthio-8-(N-{ (R)-α-[N'-(piperidin-4-ylmethyl)carbamoyl] benzyl}carbamoylmethoxy)-2,3,4,5-tetrahydro-1,5-benzothiazepine; or 1,1-dioxo-3-butyl-3-ethyl-5-phenyl-7-methylthio-8-(N-{ (R)-α-[N'-(2-N,N-dimethylaminosulphamoylethyl)carbamoyl]benzyl}carbamoylmethoxy)-2,3,4,5-tetrahydro-1,5-benzothiazepine;

or a pharmaceutically acceptable salt, solvate, solvate of such a salt or a prodrug thereof.

Additional suitable MBAT inhibitors for combination with compounds of the present invention are those described in WO 03/022825. Further suitable compounds possessing IBAT inhibitory activity have the following structure of formula (BI):

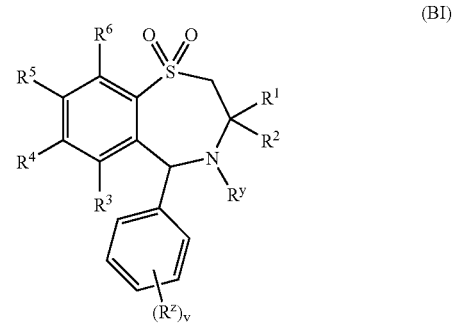

(BI)

wherein:

One of $R^1$ and $R^2$ are selected from hydrogen or $C_{1-6}$alkyl and the other is selected from $C_{1-6}$alkyl;

$R^y$ is selected from hydrogen, hydroxy, $C_{1-6}$alkyl, $C_{1-4}$alkoxy and $C_{1-6}$alkanoyloxy;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N, N-($C_{1-6}$alkyl)$_2$sulphamoyl;

v is 0-5;

one of $R^4$ and $R^5$ is a group of formula (BIA):

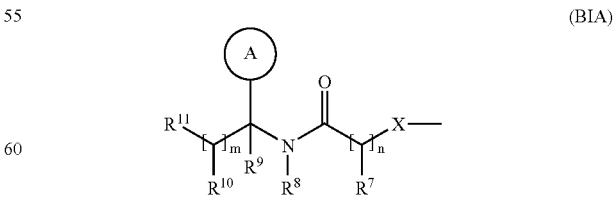

(BIA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0-2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl; or $R^{11}$ is a group of formula (BIB):

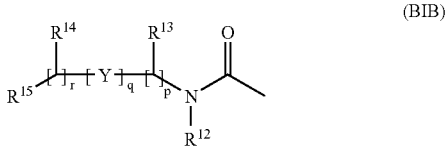

wherein:

Y is —N(R$^x$)—, —N(R$^x$)C(O)—, —O—, and —S(O)$_a$—; wherein a is 0-2 and R$^x$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R)$^e$) or —P(O)(OR$^e$)(R$^f$) wherein R$^e$ and R$^f$ are independently selected from $C_{1-6}$alkyl;

p is 1-3; wherein the values of $R^{13}$ may be the same or different;

q is 0-1;

r is 0-3; wherein the values of $R^{14}$ may be the same or different;

m is 0-2; wherein the values of $R^{10}$ may be the same or different;

n is 1-3; wherein the values of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{16}$, $R^{17}$ and $R^{18}$ may be independently optionally substituted on carbon by one or more $R^{21}$:

$R^{19}$ and $R^{20}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein $R^{19}$ and $R^{20}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

A particular IBAT inhibitor is selected from any one of Examples 1-7 of WO 03/022825, or a pharmaceutically acceptable salt, solvate, solvate of such a salt or a prodrug thereof, and the compounds of Examples 1-7 are incorporated herein by reference. Claims 1-8 of WO 03/022825 are also incorporated herein by reference. A particular IBAT inhibitor selected from WO 03/022825 is selected from any one of:

1,1-dioxo-3(R)-3-butyl-3-ethyl-5-(R)-5-phenyl-8-[N-((R)-α-carboxybenzyl)carbamoylmethoxy]-2,3,4,5-tetrahydro-1,4-benzothiazepine;

1,1-dioxo-3(S)-3-butyl-3-ethyl-5-(S)-5-phenyl-8-[N-(R)-α-carboxybenzyl)carbamoylmethoxy]-2,3,4,5-tetrahydro-1,4-benzothiazepine;

1,1-dioxo-3(R)-3-butyl-3-ethyl-5-(R)-5-phenyl-8-(N-{(R)-α-[N-(carboxymethyl)carbamoyl]benzyl}carbamoylmethoxy)-2,3,4,5-tetrahydro-1,4-benzothiazepine;

1,1-dioxo-3(S)-3-butyl-3-ethyl-5-(S)-5-phenyl-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-bromo-8-(N-{(R)-α-[N-(carboxymethyl)carbamoyl]benzyl)}carbamoylmethoxy)-2,3,4,5-tetrahydro-1,4-benzothiazepine;

3,5-trans-1,1-dioxo-3-(S)-3ethyl-3-butyl-4-hydroxy-5-(S)-5-phenyl-7-bromo-8-(N-{(R)-α-[N-(carboxymethyl)carbamoyl]benzyl}carbamoylmethoxy)-2,3,4,5-tetrahydro-1,4-benzothiazepine 3,5-trans-1,1-dioxo-3-(R)-3-ethyl-3-butyl-4-hydroxy-5-(R)-5-phenyl-7-bromo-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(carboxymethyl)carbamoyl]benzyl}carbamoylmethoxy)-2,3,4,5-tetrahydro-1,4-benzothiazepine;

3,5-trans-1,1-dioxo-3-ethyl-3-butyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,4-benzothiazepine ammonia salt;

1,1-dioxo-3-(S)-3-ethyl-3-butyl-5-(S)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt; and 1,1-dioxo-3-(R)-3-ethyl-3-butyl-5-(R)-5-phenyl-7-methylthio-8-(N-{(R)-α-[N-(carboxymethyl)carbamoyl]benzyl}carbamoylmethoxy)-2,3,4,5-tetrahydro-1,4-benzothiazepine diethylamine salt;

or a pharmaceutically acceptable salt, solvate, solvate of such a salt or a prodrug thereof.

Additional suitable IBAT inhibitors for combination with compounds of the present invention are those described in WO 03/022830. Further suitable compounds possessing IBAT inhibitory activity have the following structure of formula (CI):

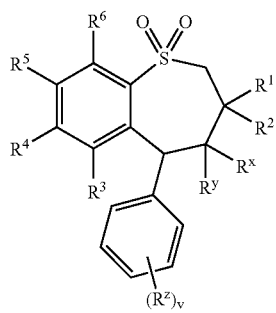

(CI)

wherein:

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$-alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of $R^4$ and $R^5$ is a group of formula (CIA):

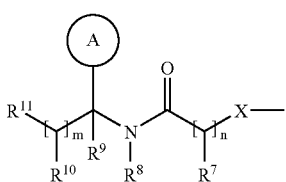

(CIA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, C2-4alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^3$ and $R^6$ and the other of $R^4$ and $R^5$ may be optionally substituted on carbon by one or more $R^{16}$;

X is —O—, —N($R^a$)—, —S(O)$_b$— or —CH($R^a$)—; wherein $R^a$ is hydrogen or $C_{1-6}$alkyl and b is 0-2;

Ring A is aryl or heteroaryl; wherein Ring A is optionally substituted by one or more substituents selected from $R^{17}$;

$R^7$ is hydrogen, $C_{1-4}$alkyl, carbocyclyl or heterocyclyl; wherein $R^7$ is optionally substituted by one or more substituents selected from $R^{18}$;

$R^8$ is hydrogen or $C_{1-4}$alkyl;

$R^9$ is hydrogen or $C_{1-4}$alkyl;

$R^{10}$ is hydrogen, $C_{1-4}$alkyl, carbocyclyl or heterocyclyl; wherein $R^{10}$ is optionally substituted by one or more substituents selected from $R^{19}$;

$R^{11}$ is carboxy, sulpho, sulphino, phosphono, —P(O)(O$R^c$)(O$R^d$), —P(O)(OH)(O$R^c$), —P(O)(OH)($R^d$) or —P(O)(O$R^c$)($R^d$) wherein $R^c$ and $R^d$ are independently selected from $C_{1-6}$alkyl; or $R^{11}$ is a group of formula (CIB):

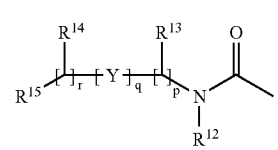

(CIB)

wherein:

Y is —N(R″)—, —N(R″)C(O)—, —O—, and —S(O)$_a$—; wherein a is 0-2 and R″ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; wherein $R^{13}$ and $R^{14}$ may be independently optionally substituted by one or more substituents selected from $R^{20}$;

$R^{15}$ is carboxy, sulpho, sulphino, phosphono, —P(O)(O$R^e$)(O$R^f$), —P(O)(OH)(O$R^e$), —P(O)(OH)($R^e$) or —P(O)(O$R^e$)($R^f$) wherein $R^e$ and $R^f$ are independently selected from $C_{1-6}$alkyl;

p is 1-3; wherein the values of $R^{13}$ may be the same or different;

q is 0-1;

r is 0-3; wherein the values of $R^{14}$ may be the same or different;

m is 0-2; wherein the values of $R^{10}$ may be the same or different;

n is 1-3; wherein the values of $R^7$ may be the same or different;

$R^{16}$, $R^{17}$ and $R^{18}$ are independently selected from halo, nitro, cyano, hydroxy, amino, carboxy, carbamoyl, mercapto, sulphamoyl, $C^{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{16}$, $R^{17}$ and $R^{18}$ may be independently optionally substituted on carbon by one or more $R^{21}$;

$R^{19}$ and $R^{20}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl, N,N-($C_{1-4}$alkyl)$_2$sulphamoyl, carbocyclyl, heterocyclyl, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from $C_{1-6}$alkyl; wherein R$^{19}$ and R$^{20}$ may be independently optionally substituted on carbon by one or more R$^{22}$;

R$^{21}$ and R$^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

or a pharmaceutically acceptable salt, solvate, solvate of such a salt or a prodrug thereof.

A particular IBAT inhibitor is selected from any one of Examples 1-4 of WO 03/022830, or a pharmaceutically acceptable salt, solvate, solvate of such a salt or a prodrug thereof, and the compounds of Examples 1-4 are incorporated herein by reference. Claims 1-8 of WO 03/022830 are also incorporated herein by reference. A particular IBAT inhibitor selected from WO 03/022830 is selected from any one of:

1,1-dioxo-3-butyl-3-ethyl-4-hydroxy-5-phenyl-7-(N-{(R)-α-[N-(carboxymethyl)carbamoyl]benzyl}carbamoylmethylthio)-2,3,4,5-tetrahydrobenzothiepine 1,1-dioxo-3-butyl-3-ethyl-4-hydroxy-5-phenyl-7-(N-{(R)-α-[N-(2-sulphoethyl)carbamoyl]-4-hydroxybenzyl}carbamoylmethylthio)-2,3,4,5-tetrahydrobenzothiepine ammonia salt 1,1-dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine; and 1,1-dioxo-3-butyl-3-ethyl-4-hydroxy-5-phenyl-7-{(N-[1-(carboxy)-1-(thien-2-yl)methyl]carbamoylmethylthio}-2,3,4,5-tetrahydrobenzothiepine or a pharmaceutically acceptable salt, solvate, solvate of such a salt or a prodrug thereof.

Additional suitable IBAT inhibitors for combination with compounds of the present invention are those described in WO 03/022286. Further suitable compounds possessing IBAT inhibitory activity have the following structure of formula (DI):

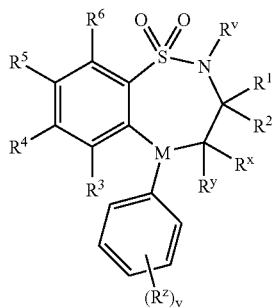

(DI)

wherein:

R$^v$ is selected from hydrogen or $C_{1-6}$alkyl;

One of R$^1$ and R$^2$ are selected from hydrogen or $C_{1-6}$alkyl and the other is selected from $C_{1-6}$alkyl;

R$^x$ and R$^y$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

M is selected from —N— or —CH—;

R$^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of R$^4$ and R$^5$ is a group of formula (DIA):

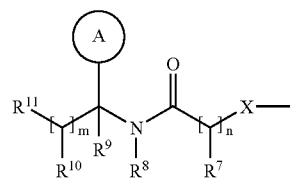

(DIA)

R$^3$ and R$^6$ and the other of R$^4$ and R$^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein R$^3$ and R$^6$ and the other of R$^4$ and R$^5$ may be optionally substituted on carbon by one or more R$^{16}$.

X is —O—, —N(R$^a$)—, —S(O)$_b$— or —CH(R$^a$)—; wherein R$^a$ is hydrogen or $C_{1-6}$alkyl and b is 0-2;

Ring A is aryl or heteroaryl; wherein Ring A is optionally substituted by one or more substituents selected from R$^{17}$;

R$^7$ is hydrogen, $C_{1-4}$alkyl, carbocyclyl or heterocyclyl; wherein R$^7$ is optionally substituted by one or more substituents selected from R$^{18}$;

R$^8$ is hydrogen or $C_{1-4}$alkyl;

R$^9$ is hydrogen or $C_{1-4}$alkyl;

R$^{10}$ is hydrogen, $C_{1-4}$alkyl, carbocyclyl or heterocyclyl; wherein R$^{10}$ is optionally substituted by one or more substituents selected from R$^{19}$;

R$^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$allyl; or R$^{11}$ is a group of formula (DIB) or (DIC):

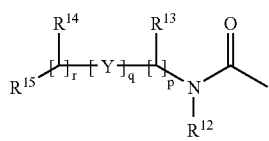

(DIB)

-continued

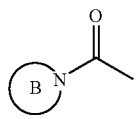
(DIC)

wherein:

Y is —N($R^a$)—, —N($R^a$)C(O)—, —N($R^a$)C(O)(CR$^s$R$^t$)$_v$N(R$^n$)C(O)—, —O—, and S(O)$_a$—; wherein a is 0-2, v is 1-2, R$^s$ and R$^t$ are independently selected from hydrogen or C$_{1-4}$alkyl optionally substituted by R$^{26}$ and R$^n$ is hydrogen or C$_{1-4}$alkyl;

$R^{12}$ is hydrogen or C$_{1-4}$alkyl;

$R^{13}$ and $R^{14}$ are independently selected from hydrogen, C$_{1-4}$alkyl, carbocyclyl or heterocyclyl; and when q is 0, $R^{14}$ may additionally be selected from hydroxy; wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$)(wherein R$^e$ and R$^f$ are independently selected from C$_{1-6}$alkyl;

p is 1-3; wherein the values of $R^{13}$ may be the same or different;

q is 0-1;

r is 0-3; wherein the values of $R^{14}$ may be the same or different;

m is 0-2; wherein the values of $R^{10}$ may be the same or different;

n is 1-3; wherein the values of $R^7$ may be the same or different;

Ring B is a nitrogen linked heterocyclyl substituted on carbon by one group selected from $R^{23}$, and optionally additionally substituted on carbon by one or more $R^{24}$; and wherein if said nitrogen linked heterocyclyl contains an —NH— moiety, that nitrogen may be optionally substituted by a group selected from $R^{25}$;

$R^{16}$, $R^{17}$ and $R^{18}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, C$_{1-4}$alkanoylamino, N-(C$_{1-4}$alkyl)carbamoyl, N,N-(C$_{1-4}$alkyl)$_2$carbamoyl, C$_{1-4}$alkylS(O)$_a$ wherein a is 0 to 2, C$_{1-4}$alkoxycarbonyl, N-(C$_{1-4}$alkyl)sulphamoyl and N,N-(C$_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{24}$ and $R^{26}$ are independently selected from halo, nitro, cyano, hydroxy, amino, carboxy, carbamoyl, mercapto, sulphamoyl, C$_{1-4}$alkyl, C$_{2-4}$alkenyl, C$_{2-4}$alkynyl, C$_{1-4}$alkoxy, C$_{1-4}$alkanoyl, C$_{1-4}$alkanoyloxy, N-(C$_{1-4}$alkyl)amino, N,N-(C$_{1-4}$alkyl)$_2$amino, C$_{1-4}$alkanoylamino, N-(C$_{1-4}$alkyl)carbamoyl, N,N-(C$_{1-4}$alkyl)$_2$carbamoyl, C$_{1-4}$alkylS(O)$_a$ wherein a is 0 to 2, C$_{1-4}$alkoxycarbonyl, N-(C$_{1-4}$alkyl)sulphamoyl, N,N-(C$_{1-4}$alkyl)$_2$sulphamoyl, carbocyclyl, heterocyclyl, benzyloxycarbonylamino, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein R$^a$ and R$^b$ are independently selected from C$_{1-6}$alkyl; wherein $R^{19}$, $R^{20}$, $R^{24}$ and $R^{26}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{23}$ is carboxy, sulpho, sulphino, phosphono, —P(O)(OR$^g$)(OR$^h$), —P(O)(OH)(OR$^g$), —P(O)(OH)(R$^g$) or —P(O)(OR$^g$)(R$^h$) wherein R$^g$ and R$^h$ are independently selected from C$_{1-6}$alkyl;

$R^{25}$ is selected from C$_{1-6}$alkyl, C$_{1-6}$alkanoyl, C$_{1-6}$alkylsulphonyl, C$_{1-6}$-alkoxycarbonyl, carbamoyl, N-(C$_{1-6}$alkyl)carbamoyl, N,N-(C$_{1-6}$alkyl)carbamoyl, benzyl, benzyloxycarbonyl, benzoyl and phenylsulphonyl;

or a pharmaceutically acceptable salt, solvate, solvate of such a salt or a prodrug thereof.

A particular IBAT inhibitor is selected from any one of Examples 1-39 of WO 03/022286, or a pharmaceutically acceptable salt, solvate, solvate of such a salt or a prodrug thereof, and the compounds of Examples 1-39 are incorporated herein by reference. Claims 1-10 of WO 03/022286 are also incorporated herein by reference. A particular MBAT inhibitor selected from WO 03/022286 is selected from any one of:

1,1-dioxo-3,3-dibutyl-5-phenyl-7-methylthio-8-(N-{(R)-α-[N-((R)-1-carboxy-2-methylthio-ethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-(R)-hydroxypropyl)carbamoyl]-4hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]-4-hydroxybenzyl }carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxybutyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]benzyl}carbamoylmethoxy)-2,3,4,5-tetrahydro-1,2,5-benzothiadiazepine;

1,1dioxo-3,3-dibutyl-5-phenyl-7-methylthio-8-(N-{(R)-α-[N-((S)-1-carboxy-2-(R)-hydroxypropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-(2-sulphoethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxyethyl)carbamoyl]-4-hydroxybenzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((R)-1-carboxy-2-methylthioethyl)carbamoyl]benzyl}carbamoylmethoxy)-2,3,4,5-tetrahydro-1,2,5-benzothiadiazepine;

1,1-dioxo-3,3dibutyl-5-phenyl-7-methylthio-8-(N-{(R)-α-[N-{(S)-1-[N-((S)-2-hydroxy-1-carboxyethyl)carbamoyl]propyl}carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxy-2-methylpropyl)carbamoyl]benzyl}carbamoylmethoxy)-2,3,4,5-tetrahydro-1,2,5-benzothiadiazepine;

1,1-dioxo-3,3-dibutyl-5-phenyl-7-methylthio-8-(N-{(R)-α-[N-((S)-1-carboxypropyl)carbamoyl]-4-hydroxybenzyl}carbamoylmethoxy)-2,3,4,5-tetrahydro-1,2,5-benzothiadiazepine; and 1,1dioxo-3,3-dibutyl-5-phenyl-7-methylthio-8-[N-((R)-α-carboxy-4-hydroxybenzyl)carbamoylmethoxy]-2,3,4,5-tetrahydro-1,2,5-benzothiadiazepine; or a pharmaceutically acceptable salt, solvate, solvate of such a salt or a prodrug thereof.

Further suitable compounds possessing IBAT inhibitory activity have the following structure of formula (EI):

(EI)

wherein:

$R^v$ is selected from hydrogen or $C_{1-6}$alkyl;

One of $R^1$ and $R^2$ are selected from hydrogen or $C_{1-6}$alkyl and the other is selected from $C_{1-6}$alkyl;

$R^x$ and $R^y$ are independently selected from hydrogen, hydroxy, amino, mercapto, $C_{1-6}$alkyl, $C_{1-6}$-alkoxy, N-($C_{1-6}$alkyl)amino, N,N-($C_{1-6}$alkyl)$_2$amino, $C_{1-6}$alkylS(O), wherein a is to 2;

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

v is 0-5;

one of $R^4$ and $R^5$ is a group of formula (EIA):

(EIA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$-alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl; wherein $R^3$ and $R^6$ and the other of $R^4$ and $R^5$ may be optionally substituted on carbon by one or more $R^{17}$;

X is —O—, —N($R^a$)—, —S(O)$_b$— or —CH($R^a$)—; wherein $R^a$ is hydrogen or $C_{1-6}$alkyl and b is 0-2;

Ring A is aryl or heteroaryl; wherein Ring A is optionally substituted on carbon by one or more substituents selected from $R^{18}$;

$R^7$ is hydrogen, $C_{1-6}$alkyl, carbocyclyl or heterocyclyl; wherein $R^7$ is optionally substituted on carbon by one or more substituents selected from $R^{19}$; and wherein if said heterocyclyl contains an —NH— group, that nitrogen may be optionally substituted by a group selected from $R^{20}$;

$R^8$ is hydrogen or $C_{1-6}$alkyl;

$R^9$ is hydrogen or $C_{1-6}$alkyl;

$R^{10}$ is hydrogen, halo, nitro, cyano, hydroxy, amino, carbamoyl, mercapto, sulphamoyl, hydroxyaminocarbonyl, $C_{1-6}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{21}$—($C_{1-10}$alkylene)$_q$- or heterocyclyl-($C_{1-10}$alkylene)$_r$-$R^{22}$—($C_{1-10}$alkylene)$_s$-; wherein $R^{10}$ is optionally substituted on carbon by one or more substituents selected from $R^{23}$; and wherein if said heterocyclyl contains an —NH— group, that nitrogen may be optionally substituted by a group selected from $R^{24}$; or $R^{10}$ is a group of formula (EIB):

(EIB)

wherein:

$R^{11}$ is hydrogen or $C_{1-6}$alkyl;

$R^{12}$ and $R^{13}$ are independently selected from hydrogen, halo, carbamoyl, sulphamoyl, $C_{1-10}$alkyl, $C_{2-10}$-alkenyl, $C_{2-10}$-alkynyl, $C_{1-10}$alkanoyl, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$ sulphamoylamino, carbocyclyl or heterocyclyl; wherein $R^{12}$ and $R^{13}$ may be independently optionally substituted on carbon by one or more substituents selected from $R^{25}$; and wherein if said heterocyclyl contains an —NH— group, that nitrogen may be optionally substituted by a group selected from $R^{26}$;

$R^{14}$ is selected from hydrogen, halo, carbamoyl, sulphamoyl, hydroxyaminocarbonyl, $C_{1-10}$alkyl, $C_{2-10}$-alkenyl, $C_{2-10}$alkynyl, $C_{1-10}$alkanoyl, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{27}$—($C_{1-10}$alkylene)$_q$- or heterocyclyl-($C_{1-10}$alkylene)$_r$-$R^{28}$—($C_{1-10}$alkylene)$_s$-; wherein $R^{14}$ may be optionally substituted on carbon by one or more substituents selected from $R^{29}$; and wherein if said heterocyclyl contains an —NH— group, that nitrogen may be optionally substituted by a group selected from $R^{30}$; or $R^{14}$ is a group of formula (EIC):

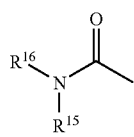

(EIC)

$R^{15}$ is hydrogen or $C_{1-6}$alkyl;

$R^{16}$ is hydrogen or $C_{1-6}$alkyl; wherein $R^{16}$ may be optionally substituted on carbon by one or more groups selected from $R^{31}$;

n is 1-3; wherein the values of $R^7$ may be the same or different;

$R^{17}$, $R^{18}$, $R^{19}$, $R^{23}$, $R^{25}$, $R^{29}$ or $R^{31}$ are independently selected from halo, nitro, cyano, hydroxy, amino, carbamoyl, mercapto, sulphamoyl, hydroxyaminocarbonyl, $C_{1-10}$alkyl, $C_{2-10}$-alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$ amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_p$-$R^{32}$—($C_{1-10}$alkylene)$_q$- or heterocyclyl-($C_{1-10}$alkylene)$_r$-$R^{33}$—($C_{1-10}$alkylene)$_s$-; wherein $R^{17}$, $R^{18}$, $R^{19}$, $R^{23}$, $R^{25}$, $R^{29}$ or $R^{31}$ may be independently optionally substituted on carbon by one or more $R^{34}$; and wherein if said heterocyclyl contains an —NH— group, that nitrogen may be optionally substituted by a group selected from $R^{35}$;

$R^{21}$, $R^{22}$, $R^{27}$, $R^{28}$, $R^{32}$ or $R^{33}$ are independently selected from —O—, —NR$^{36}$—, —S(O)$_x$—, —NR$^{36}$C(O)NR$^{36}$—, —NR$^{36}$C(S)NR$^{36}$—, —OC(O)N=C—, —NR$^{36}$C(O)— or —C(O)NR$^{36}$—; wherein $R^{36}$ is selected from hydrogen or $C_{1-6}$alkyl, and x is 0-2;

p, q, r and s are independently selected from 0-2;

$R^{34}$ is selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl, N,N-dimethylsulphamoyl, N-methylsulphamoylamino and N,N-dimethylsulphamoylamino;

$R^{20}$, $R^{24}$, $R^{26}$, $R^{30}$ or $R^{35}$ are independently selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C^{1-6}$alkyl) carbamoyl, benzyl, benzyloxycarbonyl, benzoyl and phenylsulphonyl;

or a pharmaceutically acceptable salt, solvate, solvate of such a salt or a prodrug thereof.

Suitable IBAT inhibitors having the above structure are selected from any one of:

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl) carbamoyl]benzyl}carbamoylmethoxy)-2,3,4,5-tetrahydro-1,2,5-benzothiadiazepine;

1,1-Dioxo-3,3-dibutyl-5-phenyl-7-methylthio-8-(N-{(R)-α-[N-(2-(S)-3-(R)-4-(R)-5-(R)-2,3,4,5,6-pentahydroxyhexyl) carbamoyl]-4-hydroxybenzyl}carbamoylmethoxy)-2,3,4,5-tetrahydro-1,2,5-benzothiadiazepine;

1,1-Dioxo-3,3-dibutyl-5-phenyl-7-methylthio-8-[N-((R/S)-α-{N-[1-(R)-2-(S)-1-hydroxy-1-(3,4-dihydroxyphenyl) prop-2-yl]carbamoyl}benzyl)carbamoylmethoxy]-2,3,4,5-tetrahydro-1,2,5-benzothiadiazepine (both enantiomers);

1,1-Dioxo-3,3-dibutyl-5-phenyl-7-methylthio-8-{N-[(R)-α-(N-{2-(S)-[N-(carbamoylmethyl)carbamoyl]pyrrolidin-1-ylcarbonylmethyl}carbamoyl)benzyl]carbamoylmethoxy}-2,3,4,5-tetrahydro-1,2,5-benzothiadiazepine;

1,1-Dioxo-3,3-dibutyl-5-phenyl-7-methylthio-8-[N-((R)-α-{N-[2-(3,4,5-trihydroxyphenyl)ethyl]carbamoyl}benzyl) carbamoylmethoxy]-2,3,4,5-tetrahydro-1,2,5-benzothiadiazepine; or 1,1-Dioxo-3,3-dibutyl-5-phenyl-7-methylthio-8-(N-{(R)-α-[N-(2-(R)-3-(S)4-(S)-5-(R)-3,4,5,6-tetrahydroxytetrahydropyran-2-ylmethyl)carbamoyl]benzyl}carbamoylmethoxy)-2,3,4,5-tetrahydro-1,2,5-benzothiadiazepine;

or a pharmaceutically acceptable salt, solvate, solvate of such a salt or a prodrug thereof.

Further suitable compounds possessing IBAT inhibitory activity have the following structure of formula (FI):

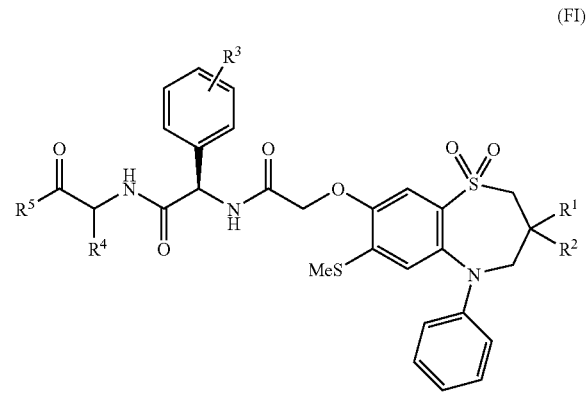

(FI)

wherein:

R¹ and R² are independently selected from $C_{1-4}$alkyl;

R³ is hydrogen, hydroxy or halo;

R⁴ is $C_{1-4}$alkyl optionally substituted by hydroxy, methoxy and methylS(O)$_a$ wherein a is 0-2

R⁵ is hydroxy or HOC(O)CH(R⁶)NH—;

R⁶ is selected from hydrogen and $C_{1-3}$alkyl optionally substituted by hydroxy, methoxy and methylS(O)$_a$ wherein a is 0-2;

or a pharmaceutically acceptable salt, solvate, solvate of such a salt or a prodrug thereof; with the proviso that when R¹ and R² are both butyl, R⁵ is hydroxy and R⁴ is methylthiomethyl, methylsulphinylmethyl, methylthiomethyl, hydroxymethyl, methoxymethyl; R³ is not hydrogen; and with the proviso that when R¹ and R² are both butyl, R⁵ is HOC(O)CH(R⁶)NH—, R⁶ is hydroxymethyl and R⁴ is hydroxymethyl; R³ is not hydrogen.

Suitable IBAT inhibitors having the above structure are selected from any one of:

1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N!-((S)-1-carboxybutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylbutyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]benzyl}carbamoylmethoxy)-2,3,4,5-tetrahydro-1,5-benzothiazepine;

1,1-oxo-3,3-dibutyl-5-phenyl-7-methylthio-8-(N-{(R)-α-[N'-((S)-1-carboxy-3-methylsulphonylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]benzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxyethyl)carbamoyl]4hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxybutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'((S)-1-carboxy-3-methylbutyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-hydroxypropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methylthioethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'((S)-1-carboxy-2-methylsulphinylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-mesylethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-2-methoxyethyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylthiopropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-methylsulphonylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxy-3-mesylpropyl)carbamoyl]-4-hydroxybenzyl}carbamoylmethoxy)-2,3,4,5-tetrahydro-1,5-benzothiazepine;

1,1-dioxo-3,3-dibutyl-5-phenyl-7-methylthio-8-(N-{(R)-α-[N'-((S)-1-carboxypropyl)carbamoyl]-4-hydroxybenzyl}carbamoylmethoxy)-2,3,4,5-tetrahydro-1,5-benzothiazepine; or 1,1-dioxo-3,3-dibutyl-5-phenyl-7-methylthio-8-(N-{(R)-α-[N'-((S)-1-carboxyethyl)carbamoyl]benzyl}carbamoylmethoxy)-2,3,4,5-tetrahydro-1,5-benzothiazepine.

or a pharmaceutically acceptable salt, solvate, solvate of such a salt or a prodrug thereof.

Further suitable BAT inhibitors are those having the structure (GI):

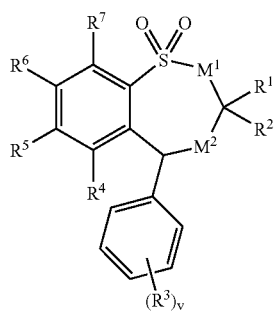

(GI)

wherein $M^1$ is —CH$_2$— or —NR$^{21}$—;

$M^2$ is —CR$^{22}$R$^{23}$— or —NR$^{24}$—; provided that if $M^1$ is —NR$^{21}$-, $M^2$ is —CR$^{22}$R$^{23}$—;

One of $R^1$ and $R^2$ are selected from hydrogen, $C_{1-6}$alkyl or $C_{2-6}$alkenyl and the other is selected from $C_{1-6}$alkyl or $C_{2-6}$alkenyl;

$R^3$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$-alkoxycarbonyl, N-($C_{1-6}$alkyl)sulphamoyl and N,N-($C_{1-6}$alkyl)$_2$sulphamoyl;

v is 0-5;

one of $R^5$ and $R^6$ is a group of formula (GIA):

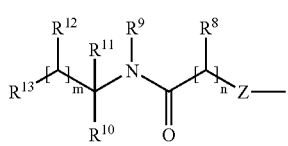

(GIA)

$R^4$ and $R^7$ and the other of $R^5$ and $R^6$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O)$_a$ wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^4$ and $R^7$ and the other of $R^5$ and $R^6$ may be optionally substituted on carbon by one or more $R^{25}$;

Z is —O—, —N($R^a$)—, —S(O)$_b$— or —CH($R^a$)—; wherein $R^a$ is hydrogen or $C_{1-6}$alkyl and b is 0-2;

$R^8$ is hydrogen, $C_{1-4}$alkyl, carbocyclyl or heterocyclyl; wherein $R^8$ may be optionally substituted on carbon by one or more substituents selected from $R^{26}$; and wherein if said heterocyclyl contains an —NH— group, that nitrogen may be optionally substituted by a group selected from $R^{27}$;

$R^9$ is hydrogen or $C_{1-4}$alkyl;

$R^{10}$ and $R^{11}$ are independently selected from hydrogen, $C_{1-4}$alkyl, carbocyclyl or heterocyclyl; or $R^{10}$ and $R^{11}$ together form $C_{2-6}$alkylene; wherein $R^{10}$ and $R^{11}$ or $R^{10}$ and $R^{11}$ together may be independently optionally substituted on carbon by one or more substituents selected from $R^{28}$; and wherein if said heterocyclyl contains an —NH— moiety, that nitrogen may be optionally substituted by one or more $R^{29}$;

$R^{12}$ is hydrogen, $C_{1-4}$alkyl, carbocyclyl or heterocyclyl; wherein $R^{12}$ may be optionally substituted on carbon by one or more substituents selected from $R^{30}$; and wherein if said heterocyclyl contains an —NH— moiety, that nitrogen may be optionally substituted by one or more $R^{31}$;

$R^{13}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$ alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{32}$—($C_{1-10}$alkylene)$_f$- or heterocyclyl-($C_{1-10}$alkylene)$_g$-$R^{33}$—($C_{1-10}$alkylene)$_h$-; wherein $R^{13}$ may be optionally substituted on carbon by one or more substituents selected from $R^{36}$; and wherein if said heterocyclyl contains an —NH— group, that nitrogen may be optionally substituted by a group selected from $R^{37}$; or $R^{13}$ is a group of formula (GIB):

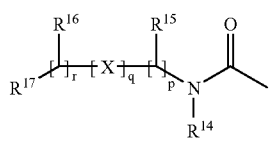

(GIB)

wherein:

X is —N($R^{38}$)—, —N($R^{38}$)C(O)—, —O—, and —S(O)$_a$—; wherein a is 0-2 and $R^{38}$ is hydrogen or $C_{1-4}$alkyl;

$R^{14}$ is hydrogen or $C_{1-4}$alkyl;

$R^{15}$ and $R^{16}$ are independently selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl or heterocyclic group; wherein $R^{15}$ and $R^{16}$ may be independently optionally substituted on carbon by one or more substituents selected from $R^{41}$; and wherein if said heterocyclyl contains an —NH— group, that nitrogen may be optionally substituted by a group selected from $R^{42}$;

$R^{17}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, $C_{1-10}$alkoxycarbonyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{43}$—($C_{1-10}$alkylene)$_f$- or heterocyclyl-($C_{1-10}$alkylene)$_g$-$R^{44}$—($C_{1-10}$alkylene)$_h$-; wherein $R^{17}$ may be optionally substituted on carbon by one or more substituents selected from $R^{47}$; and wherein if said heterocyclyl contains an —NH— group, that nitrogen may be optionally substituted by a group selected from $R^{48}$; or $R^{17}$ is a group of formula (GIC):

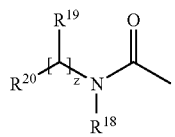

(GIC)

wherein:

$R^{18}$ is selected from hydrogen or $C_{1-4}$alkyl;

$R^{19}$ is selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl or heterocyclic group; where $R^{19}$ may be independently optionally substituted on carbon by one or more substituents selected from $R^{15}$; and wherein if said heterocyclyl contains an —NH— group, that nitrogen may be optionally substituted by a group selected from $R^{52}$;

$R^{20}$ is selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{53}$—($C_{1-10}$alkylene)$_f$- or heterocyclyl-($C_{1-10}$alkylene)$_g$-$R^{54}$—($C_{1-10}$alkylene)$_h$-; wherein $R^{20}$ may be independently optionally substituted on carbon by one or more $R^{57}$; and wherein if said heterocyclyl contains an —NH— group, that nitrogen may be optionally substituted by a group selected from $R^{58}$;

p is 1-3; wherein the values of $R^{15}$ may be the same or different;

q is 0-1;

r is 0-3; wherein the values of $R^{16}$ may be the same or different;

m is 0-2; wherein the values of $R^{12}$ may be the same or different;

n is 1-2; wherein the values of $R^8$ may be the same or different;

z is 0-3; wherein the values of $R^{19}$ may be the same or different;

$R^{21}$ is selected from hydrogen or $C_{1-6}$alkyl;

$R^{22}$ and $R^{23}$ are independently selected from hydrogen, hydroxy, amino, mercapto, $C_{1-6}$alkyl, $C_{1-6}$alkoxy, N-($C_{1-6}$alkyl)amino, N,N-($C_{1-6}$alkyl)$_2$amino, $C_{1-6}$alkylS(O)$_a$ wherein a is 0 to 2;

$R^{24}$ is selected from hydrogen, hydroxy, $C_{1-6}$alkyl, $C_{1-4}$alkoxy and $C_{1-6}$alkanoyloxy;

$R^{25}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, $C_{1-4}$alkanoylamino, N-($C_{1-4}$alkyl)carbamoyl, N,N-($C_{1-4}$alkyl)$_2$carbamoyl, $C_{1-4}$alkylS(O), wherein a is 0 to 2, $C_{1-4}$alkoxycarbonyl, N-($C_{1-4}$alkyl)sulphamoyl and N,N-($C_{1-4}$alkyl)$_2$sulphamoyl; wherein $R^{25}$, may be independently optionally substituted on carbon by one or more $R^{67}$;

$R^{26}$, $R^{28}$, $R^{30}$, $R^{36}$, $R^{41}$, $R^{47}$, $R^{51}$ and $R^{57}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, $C_{1-10}$alkoxycarbonyl, N-($C_{1-10}$alkyl)amino, N,N-($C_{1-10}$alkyl)$_2$amino, N,N,N-($C_{1-10}$alkyl)$_3$ammonio, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclic group, heterocyclyl $C_{1-10}$alkyl, carbocyclyl-($C_{1-10}$alkylene)$_e$-$R^{59}$—($C_{1-10}$alkylene)$_f$- or heterocyclyl-($C_{1-10}$alkylene)$_g$-$R^{60}$-($C_{1-10}$alkylene)$_h$-; wherein $R^{26}$, $R^{28}$, $R^{30}$, $R^{36}$, $R^{41}$, $R^{47}$, $R^{51}$ and $R^{57}$ may be independently optionally substituted on carbon by one or more $R^{63}$; and wherein if said heterocyclyl contains an —NH— group, that nitrogen may be optionally substituted by a group selected from $R^{64}$;

$R^{27}$, $R^{29}$, $R^{31}$, $R^{37}$, $R^{42}$, $R^{48}$, $R^{52}$, $R^{58}$ and $R^{64}$ are independently selected from $C_{1-6}$alkyl, $C_{1-6}$alkanoyl, $C_{1-6}$alkylsulphonyl, sulphamoyl, N-($C_{1-6}$alkyl)sulphamoyl, N,N-($C_{1-6}$alkyl)$_2$sulphamoyl, $C_{1-6}$alkoxycarbonyl, carbamoyl, N-($C_{1-6}$alkyl)carbamoyl, N,N-($C_{1-6}$alkyl)$_2$carbamoyl, benzyl, phenethyl, benzoyl, phenylsulphonyl and phenyl;

$R^{32}$, $R^{33}$, $R^{43}$, $R^{44}$, $R^{53}$, $R^{54}$, $R^{59}$ and $R^{60}$ are independently selected from —O—, —NR$^{65}$—, —S(O)$_x$—, —NR$^{65}$C(O)NR$^{66}$—, —NR$^{65}$C(S)NR$^{66}$—, —OC(O)N=C—, —NR$^{65}$C(O)— or —C(O)NR$^{65}$-; wherein $R^{65}$ and $R^{66}$ are independently selected from hydrogen or $C_{1-6}$alkyl, and x is 0-2;

$R^{63}$ and $R^{67}$ re independently selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2;

or a pharmaceutically acceptable salt, solvate, solvate of such a salt or a prodrug thereof.

Additional suitable IBAT inhibitors having the above structure are selected from any one of:

(+/−)-trans-1,1-dioxo-3-ethyl-3-butyl-5-phenyl-7-methylthio-8-(N-{R)-α-[N'-(2-(S)-3-(R)-4-(R)-5-(R)-2,3,4,5,6- pentahydroxyhexyl)carbamoyl]benzyl}carbamoylmethoxy)-2,3,4,5-tetrahydro-1,4-benzothiazepine;

(+/−)-trans-1,1-dioxo-3-ethyl-3-butyl-5-phenyl-7-methylthio-8-(N-{R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4benzothiazepine;

1,1-dioxo-3-ethyl-3-butyl-4-hydroxy-5-phenyl-7-(N-{α-[N'-(2-(S)-3-(R)-4-(R)-5-(R)-2,3,4,5,6-pentahydroxyhexyl)carbamoyl]-2-fluorobenzyl}carbamoylmethylthio)-2,3,4,5-tetrahydrobenzothiapine; or 1,1-dioxo-3-butyl-3-ethyl-4-hydroxy-5-phenyl-7-(N-{1-[N'-(2-(S)-3-(R)-4-(R)-5-(R)-2,3,4,5,6-pentahydroxyhexyl)carbamoyl]-1-(cyclohexyl)methyl}carbamoylmethylthio)-2,3,4,5-tetrahydrobenzothiepine.

Compounds of formula (AI), (BI), (CI), (DI), (EI), (FI) and (GI) or a pharmaceutically acceptable salt, solvate, solvate of such a salt or a prodrug thereof may be prepared by processes known in the art.

In a particular aspect of the invention an IBAT inhibitor or a pharmaceutically acceptable salt, solvate, solvate of such a salt or a prodrug thereof is an IBAT inhibitor or a pharmaceutically acceptable salt thereof.

Therefore in an additional feature of the invention, there is provided a combination of a compound of formula (I), or a pharmaceutically acceptable salt, solvate, solvate of such a salt or a prodrug thereof and an IBAT inhibitor, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an IBAT inhibitor, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) an IBAT inhibitor, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) an IBAT inhibitor, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and an IBAT inhibitor, or a pharmaceutically acceptable salt, solvate, solvate of such a salt or a prodrug thereof, in the manufacture of a medicament for use in the production of a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an IBAT inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, proglitazone, rosiglitazone, eglitazone, proglitazone, NN622/Ragaglitazar, BMS 298585, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4(2-{4-methanesulphonyloxyphenyl}ethoxy)phenyl]propanoic acid and pharmaceutically acceptable salts thereof.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:

a) a compound of formula (I), or a pharmaceutically acceptable salt, solvate, solvate of such a salt or a prodrug thereof, in a first unit dosage form;

b) a PPAR alpha and/or gamma agonist, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) a PPAR alpha and/or gamma agonist, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in producing a cholesterol lowering effect in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In another aspect of the invention, the compound of formula (I), or a pharmaceutically acceptable salt, solvate, solvate of such a salt or a prodrug thereof, may be administered in association with a nicotinic acid derivative or a pharmaceutically acceptable salt, solvate, solvate of such a salt or a prodrug thereof. As used herein "nicotinic acid derivative" means a compounds comprising a pyridine-3-carboxylate structure or a pyrazine-2-carboxylate structure. Examples of nicotinic acid derivatives include nicotinic acid, niceritrol, nicofuranose, NIASPAN® and acipimox.

Therefore, in an additional feature of the invention, there is provided a combination of a compound of formula (I), or a pharmaceutically acceptable salt, solvate, solvate of such a salt or a prodrug thereof and a nicotinic acid derivative or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a nicotinic acid derivative, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a nicotinic acid derivative, or a pharmaceutically acceptable salt, solvate, solvate of such a salt or a prodrug thereof, in the manufacture of a medicament for use in the production of a cholesterol lowering effect in a warm-blooded animal, such as man.

In another aspect of the invention, the compound of formula (I), or a pharmaceutically acceptable salt, solvate, solvate of such a salt or a prodrug thereof, may be administered in association with a bile acid sequestrant or a pharmaceutically acceptable salt, solvate, solvate of such a salt or a prodrug thereof. Suitable bile acid sequestrants include cholestyramine, cholestipol and cosevelam hydrochloride.

Therefore, in an additional feature of the invention, there is provided a combination of a compound of formula (I), or a pharmaceutically acceptable salt, solvate, solvate of such a salt or a prodrug thereof and a bile acid sequestrant or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid sequestrant, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a bile acid sequestrant, or a pharmaceutically acceptable salt, solvate, solvate of such a salt or a prodrug thereof, in the manufacture of a medicament for use in the production of a cholesterol lowering effect in a warm-blooded animal, such as man.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

an antihypertensive compound (for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyidopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine male ate and bevantolol hydrochloride);

an angiotensin converting enzyme inhibitor (for example alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabicipriltat, zofenopril and zofenoprilat);

an angiotensin II receptor antagonist (for example candesartan, candesartan cilexetil, losartan, valsartan, irbesartan, tasosartan, telmisartan and eprosartan);

an andrenergic blocker (for example bretylium tosylate, dihydroergotamine so mesylate, phentolamine mesylate, solypertine tartrate, zolertine hydrochloride, carvedilol or labetalol hydrochloride); an alpha andrenergic blocker (for example fenspiride hydrochloride, labetalol hydrochloride, proroxan and alfuzosin hydrochloride); a beta andrenergic blocker (for example acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol); or a mixed alpha/beta andrenergic blocker;

an andrenergic stimulant (for example combination product of chlorothiazide and methyidopa, the combination product of methyidopa hydrochlorothiazide and methyidopa, clonidine hydrochloride, clonidine, the combination product of chlorthalidone and clonidine hydrochloride and guanfacine hydrochloride);

channel blocker, for example a calcium channel blocker (for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil);

a diuretic (for example the combination product of hydrochlorothiazide and spironolactone and the combination product of hydrochlorothiazide and triamterene);

anti-anginal agents (for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride);

vasodilators for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol and verapamil);

anti-coagulants (selected from argatroban, bivalirudin, dalteparin sodium, desirudin, dicumarol, lyapolate sodium, nafamostat mesylate, phenprocoumon, tinzaparin sodium and warfarin sodium);

antithrombotic agents (for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab aritox);

fibrinogen receptor antagonists (for example roxifiban acetate, fradafiban, orbofiban, lotrafiban hydrochloride, tirofiban, xemilofiban, monoclonal antibody 7E3 and sibrafiban)

platelet inhibitors (for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole);

platelet aggregation inhibitors (for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban)

hemorrheologic agents (for example pentoxifylline);

lipoprotein associated coagulation inhibitors;

Factor VIIa inhibitors;

Factor Xa inhibitors;

low molecular weight heparins (for example enoxaparin, nardroparin, dalteparin, certroparin, parnaparin, reviparin and tinzaparin);

squalene synthase inhibitors;

squalene epoxidase inhibitors;

liver X receptor (LXR) agonists for example GW-3965 and those described in WO00224632, WO0103705, WO02090375 and WO00054759 (claim 1 and the named examples of these four application are incorporated herein by reference);

microsomal triglyceride transfer protein inhibitors for example implitapide and those described in WO03004020, WO03002533, WO02083658 and WO 00242291 (claim 1 and the named examples of these four application are incorporated herein by reference);

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method for producing a cholesterol lowering effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the production of a cholesterol lowering effect in a warm-blooded animal, such as man.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of cholesterol absorption in laboratory animals such as cats, dogs, rabbits, monkeys, rats and mice, as part of the search for new therapeutic agents.

Many of the intermediates described herein are novel and are thus provided as a further feature of the invention. For example compounds of formula (IV) show cholesterol absorption inhibitory activity when tested in the above referenced in vitro test assay and are thus claimed as a further feature of the invention.

Thus in a further feature of the invention, there is provided a compound of formula (IV), or a pharmaceutically acceptable salt, solvate, solvate of such a salt or a prodrug thereof.

Therefore according to a further aspect of the invention there is provided a pharmaceutical composition which comprises a compound of formula (W), or a pharmaceutically acceptable salt, solvate, solvate of such a salt or a prodrug thereof, as defined hereinbefore in association with a pharmaceutically-acceptable diluent or carrier.

According to an additional aspect of the present invention there is provided a compound of the formula (IV), or a pharmaceutically acceptable salt, solvate, solvate of such a salt or a prodrug thereof, as defined hereinbefore for use in a method of prophylactic or therapeutic treatment of a warm-blooded animal, such as man.

Thus according to this aspect of the invention there is provided a compound of the formula (IV), or a pharmaceutically acceptable salt, solvate, solvate of such a salt or a prodrug thereof, as defined hereinbefore for use as a medicament.

According to another feature of the invention there is provided the use of a compound of the formula (IV), or a pharmaceutically acceptable salt, solvate, solvate of such a salt or a prodrug thereof as defined hereinbefore in the manufacture of a medicament for use in the production of a cholesterol absorption inhibitory effect in a warm-blooded animal, such as man.

According to another feature of the invention there is provided the use of a compound of the formula (IV), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man.

According to a further feature of this aspect of the invention there is provided a method for producing a cholesterol absorption inhibitory effect in a warm-blooded animal, such as man, in need of such treatment which comprises administering to said animal an effective amount of a compound of formula (IV), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (a), or a pharmaceutically acceptable salt, solvate, solvate of such a salt or a prodrug thereof.

In the above other pharmaceutical composition, process, method, use and medicament manufacture features, the alternative and preferred embodiments of the compounds of the invention described herein also apply.

EXAMPLES

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically. in the range 18-25° C., with solvents of HPLC grade under anhydrous conditions, unless otherwise stated;

(iii) column chromatography (by the flash procedure) was performed on Silica gel 40-63 µm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated CDCl$_3$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer unless otherwise stated data was recorded at 400 MHz; and peak multiplicities are shown as follows: s, singlet; d, doublet; dd, double doublet; t, triplet; tt, triple triplet; q, quartet; tq, triple quartet; m, multiplet; br, broad; ABq, AB quartet; ABd, AB doublet, ABdd, AB doublet of doublets; dABq, doublet of AB quartets; LCMS were recorded on a Waters ZMD, LC column xTerra MS C$_8$(Waters), detection with a HP 1100 MS-detector diode array equipped; mass spectra (MS) (loop) were recorded on VG Platform II (Fisons Instruments) with a HP-1100 MS-25 detector diode array equipped; unless otherwise stated the mass ion quoted is (MH$^+$); unless further details are specified in the text, analytical high performance liquid chromatography (HPLC) was performed on Prep LC 2000 (Waters), Cromasil C$_8$, 7 µm, (Akzo Nobel); MeCN and de-ionised water 10 mM ammonium acetate as mobile phases, with suitable composition;

(vii) intermediates were not generally fully characterised and purity was assessed by thin layer chromatography (TLC), BPLC, infra-red (IR), MS or NMR analysis;

(viii) where solutions were dried sodium sulphate was the drying agent; and (ix) the following abbreviations may be used hereinbefore or hereinafter:

| | |
|---|---|
| DCM | dichloromethane; |
| DMF | N,N-dimethylformamide; |
| TBTU | o-Benzotriazol-1-yl-N,N,N',N'-tetramethyluronium-tetrafluoroborate; |
| EtOAc | ethyl acetate; |
| MeCN | acetonitrile; |
| TFA | trifluoroacetic acid; |
| IPA | isopropanol; |
| DIPEA | di-isopropylethylamine; and |
| THF | tetrahydrofuran. |

Example 1

1-(4-Fluorophenyl)-3-[3-(4-fluorophenyl)-3-hydroxypropyl]-4-[4-(N-{(R)-α-[N-(t-butoxycarbonylmethyl)carbamoyl]benzyl}carbamoylmethoxy)phenyl]azetidin-2-one 1-(4-Fluorophenyl)-3-[3-(4-fluorophenyl)-3-hydroxypropyl]-4-(4-carboxymethoxyphenyl)azetidin-2-one (Method 1; 20 mg, 0.043 mmol), tert-butyl N-[(2R)-2-amino-2-phenylethanoyl]glycinate (Method 4; 14 mg, 0.047 mmol) and 2,6- lutidine (25 µl, 0.21 mmol) were added to DCM (2 ml) and the mixture was stirred for 5 minutes. TBTU (18 mg, 0.056 mmol) was added and the mixture was stirred for 4 hours at room temperature. The reaction mixture was purified by column chromatography using DCM/EtOAc (10/2) as eluent to give 17 mg (56%) of the title compound. M/z 712.4 (m−H)$^-$.

Example 2

1-(4-Fluorophenyl)-3-[3-(4-fluorolphenyl)-3-hydroxypropyl]-4-[4-(N-{(R)-α-[N-(carboxymethyl) carbamoyl]benzyl}carbamoylmethoxy)phenyl]azetidin-2-one 1-(4-Fluorophenyl)-3-[3-(4-fluorophenyl)-3-hydroxypropyl]-4-[4-(N-{(R)-α-[N-(t-butoxycarbonylmethyl)carbamoyl]benzyl}carbamoylmethoxy)phenyl]azetidin-2-one (Example 1; 17 mg, 0.024 mmol) was added to formic acid (1 ml) and the mixture was stirred for 2.5 hours at room temperature. The solvent was evaporated under reduced pressure and methanol (1 ml) and triethylamine (75 µl) were added to the residue. The mixture was stirred for 4.5 hours at room temperature and the solvents were evaporated under reduced pressure. The residue was solved in MeCN/water (50/50) (3 ml) and acetic acid (1 ml). The mixture was lyophilised to obtain 13 mg (83%) of the title compound. NMR (300 MHz, DMSO-d$_6$):1.65-1.85 (m, 4H), 3.05 (bs, 1H), 3.5-3.7 (m, 3H), 4.45-4.55 (m, 1H), 4.6 (d, 2H), 4.85 (m, 1H), 5.55 (d, 1H), 6.9 (d, 1H), 7.05-7.4 (m, 17H), 8.4-8.55 (m, 2H); m/z 656.2 (m−H)$^-$.

Example 3

1-(4-Fluorophenyl)-3-[3-(4-fluorophenyl)-3-hydroxypropyl]-4-{4[N-((2-(S)-3-(R)-4-(R)-5-(R)-2,3,4,5,6-pentahydroxyhexyl)carbamoylmethoxy] phenyl}azetidin-2-one 1-(4-Fluorophenyl)-3-[3-(4-fluorophenyl)-3-hydroxypropyl]-4-(4-carboxymethoxy phenyl)azetidin-2-one (Method 1; 40 mg, 0.086 mmol), D-glucamine (16 mg, 0.09 mmol) and 2,6-lutidine (50 µl, 0.42 mmol) were added to DCM (3 ml) and 2 drops of DMF. TBTU (36 mg, 0. 11 mmol) was added and the mixture was stirred at room temperature for 2 hours. The solvents were evaporated under reduced pressure and the residue was purified twice by preparative HPLC using MeCN/ammonium acetate buffer (45:55) as eluent. The collected fractions were lyophilised to obtain 16 mg (30%) of the title compound. NMR (300 MHz, CD$_3$OD): 1.8-2.0 (m, 4H), 3.15-3.2 (m, 1H), 3.4-4.0 (m, 8H), 4.6 (s, 2H), 4.7-4.8 (m, 1H), 4.9 (bs, 1H), 7.0-7.5 (m, 12H); m/z 629.2 (m−H)$^-$.

Example 4

1-(4-Fluorophenyl)-3-[3-(4-fluorophenyl)-3-hydroxypropyl]-4-{4-[N-((R)-α-{N-(S)-[1-(t-butoxycarbonyl)-2-(t-butoxy)ethyl]carbamoyl}benzyl)carbamoylmethoxy]phenyl}azetidin-2-one 1-(4-Fluorophenyl)-3-[3-(4-fluorophenyl)-3-hydroxypropyl]-4-(4-carboxymethoxy phenyl)azetidin-2-one (Method 1; 40 mg, 0.086 mmol), tert-butyl N-[(2R)-2-amino-2-phenylethanoyl]-O-(tert-butyl)-L-serinate (Method 6; 33 mg, 0.095 mmol) and 2,6-lutidine (50 µl, 0.42 mmol) were added to DCM (3 ml). TBTU (36 mg, 0.11 mmol) was added and the mixture was stirred at room temperature for 7 hours. The solvents were evaporated under reduced pressure to give a mixture containing the title compound. M/z 798.4 (M−H)$^-$.

Example 5

1-(4-Fluorophenyl)-3-[3-(4-fluorophenyl)-3-hydroxypropyl]-4-{4-[N-((R)-α-{N-(S)-[1-(carboxy)-2-(hydroxyl)ethyl]carbamoyl}benzyl)carbamoylmethoxy]phenyl}azetidin-2-one The 1-(4-fluorophenyl)-3-[3-(4-fluorophenyl)-3-hydroxypropyl]-4-{4-[N-(R)-α-{N-(S)-[1-(t-butoxycarbonyl)-2-(t-butoxy)ethyl]carbamoyl}benzyl)carbamoylmethoxy]phenyl}azetidin-2-one prepared in Example 4 was added to formic acid (3 ml) and the mixture was stirred for 5 days at room temperature. The solvent was evaporated under reduced pressure and methanol (4 ml) and triethylamine (0.4 ml) were added to the residue. The mixture was stirred for 24 hours at room temperature and the solvents were evaporated under reduced pressure. The residue was purified by preparative HPLC using MeCN/ammonium acetate buffer (40:60) as eluent. The collected fractions were lyophilised to obtain 12 mg (20%, 2 steps) of the title compound. NMR (300 MHz, $CD_3OD$): 1.8-1.95 (m, 4H), 3.1 (bs, 1H), 3.7-3.8 (m, 2H), 4.35 (bs, 1H), 4.55-4.7 (m, 3H), 4.8 (s, 1H), 5.65 (s, 1H), 6.95-7.4 (m, 17H); m/z 686.3 $(m-H)^-$.

Example 6

1-(4-Fluorolphenyl)-3-[3-(4-fluorophenyl)-3-hydroxypropyl]-4-{4-{N-[(R)-α-(t-butoxycarbonyl)benzyl]carbamoylmethoxy}phenyl}azetidin-2-one 1-(4-Fluorophenyl)-3-[3-(4-fluorophenyl)-3-hydroxypropyl]-4-(4-carboxymethoxy phenyl)azetidin-2-one (Method 1; 40 mg, 0.086 mmol tert-butyl (2R)-amino(phenyl)acetate (20 mg, 0.095 mmol) and 2,6-lutidine (50 µl, 0.42 mmol) were added to DCM (3 ml). TBTU (36 mg, 0.11 mmol) was added and the mixture was stirred at room temperature for 5 hours. The solvent was evaporated under reduced pressure and was co-evaporated with toluene. The residue was purified by column chromatography using DCM/EtOAc (10/2) as eluent to give the title compound. M/z 655.3 $(m-H)^-$.

Example 7

1-(4-Fluorophenyl)-3-[3-(4-fluorophenyl)-3-hydroxypropyl]-4-(4-{N-[(R)-α-(carboxy) benzyl]carbamoylmethoxy}phenyl)azetidin-2-one The 1-(4-fluorophenyl)-3-[3-(4-fluorophenyl)-3-hydroxypropyl]-4-{4-{N-[R)-α-(t-butoxycarbonyl)benzyl]carbamoylmethoxy}phenyl}azetidin-2-one prepared in Example 6 was added to formic acid (3 ml) and the mixture was stirred for 12 hours at room temperature. The solvent was evaporated under reduced pressure and was co-evaporated with toluene. Methanol (3 ml) and triethylamine (0.1 ml) were added to the residue and the mixture was stirred for 4 hours at room temperature The solvents were evaporated under reduced pressure and the residue was purified by preparative HPLC using MeCN/ammonium acetate buffer (50:50) as eluent. The collected fractions were lyophilised to obtain 17 mg (33%, 2 steps) of the title compound. NMR (300 MHz, $CD_3OD$): 1.8-2.0 (m, 4H), 3.05-3.15 (m, 1H), 4.5-4.7 (m, 3H), 4.8 (bs, 1H), 5.35 (d, 1H), 6.95-7.45 (m, 17H); m/z 599.5 $(m-H)^-$.

Example 8

1-(4-Fluorophenyl)-3-[3-(4-fluorophenyl)-3-hydroxypropyl]-4-{4-[N-(t-butoxycarbonylmethyl)carbamoylmethoxy]phenyl}azetidin-2-one 1-(4-Fluorophenyl)-3-[3-(4-fluorophenyl)-3-hydroxypropyl]-4-(4-carboxymethoxy phenyl)azetidin-2-one (Method 1; 40 mg, 0.086 mmol), glycine tert-butylester (18 mg, 0.091 mmol) and 2,6-lutidine (50 µl, 0.42 mmol) were added to DCM (3 ml). TBTU (36 mg, 0.11 mmol) was added and the mixture was stirred at room temperature for 20 hours. The solvent was evaporated under reduced pressure. The residue was purified by column chromatography using DCM/EtOAc (10/4) as eluent to give the title compound, M/z 579.2 $(m-H)^-$.

Example 9

1-(4-Fluorophenyl)-3-[3-(4-fluorophenyl)-3-hydroxypropyl]-4-{4-[N-(carboxymethyl)carbamoylmethoxy]phenyl}azetidin-2-one The 1-(4-fluorophenyl)-3-[3-(4-fluorophenyl)-3-hydroxypropyl]-4-{4-[N-(t-butoxycarbonylmethyl)carbamoylmethoxy]phenyl}azetidin-2-one prepared in Example 8 was added to formic acid (3 ml) and the mixture was stirred for 4 hours at room temperature. The solvent was evaporated under reduced pressure and was co-evaporated with toluene. Methanol (3 ml) and triethylamine (0.1 ml) were added to the residue and mixture was stirred for 20 hours at room temperature The solvents were evaporated under reduced pressure and the residue was purified by preparative HPLC using MeCN/ammonium acetate buffer (45:55) as eluent. The collected fractions were lyophilised to obtain 14 mg (31%, 2 steps) of the title compound. NMR (300 MHz, $CD_3OD$): 1.8-2.0 (m, 4H), 3.05-3.15 (m, 1H), 3.85 (s, 2H), 4.55 (s, 2H), 4.6-4.7 (m, 1H), 4.8 (bs, 1H), 6.95-7.35 (m, 12 H); m/z 523.1 $(m-H)^-$.

Example 10

1-(4-Fluorophenyl)-3-[2-(4-fluorophenoxy)ethyl]-4-{4-[N-(carboxymethyl)carbamoyl methoxy]phenyl}azetidin-2-one A solution of 1-(4-fluorophenyl)-3-[2-(4-fluorophenoxy)ethyl]-4-[4-(carboxymethoxy) phenyl]azetidin-2-one (Method 8; 0.050 g, 0.110 mmol), tert-butyl glycinate hydrochloride (0.022 g, 0.131 mmol) and N-methylmorpholine (0.050 ml, 0.454 mmol) in DCM (3 ml) was stirred at room temperature for 5 minutes, after which TBTU (0.046 g, 0.143 mmol) was added. After 78 hours the conversion to the ester (m/z: 567.2) was completed and the solvent was removed under reduced pressure. The residue was dissolved in formic acid (3 ml) and the solution was stirred for 20 hours. The solvent was removed under reduced pressure and the residue was purified by preparative HPLC using a gradient of 20-50% MeCN in 0.1M ammonium acetate buffer as eluent. The fractions were freeze-dried and the title compound was obtained as a white solid (0.056 g; ~quantitative yield). NMR ($CD_3OD$, 400 MHz) 2.25-2.40 (m, 2H), 3.25-3.35 (m, 1H), 3.90.(s, 2H), 4.05-4.20 (m, 2H),4.50 (s, 2H) 5.00 (d, 1H), 6.80-7.05 (m, 8H), 7.25-7.40 (m, 4H); m/z: 511.1.

Example 11

1-(4-Fluorophenyl)-3-[2-(4-fluorophenoxy)ethyl]-4-(4-{N-[(R)-α-(carboxy)-4-(hydroxy)benzyl]carbamoylmethoxy}phenyl)azetidin-2-one A solution of 1-(4-fluorophenyl)-3-[2-(4-fluorophenoxy)ethyl]-4-[4-(carboxymethoxy) phenyl]azetidin-2-one (Method 8; 0.070 g, 0.154 mmol), tert-butyl D-tyrosinate (0.044 g, 0.185 mmol) and N-methylmorpholine (0.051 ml, 0.463 mmol) in DCM (5 ml) was stirred at room temperature for 5 minutes, after which TBTU (0.065 g, 0.202 mmol) was added. After 20 hours, the conversion to the ester (m/z: 673.4) was complete and the solvent was removed under reduced pressure. The residue was dissolved in formic acid (5 ml) and the solution was stirred for 24 hours. The solvent was removed under reduced pressure and the residue was purified by preparative IPLC using a gradient of 20-50% MeCN in 0.1M ammonium acetate buffer as eluent. The fractions were freeze-dried and the title compound was obtained as a white solid (0.052 g; 55%). NMR ($CD_3OD$, 400 MHz) 2.25-2.40 (m, 2H), 2.85-3.15 (m, 2H), 3.25-3.40 (m, 1H), 4.05-4.20 (m, 2H), 4.35-4.50 (m, 2H), 4.55-4.65 (m, 1H), 5.00 (d, 1H), 6.55-6.65 (m, 2H), 6.80-7.05 (m, 10H), 7.25-7.35 (m, 4H); m/z: 615.2 (M−H)⁻.

Example 12

1-(4-Fluorophenyl)-3-[2-(4-fluorophenoxy)ethyl]-4-(4-{N-[(R)-1-(carboxy)-2-(hydroxy)ethyl]carbamoylmethoxy}phenyl)azetidin-2-one A solution of 1-(4-fluorophenyl)-3-[2-(4-fluorophenoxy)ethyl]-4-[4-(carboxymethoxy) phenyl]azetidin-2-one (Method 8; 0.070 g, 0.154 mmol), tert-butyl O-(tert-butyl)-D-serinate hydrochloride (0.047 g, 0.185 mmol) and N-methylmorpholine (0.068 ml, 0.617 mmol) in DCM (5 ml) was stirred at room temperature for 5 minutes, after which TBTU (0.065 g, 0.202 mmol) was added. After 20 hours, the conversion to the ester (m/z: 653.4) was completed and TFA (1.5 ml) was added to the reaction mixture. After 24 hours the solvent was removed under reduced pressure and the residue was purified by preparative HPLC, using a gradient of 20-50% MeCN in 0.1M ammonium acetate buffer as eluent. The fractions were freeze-dried and the title compound was obtained as a white solid (0.074 g; 89%). M/z: 541.1. NMR ($CD_3OD$, 400 MHz) 2.25-2.40 (m, 2H), 3.25-3.35 (m, 1H), 3.80-3.95 (m, 2H), 4.05-4.20 (m, 2H), 4.40 (t, 1H), 4.55 (s, 2H), 5.00 (d, 1H), 6.80-6.90 (m, 2H), 6.90-7.05 (m, 6H), 7.25-7.40 (m, 4H).

Example 13

1-(4-Fluorophenyl)-3-[2-(4-fluorophenoxy)ethyl]-4-{4-[N-((R)-1-carboxy-3-methylbutyl)carbamoylmethoxy]phenyl}azetidin-2-one A solution of 1-(4-fluorophenyl)-3-[2-(4-fluorophenoxy)ethyl]-4-[4-(carboxymethoxy)phenyl]azetidin-2-one (Method 8; 0.070 g, 0.154 mmol), tert-butyl D-leucinate hydrochloride (0.042 g, 0.188 mmol) and N-methylmorpholine (0.068 ml, 0.617 mmol) in DCM (5 ml) was stirred at room temperature for 5 minutes, after which TBTU (0.065 g, 0.202 mmol) was added. After 20 hours, the conversion to the ester (m/z: 623.3) was complete and the solvent was removed under reduced pressure. The residue was dissolved in formic acid (5 ml) and the solution was stirred for 20 hours. The solvent was removed under reduced pressure and the residue was purified by preparative BPLC using a gradient of 20-50% MeCN in 0.1M ammonium acetate buffer as eluent. The fractions were freeze-dried and the title compound was obtained as a white solid (0.080 g; 91%). NMR (DMSO, 400 MHz) 0.75-0.85 (m, 6H), 1.45-1.60 (m, 3H), 2.15-2.30 (m, 2H), 3.20-3.30 (m, 1H), 4.00-4.25 (m, 3H), 4.50 (ABq, 2H), 5.05 (d, 1H), 6.85-6.95 (m, 4H), 7.00-7.25 (m, 6H), 7.30-7.40 (m, 2H), 8.05 (t, 1H); m/z: 567.3.

Example 14

1-(4-Fluorophenyl)-3-[2-(4-fluorophenoxy)ethyl]-4-(4-{N-[(S)-1-(carboxy)-3-(carbamoyl) propyl]carbamoylmethoxy}phenyl)azetidin-2-one A solution of 1-(4-fluorophenyl)-3-[2-(4-fluorophenoxy)ethyl]-4-[4-(carboxymethoxy) phenyl]azetidin-2-one (Method 8; 0.070 g, 0.154 mmol), tert-butyl L-glutaminate hydrochloride (0.044 g, 0.184 mmol) and N-methylmorpholine (0.068 ml, 0.617 mmol) in DCM (5 ml) was stirred at room temperature for 5 minutes, after which TBTU (0.065 g, 0.202 mmol) was added. After 20 hours, the conversion to the ester (m/z: 638.3) was complete and the solvent was removed under reduced pressure. The residue was dissolved in formic acid (5 ml) and the solution was stirred for 20 hours. The solvent was removed under reduced pressure and the residue was purified by preparative HPLC using a gradient of 20-50% MeCN in 0.1M ammonium acetate buffer as eluent. The fractions were freeze-dried and the title compound was obtained as a white solid (0.088 g; 98%). NMR ($CD_3OD$, 400 MHz) 1.90-2.40 (m, 6H), 3.25-3.35 (m, 1H), 4.05-4.20 (m, 2H), 4.30-4.40 (m, 1H), 4.50 (s, 2H), 5.00 (d, 1H), 6.80-7.05 (m, 8H), 7.25-7.40 (m, 4H); m/z: 582.2.

Example 15

1-(4-Fluorophenyl)-3-[2-(4-fluorophenoxy)ethyl]-4-{4-[N-((R)-α-{N-[(S)-1-(carboxy)-2-(hydroxy)ethyl]carbamoyl}benzyl)carbamoylmethoxy]phenyl}azetidin-2-one A solution of 1-(4-fluorophenyl)-3-[2-(4-fluorophenoxy)ethyl]-4-[4-(carboxymethoxy) phenyl]azetidin-2-one (Method 8; 0.051 g, 0.113 mmol), tert-butyl N-[(2R)-2-amino-2-phenylethanoyl]-O-(tert-butyl)-L-serinate (Method 6; 0.047 g, 0.134 mmol) and N-methylmorpholine (0.050 ml, 0.454 mmol) in DCM (5 ml) was stirred at room temperature for 10 minutes, after which TBTU (0.065 g, 0.202 mmol) was added. After 18 hours, the conversion to the ester (m/z: 786.5) was complete and TFA (1.5 ml) was added to the reaction mixture. After 24 hours the solvent was removed under reduced pressure and the residue was purified by preparative HPLC using a gradient of 30-50% MeCN in 0.1M ammonium acetate buffer as eluent. The fractions were freeze-dried and the title compound was obtained as a white solid (0.057 g; 75%). NMR ($CD_3OD$, 400 MHz) 2.25-2.40 (m, 2H), 3.25-3.35 (m, 1H), 3.65-3.85 (m, 2H), 4.05-4.20 (m, 2H), 4.30-4.40 (m, 1H), 4.50-4.65 (m, 2H), 5.00 (d, 1H), 5.65 (s, 1H), 6.80-7.05 (m, 8H), 7.20-7.45 (m, 9H); m/z: 674.2.

Example 16.

1-(4-Fluorophenyl)-3-[2-(4-fluorophenoxy)ethyl]-4-{4-[N-{(R)-α-[N-((S)-1-carboxypropyl) carbamoyl]-4-hydroxybenzyl}carbamoylmethoxy] phenyl}azetidin-2-one A solution of 1-(4-fluorophenyl)-3-[2-(4-fluorophenoxy) ethyl]-4-[4-(carboxymethoxy) phenyl]azetidin-2-one (Method 8; 0.050 g, 0.110 mmol), (R)-α-{N-[(S)-1-(t-butoxycarbonyl)propyl]carbamoyl}-4-hydroxybenzylamine (Method 11 of WO 03/022286; 0.046 g, 0.133 mmol) and N-methylmorpholine (0.049 ml, 0.445 mmol) in DCM (5 ml) was stirred at room temperature for 10 minutes, after which TBTU (0.046 g, 0.143 mmol) was added. After 20 hours, the conversion to the ester (m/z: 744.5) was completed and the solvent was removed under reduced pressure. The residue was dissolved in formic acid (3 ml) and the solution was stirred for 24 hours before the solvent again was removed under reduced pressure. The residue was purified by preparative HPLC using a gradient of 30-50% MeCN in 0.1M ammonium acetate buffer as eluent. The fractions were freeze-dried and the title compound was obtained as a white solid (0.052 g; 69%). NMR (CD$_3$OD, 400 MHz) 0.70-0.80.(m, 3H), 1.55-1.70 (m, 1H), 1.75-1.90 (m, 1H), 2.25-2.40 (m, 2H), 3.25-3.35 (m, 1H), 4.05-4.20 (m, 2H), 4.20-4.30 (m, 1H), 4.55 (ABq, 2H), 5.00 (d, 1H), 5.50 (d, 1H), 6.65-6.75 (m, 2H), 6.80-7.05 (m, 8H), 7.15-7.40 (m, 6H); m/z: 688.2.

Example 17

3-(R)-4-(R)-1-(Phenyl)-3-(phenylethylsulphanyl)-4-{4-[N-((R)-α-{N-[(S)-1-(carboxy)-2-(hydroxy)ethyl] carbamoyl}benzyl)carbamoylmethoxy] phenyl}azetidin-2-one A solution of 3-(R)-4-(R)-1-(phenyl)-3-(phenylethylsulphanyl)-4-[4-(carboxymethoxy)phenyl]azetidin-2-one (Method 9; 0.050 g, 0.115 mmol), tert-butyl N-[(2R)-2-amino-2-phenylethanoyl]-O-(tert-butyl)-L-serinate (Method 6; 0.049 g, 0.140 mmol) and N-methylmorpholine (0.050 ml, 0.454 mmol) in DCM (5 ml) was stirred at room temperature for 10 minutes, after which TBTU (0.075 g, 0.234 mmol) was added. After 18 hours, the conversion to the ester (m/z: 766.5) was complete and TFA (1.5 ml) was added to the reaction mixture. After 24 hours the solvent was removed under reduced pressure and the residue was purified by preparative BPLC, using a gradient of 30-50% MeCN in 0.1M ammonium acetate buffer as eluent. The fractions were freeze-dried and the title compound was obtained as a white solid (0.052 g; 69%). N (CD$_3$OD, 400 MHz) 2.85-3.00 (m, 4H), 3.65-3.85 (m, 2H), 4.00-4.05 (m, 1H), 4.35-4.40 (m, 1H), 4.60 (ABq, 2H), 4.85 (d, 1H), 5.65 (s, 1H), 6.95-7.45 (m, 19H); m/z: 654.2.

Example 18

3-(R)-4-(R)-1-(Phenyl)-3-(phenylethylsulphanyl)-4-{4-[N-{(R)-α-[N-((S)-1-carboxypropyl)carbamoyl]-4-hydroxybenzyl}carbamoylmethoxy] phenyl}azetidin-2-one A solution of 3-(R)4-(R)-1-(phenyl)-3-(phenylethylsulphanyl)-4-[4-(carboxymethoxy)phenyl]azetidin-2-one (Method 9; 0.050 g, 0.110 mmol), (R)-α-{N-[(S)-1-(t-butoxycarbonyl)propyl]carbamoyl}-4-hydroxybenzylamine (Method 11 of WO 03/022286; 30 0.048 g, 0.139 mmol) and N-methylmorpholine (0.051 ml, 0.463 mmol) in DCM (5 ml) was stirred at room temperature for 10 minutes, after which TBTU (0.075 g, 0.234 mmol) was added. After 20 hours, the conversion to the ester (m/z: 724.4) was completed and the solvent was removed under reduced pressure. The residue was dissolved in formic acid (3 ml) and the solution was stirred for 24 hours. The solvent was removed under reduced pressure and the residue was purified by preparative HPLC using a gradient of 30-50% MeCN in 0.1M ammonium acetate buffer as eluent. The fractions were freeze-dried and the title compound was obtained as a white solid (0.037 g; 48%). M/z: 668.1. NMR (CD$_3$OD, 400 MHz) 0.65-0.80 (m, 3H), 1.50-1.70 (m, 1H), 1.75-1.90 (m, 1H), 2.85-3.00 (m, 4H), 4.00-4.05 (m, 1H), 4.20-4.30 (m, 1H), 4.55 (ABq, 2H), 4.85 (d, 1H), 4.45-4.55 (m, 1H), 6.65-6.75 (m, 2H), 6.95-7.40 (m, 16H).

Example 19

3-(R)-4-(R)-1-(Phenyl)-3-(phenylethylsulphanyl)-4-{4-[N-{(R)-α-[N-((S-1-carboxypropyl) carbamoyl]-4-hydroxybenzyl}carbamoylmethoxy] phenyl}azetidin-2-one To a solution of 3-(R)-4-(R)-1-(phenyl)-3-(phenylethylsulphanyl)-4-{4-[N-{(R)-α-[N-((S)-1-carboxypropyl)carbamoyl]-4-hydroxybenzyl}carbamoylmethoxy] phenyl}azetidin-2-one (Example 18; 0.026 g, 0.039 mmol) in DCM (3 ml) was added a solution of MCPBA in DCM in portions until the reaction was complete (LC/MS). (Approximately 0.015 g 70-75% m-CPBA was added). The solvent was removed under reduced pressure and the residue was purified by preparative HPLC using a gradient of 20-50% MeCN in 0.1M ammonium acetate buffer as eluent After freeze-drying, the title compound was obtained as a white solid (0.018 g; 67%). NMR (CD$_3$OD, 400 MHz) (NB: diastereomeric mixture at the sulphinyl) 0.65-0.80.(m, 6H), 1.55-1.70 (m, 2H), 1.75-1.90 (m, 2H), 2.95-3.35 (m, 7H), 3.75-3.90 (m, 1H), 4.20-4.30 (m, 2H), 4.40-4.50 (m, 1H), 4.50-4.65 (m, 5H), 5.30 (d, 1H), 5.45-5.55 (m, 2H), 5.65 (d, 1H), 6.65-6.80 (m, 4H), 6.95-7.10 (m, 6H), 7.15-7.35 (m, 22H), 7.35-7.50 (m, 4H); m/z: 684.4.

Example 20

3-(R)-4-(R)-1-(Phenyl)-3-(4-fluorobenzoylmethylsulphanyl)-4-{4-[N-(carboxymethyl) carbamoylmethoxy]phenyl}azetidin-2-one A solution of 3-(R)-4-(R)-1-(phenyl)-3-(4-fluorobenzoylmethylsulphanyl)-4-[4-(carboxymethoxy)phenyl]azetidin-2-one (Method 10; 0.110 g, 0.236 mmol), tert-butyl glycinate hydrochloride (0.067 g, 0.400 mmol) and N-methylmorpholine (0.12 ml, 1.09 mmol) in DCM (5 ml) was stirred at room temperature for 5 minutes, after which TBTU (0.130 g, 0.4049 mmol) was added. After 66 hours the conversion to the ester (m/z: 579.2) was complete and the solvent was removed under reduced pressure. The residue was dissolved in formic acid (3 ml) and the solution was stirred at 40° C. for 4 hours. The solvent was removed under reduced pressure and the residue was purified by preparative HPLC using a gradient of

Example 21

3-(R)-4-(R)-1-(Phenyl)-3-(4-fluorobenzoylmethyl-sulphanyl)-4-[4-(N-{N-[(R)-1-(t-butoxycarbonyl)-2-(t-butoxy)ethyl]carbamoylmethyl}carbamoylmethoxy)phenyl]azetidin-2-one A solution of 3-(R)-4-(R)-1-(phenyl)-3-(4-fluorobenzoylmethylsulphanyl)-4-{4-[N-(carboxymethyl)carbamoylmethoxy]phenyl}azetidin-2-one (Example 20; 0.020 g, 0.038 mmol), tert-butyl O-(tert-butyl)-D-serinate hydrochloride (0.012 g, 0.047 mmol) and N-methylmorpholine (0.013 ml, 0.118 mmol) in DCM (3 ml) was stirred at room temperature for 10 minutes, after which TBTU (0.016 g, 0.050 mmol) was added. After 66 hours the solvent was removed under reduced pressure and the residue was purified by flash chromatography using heptane:EtOAc (1:2) as eluent to give the title compound (0.020 g; 74%). NMR (400 MHz) 1.15 (s, 9H), 1.45 (s, 9H), 3.50-3.55 (m, 1H), 3.75-3.85 (m, 1H), 4.00-4.25 (m, 5H), 4.50 (s, 2H), 4.55-4.65 (m, 1H), 4.85 (d, 1H), 6.90-7.00 (m, 2H), 7.00-7.40 (m, 9H), 7.90-8.05 (m, 2H); m/z: 722.1.

Example 22

3-(R)-4-(R)-1-(Phenyl)-3-(4-fluorobenzoylmethyl-sulphanyl)-4-[4-(N-{N-[(R)-1-(carboxy)-2-(hydroxy)ethyl]carbamoylmethyl}carbamoylmethoxy)phenyl]azetidin-2-one To a solution of 3-(R)-4-(R)-1-(phenyl)-3-(4-fluorobenzoylmethylsulphanyl)-4-[4-(N-{N-[(R)-1-(t-butoxycarbonyl)-2-(t-butoxy)ethyl]carbamoylmethyl}carbamoylmethoxy) phenyl]azetidin-2-one (Example 21; 0.020 g, 0.146 mmol) in DCM (4 ml) was added TFA (1.5 ml). After 18 hours the solvent was removed under reduced pressure and the residue was purified by preparative BPLC using a gradient of 20-50% MeCN in 0.1M ammonium acetate buffer, as eluent. After freeze-drying, the title compound was obtained as a white solid (0.017 g; ~quantitative). NMR (CD$_3$COOH, 400 MHz) δ 3.95 (dd, 1H), 4.10 (dd, 1H), 4.15-4.35 (m, 5H), 4.65 (s, 2H), 4.70-4.80 (m, 1H), 5.05 (d, 1H), 6.90-7.45 (m, 11H), 7.95-8.10 (m, 2H); m/z: 610.2.

Example 23

3-(R)-4-(R)-1-(Phenyl)-3-(4-fluorobenzoylmethyl-sulphanyl)-(4-{4-[N-((R)-α-{N-[(S)-1-(carboxy)-2-(hydroxy)ethyl]carbamoyl}benzyl)carbamoyl-methoxy]phenyl}azetidin-2-one A solution of 3-(R)-4-(R)-1-(phenyl)-3-(4-fluorobenzoylmethylsulphanyl)-4-[4-(carboxymethoxy)phenyl]azetidin-2-one (Method 10; 0.015 g, 0.032 mmol), tert-butyl N-[(2R)-2-amino-2-phenylethanoyl]-O-(tert-butyl)-L-serinate (Method 6; 0.017 g, 0.049 mmol) and N-methylmorpholine (0.011 ml, 0.100 mmol) in DCM (3 ml) was stirred at room temperature for 10 minutes, after which TBTU (0.016 g, 0.50 mmol) was added. After 19 hours the conversion to the ester (m/z: 798.80) was complete and TFA (1.5 ml) was added to the solution. After 7 hours the solvent was removed under reduced pressure and the residue was purified by preparative HPLC using a gradient of 20-50% MeCN in 0.1M ammonium acetate buffer as eluent. After freeze-drying the title compound was obtained as a white solid (0.016 g; 72%). NMR (CD$_3$COOH, 400 MHz) 3.85 (dd, 1H), 4.05 (dd, 1H), 4.20-4.30 (m, 3H), 4.60-4.80 (m, 3H), 5.00 (d, 1H), 5.90-6.00 (m, 1H), 6.90-7.50 (m, 16H), 8.00-8.10 (m, 2H); m/z: 686.6.

Example 24

3-(R)-4-(R)-1-(Phenyl)-3-[2-(4-fluorophenyl)-2-hydroxyethylsulphany[-4-{4-[N-(carboxymethyl)carbamoylmethoxy]phenyl}azetidin-2-one To a stirring solution of 3-(R)-4-(R)-1-(phenyl)-3-(4-fluorobenzoylmethylsulphanyl)-4-{4-[N-(carboxymethyl)carbamoylmethoxy]phenyl}azetidin-2-one To a stirring solution of 3-(R)-4-(R)-1-(phenyl)-3-(fluorobenzomethylsulphanyl)-4-{4-[N-(carboxymethyl)carbamoylmethoxyphenyl}azetidin-2-one (Example 20; 0.010 g, 0.019 mmol) in MeOH (1 ml) was added sodium borohydride (0.001 g, 0.026 mmol). After 10 minutes water (1 ml) was added and the solvent was removed under reduced pressure. The residue was purified by preparative HPLC using a gradient of 20-50% MeCN in 0.1M ammonium acetate buffer as eluent. After freeze-drying the title compound was obtained as a white solid (0.008 g; 80%). M/z: 525.1. NMR (CD$_3$COOD, 400 MHz) 3.00-3.20 (m, 2H), 4.05-4.15 (m, 1H), 4.20 (s, 2H), 4.70 (s, 2H), 4.85-5.00 (m, 2H), 6.95-7.10 (m, 5H), 7.20-7.45 (m, 8H).

Example 25

3-(R)-4-(R)-1-(Phenyl)-3-[2-(4-fluorophenyl)-2-hydroxyethylsulphanyl]-4-[4-(N-{N-[(R)-1-(carboxy)-2-(hydroxy)ethyl]carbamoylmethyl}carbamoylmethoxy)phenyl]azetidin-2-one To a stirred solution of 3-(R)-4-(R)-1-(phenyl)-3-(4-fluorobenzoylmethylsulphanyl)-4-[4-(N-{N-[(R)-1-(carboxy)-2-(hydroxy)ethyl]carbamoylmethyl}carbamoylmethoxy)phenyl]azetidin-2-one (Example 22; 0.015 g, 0.025 mmol) in MeOH (2 ml) was added sodium borohydride (0.003 g, 0.079 mmol). After 5 minutes water (1 ml) was added and the solvent was removed under reduced pressure. The residue was purified by preparative HPLC using a gradient of 20-40% MeCN in 0.1M ammonium acetate buffer as eluent. After freeze-drying the title compound was obtained as a white solid (0.010 g; 66%). NMR (CD$_3$COOD, 400 MHz) 2.95-3.20 (m, 2H), 3.95 (dd, 1H), 4.05-4.15 (m, 2H), 4.25 (ABq, 2H), 4.70 (s, 2H), 4.70-4.80 (m, 1H), 4.85-5.00 (m, 2H), 6.95-7.10 (m, 5H), 7.20-7.45 (m, 8H).

Example 26

3-(R)-4-(R)-1-(Phenyl)-3-[2-(4-fluorophenyl)-2-hydroxyethylsulphanyl]-4-{4-[N-((R)-α-{N-](S)-1-(carboxy)-2-(hydroxy)ethyl]carbamoyl}benzyl)carbamoylmethoxy]phenyl}azetidin-2-one To a solution of 3-(R)-4-(R)-1-(phenyl)-3-(4-fluorobenzoylmethylsulphanyl)-4-{4[N-((R)-α-{N-[(S)-1-(carboxy)-2-(hydroxy)ethyl]carbamoyl}benzyl)carbamoylmethoxy]phenyl}azetidin-2-one (Example 23; 0.019 g, 0.028 mmol) in MeOH (3 ml) was added sodium borohydride (0.005 g, 0.073 mmol). After 10 minutes 0.1M ammonium acetate buffer was added (aq, 1 ml) and the solvent was removed under reduced pressure. The residue was purified by preparative HPLC using a gradient of 20-50% MeCN in 0.1M ammonium acetate buffer as eluent. After freeze-drying, the title compound was obtained as a white solid (0.008 g; 81%). NMR (CD$_3$COOD, 400 MHz) 3.00-3.20 (m, 2H), 3.85 (dd, 1H), 4.00-4.15 (m, 2H), 4.65-4.80 (m, 3H), 4.85-5.00 (m, 2H), 5.95 (s 1H), 6.95-7.10 (m, 5H), 7.20-7.50 (m, 13H); m/z 688.21.

Example 27

3-(R)-4-(R)-1-(Phenyl)-3-(thien-3-ylcarbonylmethyl-sulphanyl)-4-{4-[N-(carboxymethyl) carbamoyl-methoxy]phenyl}azetidin-2-one A solution of 3-(R)-4)-(R)-1-(phenyl)-3-(thien-3-ylcarbonylmethylsulphanyl)-4-[4-(carboxymethoxy)phenyl]azetidin-2-one (Method 11; 0.039 g, <0.086 mmol), tert-butyl glycinate hydrochloride (0.020 g, 0.119 mmol) and N-methylmorpholine (0.035 ml, 0.318 mmol) in DCM (3 ml) was stirred at room temperature for 10 minutes, after which TBTU (0.042 g, 0.131 mmol) was added. After 22 hours the solvent was removed under reduced pressure and the residue was purified by flash chromatography using heptane:EtOAc (1:1) as eluent. This gave 0.035 g of a colourless oil (m/z: 567.1). This oil was dissolved in formic acid (3 ml) and the solution was stirred at room temperature for 18 hours. The solvent was removed under reduced pressure and the residue was purified by preparative HPLC using a gradient of 20-50% MeCN in 0.1M ammonium acetate buffer as eluent. After freeze-drying, the title compound was obtained as a white solid (0.019 g; 43%). NMR (CD$_3$COOD, 400 MHz) 4.15 (ABq, 2H), 4.20 (s, 2H), 4.25 (d, 1H), 4.70 (s, 2H), 5.05 (d, 1H), 6.95-7.15 (m, 4H), 7.20-7.30 (m, 4H), 7.35-7.45 (m, 2H), 7.75-7.90 (m, 2H); m/z: 511.0.

Example 28

3-(R)-4-(R)-1-(Phenyl)-3-(thien-3-ylcarbonylmethyl-sulphanyl)-4-{4-[N-((R)-α-{N-[(S)-1-(carboxy)-2-(hydroxy)ethyl]carbamoyl}benzyl)carbamoyl-methoxy]phenyl}azetidin-2-one A solution of 3-(R)-4-(R)-1-(phenyl)-3-(thien-3-ylcarbonylmethylsulphanyl)-4-[4-(carboxymethoxy) phenyl]azetidin-2-one (Method 11; 0.039 g, <0.086 mmol), tert-butyl N-[(2R)-2-amino-2-phenylethanoyl]-O-(tert-butyl)-L-serinate (Method 6; 0.042g) and N-methylmorpholine (0.022 ml) in DCM (4 ml) was stirred at room temperature for 10 minutes, after which TBTU (0.042 g) was added. After 22 hours the solvent was removed under reduced pressure and the residue was purified by flash chromatography using heptane:EtOAc (1:1) as eluent to give a colourless oil (0.050 g). M/z: 786.6. This oil was dissolved in DCM (4 ml) and TFA (1.5 ml) was added. After 19 hours, the solvent was removed under reduced pressure and the residue was purified twice by preparative HPLC using a gradient of 20-50% MeCN in 0.1M ammonium acetate buffer as eluent. After freeze-drying, the title compound was obtained as a white solid (0.019 g; 33%). No (CD$_3$COOD, 400 MHz) 3.85 (dd, 1H), 4.05 (dd, 1H), 4.15 (ABq, 2H), 4.20-4.30 (m, 1H), 4.60-4.75. (m, 3H), 5.05 (d, 1H), 5.90 (s, 1H), 6.95-7.15 (m, 4H), 7.20-7.50 (m, 11H), 7.75-7.85 (m, 2H); m/z: 674.3.

Example 29

3-(R)-4-(R)-1-(Phenyl)-3-[2-(thien-3-yl)-2-hydroxy-ethylsulphanyl]-4-{4-[N-(carboxymethyl) carbamoylmethoxy]phenyl}azetidin-2-one To a solution of 3-(R)-4-(R)-1-(phenyl)-3-(thien-3-ylcarbonylmethylsulphanyl)-4-{4-[N-(carboxymethyl) carbamoylmethoxy]phenyl}azetidin-2-one (Example 27; 0.012 g, 0.024 mmol) in MeOH (3 ml) was added sodium borohydride (0.006 g, 0.159 mmol). After 10 minutes 0.1M ammonium acetate buffer (aq, 1 ml) was added and the solvent was removed under reduced pressure. The residue was purified by preparative HPLC using a gradient of 20-50% MeCN in 0.1M ammonium acetate buffer as eluent. After freeze-drying the title compound was obtained as a white solid (0.010 g; 80%). NMR (CD$_3$COOD, 400 MHz) δ 3.10-3.30 (m, 2H), 4.15 (dd, 1H), 4.20 (s, 2H), 4.70 (s, 2H), 4.95 (dd, 1H), 5.20 (dt, 1H), 6.90-7.10 (m, 5H), 7.20-7.35 (m, 5H), 7.40-7.45 (m, 2H); m/z: 511.3 (M−1)⁻.

Example 30

3-(R)-4-(R)-1-(Phenyl)-3-[2-(thien-3-yl)-2-hydroxy-ethylsulphanyl]-4-{4-[N-((R)-α-{N-[(S)-1-(carboxy)-2-(hydroxy)ethyl]carbamoyl}benzyl)carbamoylmethoxy]phenyl}azetidin-2-one To a solution of 3-(R)-4-(R)-1-(phenyl)-3-(thien-3-ylcarbonylmethylsulphanyl)-4-{4-[N-(α-(R)-{N-[(S)-1-(carboxy)-2-(hydroxy)ethyl]carbamoyl}benzyl)carbamoylmethoxy]phenyl}azetidin-2-one (Example 28; 0.019 g, 0.028 mmol) in MeOH (3 ml) was added sodium borohydride (0.005 g, 0.132 mmol). After 10 minutes 0.1M ammonium acetate buffer (aq, 1 ml) was added and the solvent was removed under reduced pressure. The residue was purified by preparative HPLC using a gradient of 20-50% MeCN in 0.1M ammonium acetate buffer as eluent. After freeze-drying, the title compound was obtained as a white solid (0.015 g; 79%). NMR (CD$_3$COOD, 400 MHz) 3.05-3.30 (m, 2H), 3.85 (dd, 1H), 4.05 (dd, 1H), 4.15 (dd, 1H), 4.65-4.75 (m, 3H), 4.90 (dd, 1H), 5.15-5.25 (m, 1H), 5.95 (s, 1H), 6.90-7.10 (m, 5H), 7.20-7.50 (m, 12H); m/z 674.16 (m−H)⁻.

Example 31

1-(4-Fluorophenyl)-3-[2-(4-fluorophenylthio)ethyl]-4-{4-[N-((R)-α-{N-(S)-[1-(t-butoxycarbonyl)-2-(t-butoxy)ethyl]carbamoyl}benzyl)carbamoylmethoxy]phenyl}azetidin-2-one A solution of 1-(4-fluorophenyl)-3-[2-(4-fluorophenylthio)ethyl]-4-[4-(carboxymethoxy)phenyl]azetidin-2-one (Method 17; 0.100 g, 0.213 mmol), tert-butyl N-[(2R)-2-amino-2-phenylethanoyl]-O-(tert-butyl)-L-serinate (Method 6; 0.150 g, 0.428 mmol) and N-methylmorpholine (0.070 ml, 0.635 mmol) in DCM (4 ml) was stirred at room temperature for 10 minutes, after which TBTU (0.140 g, 0.436 mmol) was added. After 19 hours the solvent was removed under reduced pressure and the residue was purified by flash chromatography using heptane:EtOAc (2:1) as eluent to give a colourless oil (0.149 g; 87%). NMR (400 MHz) 0.90 (s, 9H), 1.45 (s, 9H), 2.05-2.30 (m, 2H), 2.95-3.15 (m, 2H), 3.20-3.25 (m, 1H), 3.30-3.35 (m, 1H), 3.65 (dd, 1H), 4.40-

4.60 (m, 3H), 4.60 (d, 1H), 5.50 (dd, 1H), 6.50 (dd, 1H), 6.85-7.00 (m, 6H), 7.15-7.40 (m, 11H), 7.90 (dd, 1H); m/z: 802.8.

Example 32

1-(4-Fluorophenyl)-3-[2-(4-fluorophenylthio)ethyl]-4-{4-[N-((R)-α-{N-(S)-[1-(carboxy-2-(hydroxy)ethyl]carbamoyl}benzyl)carbamoylmethoxy]phenyl}azetidin-2-one To a solution of 1-(4-fluorophenyl)-3-[2-(4-fluorophenylthio)ethyl]-4-{4-[N-((R)-α-{N-(S)-[1-(t-butoxycarbonyl)-2-(t-butoxy)ethyl]carbamoyl}benzyl)carbamoylmethoxy]phenyl}azetidin-2-one (Example 31; 0.149 g, 0.186 mmol) in DCM (3 ml) was added TFA (1.5 ml). After 20 hours, the solvent was removed under reduced pressure and the residue was purified by preparative HPLC using a gradient of 20-50% MeCN in 0.1M ammonium acetate buffer, as eluent. After freeze-drying, the title compound was obtained as a white solid (0.098 g; 77%). NMR (400 MHz) 2.00-2.25 (m, 2H), 2.85-3.10 (m, 2H), 3.10-3.20 (m, 1H), 3.35-3.45 (m, 1H), 3.75-3.85 (m, 1H), 4.15-4.45 (m, 3H), 4.55 (d, 1H), 5.70 (d, 1H), 6.70-7.00 (m, 6H), 7.10-7.35 (m, 11H), 7.45-7.55 (m, 1H), 8.45-8.55 (m, 1H); m/z: 690.5.

Example 33

1-(4-Fluorophenyl)-3-[2-(4-fluorophenylsulphinyl)ethyl]-4-{4-[N-((R)-α-55 N-(S)-1-(carboxy)-2-(hydroxy)ethyl]carbamoyl}benzyl)carbamoylmethoxy]phenyl}azetidin-2-one Example 34

1-(4-Fluorophenyl)-3-[2-(4-fluorophenylsulphonyl)ethyl]-4-{4-[N-((R)-α-{N-(S)-[1-(carboxy)-2-(hydroxy)ethyl]carbamoyl }benzyl)carbamoylmethoxy]phenyl}azetidin-2-one To a stirring suspension of 1-(4-fluorophenyl)-3-[2-(4-fluorophenylthio)ethyl]-4-{4-[N-((R)-α-{N-(S)-[1-(carboxy)-2-(hydroxy)ethyl]carbamoyl}benzyl)carbamoylmethoxy]phenyl }azetidin-2-one (Example 32; 0.070 g, 0.102 mmol) in DCM (5 ml) was added meta-chloroperoxybenzoic acid (0.035 g, 70-75%). After 20 hours, the solvent was removed under reduced pressure and the residue was purified by preparative HPLC using a gradient of 20-40% MeCN in 0.1M ammonium acetate buffer as eluent. After freeze-drying, 1-(4-fluorophenyl)-3-[2-(4-fluorophenylsulphinyl)ethyl]-4-{4-[N-((R)-α-{N-(S)-[1-(carboxy)-2-(hydroxy)ethyl]carbamoyl}benzyl)carbamoylmethoxy]phenyl}azetidin-2-one (0.022 g; 30%) NMR (CD$_3$COOD, 400 MHz) 2.15-2.45 (m, 2H), 3.10-3.35 (m, 3H), 3.85 (dd, 1H), 4.05 (dd, 1H), 4.65-4.75 (m, 3H), 4.80-4.90 (m, 1H), 5.90 (s, 1H), 6.95-7.05 (m. 4H), 7.25-7.50 (m, 11H), 7.70-7.80 (m, 2H); m/z: 706.2; and 1-(4-fluorophenyl)-3-[2-(4-fluorophenylsulphonyl) ethyl]-4-{4-[N-((R)-α-{N-(S)-[1-(carboxy)-2-(hydroxy)ethyl]carbamoyl}benzyl)carbamoylmethoxy]phenyl}azetidin-2-one (0.043 g; 59%) NM (CD$_3$COOD, 400 MHz) 2.25-2.40 (m, 2H), 3.25 (dt, 1H), 3.35-3.55 (m, 2H), 3.85 (dd, 1H), 4.05 (dd, 1H), 4.65-4.75 (m, 3H), 4.85 (d, 1H), 5.95 (s, 1H), 6.95-7.05 (m, 4H), 7.20-7.50 (m, 11H), 7.95-8.05 (m, 2H); m/z: 722.1 were obtained as a white solids.

Example 35

1-(4-Fluorophenyl)-3-[3-(4-fluorophenyl)-3-hydroxypropyl]-4-(4-{N-[(S)-α-(carboxy)benzyl]carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2, 49 mg, 0.105 mmol) was dissolved in a solution of N-methylmorpholine (35 µl, 0.318 mmol) in 2 ml DCM. (S)-Phenylglycine methyl ester hydrochloride (25 mg, 0.124 mmol) and TBTU (40 mg, 0.125 mmol) were added and the mixture was stirred at ambient temperature over night. The solution was diluted with 4 ml DCM and washed with 1% NaHCO$_3$, 0.1M KHSO$_4$ and brine. The organic phase was dried and evaporated to give the ester. M/z: 615. THF (2 ml), water (0.5 ml) and LiOH (ca 10 mg, 0.418 mmol) were added and the mixture was stirred over night. The solvent was removed and the residue was purified using preparative HPLC on a C8-column. A gradient from 20 to 50% MeCN in 0.1M ammonium acetate buffer was used as the mobile phase. Lyophilisation yielded a white solid. Mass: 40 mg (63%). M/z: 601. NMR (400 MHz, CD$_3$OD): 1.75-2.06 (m, 4H), 3.06-3.13 (m, 1H), 4.47-4.67 (m, 3H), 4.79-4.82 (m, 1H), 5.24 (d, 1H), 6.90-7.06 (m, 6H), 7.12-7.40 (m, 11H).

Example 36

1-(4-Fluorophenyl)-3-[3-(4-fluorophenyl)-3-hydroxypropyl]-4-[4-(N-{(R)-α-[N-((S)-1-carboxypropyl)carbamoyl]4-hydroxybenzyl}carbamoylmethoxy)phenyl]azetidin-2-one 1-(4-Fluorophenyl)-3-[3-(4-fluorophenyl)-3-hydroxypropyl]-4-(4-carboxymethoxyphenyl) azetidin-2-one (Method 2; 49 mg, 0.105 mmol) was dissolved in a solution of N-methylmorpholine (40 µl, 0.318 mmol) in 2 ml DCM. tert-Butyl (2S)-2-{[(2R)-2-amino-2-(4-hydroxyphenyl)acetyl]amino}butanoate hydrochloride (Method 14,43 mg, 0.125 mmol) and TBTU (40 mg, 0.125 mmol) were added. The mixture was stirred over night at ambient temperature. Additionally 10 mg (0.029 mmol) of the dipeptide was added and after 2 hours the solution was diluted with 4 ml DCM and washed with 1%NaHCO$_3$, 0.0M KHSO$_4$ and brine. The organic phase was dried and evaporated to give the ester. M/z: 758. Formic acid (1.5 ml) was added and the mixture was stirred over night. Additionally 1 ml formic acid was added. After 3 hours the formic acid was removed and MeOH (2 ml) together with Et$_3$N (40 µl, 0.288 mmol) were added and the mixture was stirred over night. The mixture was concentrated under reduced pressure and purified using preparative chromatography. A gradient from 20% to 80% MeCN in 0.1M ammonium acetate buffer was used as eluent. Lyophilisation yielded 42 mg (57%). NMR (400 MHz, DMSO-d$_6$): 0.65-0.72 (m, 3H), 1.53-1.67 (m, 1H), 1.74-2.04 (m, 5H), 3.06-3.14 (m, 1H), 4.18-4.23 (m, 1H), 4.50-4.66 (m, 3H), 4.77-4.82 (m, 1H), 5.46 (d, 1H), 6.72 (t, 2H), 6.93-7.06 (m, 6H), 7.18-7.36 (m, 8H); m/z: 702.

Example 37

1-(4-Fluorophenyl)-3-[3-(4-fluorophenyl)-3-hydroxypropyl]-4-{4-[N-(2-hydroxyethyl) carbamoylmethoxy]phenyl}azetidin-2-one 1-(4-Fluorophenyl)-3-[3-(4-fluorophenyl)-3-hydroxypropyl]-4-(4-carboxymethoxyphenyl)azetidin-2-one (Method 2, 20 mg, 0.043 mmol) was dissolved in a solution of N-methylmorpholine (10 µl, 0.091 mmol) in 2 ml DCM. 2-Aminoethanol (4 µl, 0.066 mmol) and TBTU (16 mg, 0.050 mmol) were added and the mixture was stirred for 3 hours. Additional 2-aminoethanol (3 µl) was added. The mixture was stirred for 2.5 days then concentrated and purified using preparative chromatography. A gradient from 20% to 50% MeCN in 0.1M ammonium acetate buffer was used as eluent. Lyophilisation yielded 10 mg (45%). NMR (400 MHz, CD$_3$OD): 1.75-2.06 (m, 4H), 3.05-3.12 (m, 1H), 3.38 (t, 2H), 3.61 (t, 2H), 4.51 (d, 2H), 4.574.66 (m, 1H), 4.774.83 (m, 1H), 6.93-7.07 (m, 6H), 7.22-7.37 (m, 6H); m/z: 511.

Example 38

1-(4-Fluorophenyl)-3-[3-(4-fluorophenyl)-3-hydroxypropyl]-4-{4-[N-(2-methoxyethyl) carbamoylmethoxy]phenyl }azetidin-2-one 1-(4-Fluorophenyl)-3-[3-(4-fluorophenyl)-3-hydroxypropyl]-4-(4-carboxymethoxyphenyl)azetidin-2-one (Method 2, 20 mg, 0.043 mmol) was dissolved in a solution of N-methylmorpholine (10 µl, 0.091 mmol) in 2 ml DCM. 2-Methoxyethylamine (5 µl, 0.058 mmol) and TBTU (16 mg, 0.050 mmol) were added and the mixture was stirred for 3 hours at ambient temperature. The mixture was concentrated and purified using preparative chromatography. A gradient from 20% to 50% MeCN in 0.1M ammonium acetate buffer was used as eluent. Lyophilisation yielded 5 mg (22%). NMR (400 MHz, CD$_3$OD): 1.75-2.05 (m, 4H), 3.05-3.15 (m, 1H), 3.29 (s, 3H), 3.40-3.44 (m, 4H), 4.5 (d, 2H), 4.57-4.66 (m, 1H), 4.78-4.82 (m, 1H), 6.92-7.06 (m, 6H), 7.22-7.37 (m, 6H); m/z: 525.

Example 39

1-(4-Fluorolphenyl)-3-[3-(4-fluorophenyl)-3-hydroxypropyl]-4-{4-[N-(2-sulphoethyl) carbamoylmethoxy]phenyl}azetidin-2-one TBTU (26 mg, 0.081 mmol) was added to a mixture of 1-(4-fluorophenyl)-3-[3-(4-fluorophenyl)-3-hydroxypropyl]-4-(4-carboxymethoxyphenyl)azetidin-2-one (Method 2; 29 mg, 0.062 mmol), taurine (24 mg, 0.19 mmol) and triethylamine (25 mg, 0.25 mmol) in MeCN (1 ml). After 1 hour DMF (1 ml) was added and the MeCN was removed in vacuo at 50° C. After 4 days at room temperature the mixture was purified by preparative HPLC using a gradient of MeCN/ammonium acetate buffer to give the title compound (2 mg, 6%). NMR (CD$_3$OD, 400 MHz) 7.40-7.20 (m, 6H), 7.05-6.95 (m, 6H), 4.8 (m, 1H), 4.7-4.55 (m, 1H), 4.5 (s, 2H), 3.75 (t, 2H), 3.1 (m, 1H), 2.95 (t, 2H), 2.0-1.8 (m, 4H).

Example 40

1-(4-Fluorophenyl)-3-[3-(4-fluorophenyl)-3-hydroxypropyl]-4-(4-{N-[(S)-1-(t-butoxycarbonyl)ethyl] carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), tert-butyl L-alaninate hydrochloride (40 mg, 0.22 mmol), triethyl amine (0.036 ml, 0.26 mmol) and TBTU (35 mg, 0.11 mmol) were mixed (in that order) in MeCN (1 ml). After 4 hours the mixture was diluted with toluene and the solution was washed with hydrochloric acid (2M) and sodium hydrogen carbonate solution. The solvent was removed in vacuo and the residue was purified by preparative HPLC using a gradient of MeCN/ammonium acetate buffer to give the title compound (20 mg, 52%). N (CD$_3$OD, 500 MHz) 7.40-6.90 (m), 4.8 (m), 4.7-4.3 (m), 3.95 (q), 3.2 (q), 3.1 (m), 2-1.8 (m), 1.5-1.3 (m); m/z 595.60 (M+H)$^+$ and 593.53 (M–H)$^-$.

Example 41

1-(4-Fluorophenyl)-3-[3-(4-fluorophenyl)-3-hydroxypropyl]-4-(4-{N-[(S)-1-(carboxy) ethyl] carbamoylmethoxy}phenyl)azetidin-2-one A solution of 1-(4-fluorophenyl)-3-[3-(4-fluorophenyl)-3-hydroxypropyl]-4-(4-{(N-[(S)-1-(t-butoxycarbonyl)ethyl] carbamoylmethoxy}phenyl)azetidin-2-one (Example 40; 20 mg, 0.034 mmol) in formic acid (1 ml) was kept at room temperature overnight. The formic acid was removed in vacuo and the residue was dissolved in methanol (4 ml). Aqueous ammonia (25%, 0.2 ml) was added and after 1 hour at room temperature the mixture was purified by preparative HPLC using a gradient of MeCN/ammonium acetate buffer to give the title compound (5 mg, 28%). NMR (CD$_3$OD, 400 MHz) 7.4-7.2 (m, 6H), 7.1-6.9 (m, 6H), 4,8 (m, 1H), 4.7-4.6 (m, 1H), 4.5 (s, 2H), 4.3 (q, 1H), 3.1 (m, 1H), 2-1.7 (m, 4H), 1.4 (dd, 3H); m/z 539.51 (M$^+$H)$^+$ and 537.50 (M–H)$^-$.

Example 42

1-(4-Fluorophenyl)-3-[3-(4-fluorophenyl)-3-hydroxypropyl]-4-[4-(N-{(R)-α-[N-(2-sulphoethyl)carbamoyl]-4-hydroxybenzyl}carbamoylmethoxy)phenyl] azetidin-2-one 1-(4-Fluorophenyl)-3-[3-(4-fluorophenyl)-3-hydroxypropyl]-4-(4-carboxymethoxyphenyl)azetidin-2-one (Method 2; 28 mg, 0.06 mmol), 2-{[(2R)-2-amino-2-(4-hydroxyphenyl) acetyl]amino}ethanesulfon acid (30 mg, 0.11 mmol), triethylamine (24 mg, 0.24 mmol), and TBTU (29 mg, 0.09 mmol) were mixed in DMF (1.5 ml). After stirring overnight the reaction mixture was purified by preparative IPLC using a gradient of MeCN/ammonium acetate buffer to give the title compound (18 mg, 42%). NMR (CD$_3$OD, 400 MHz) 7.4-7.1 (m), 7.1-6.9 (m), 5.4 (m), 4.8 (m), 4.7-4.5 (m), 3.65-3.55 (m), 3.15-3.05 (m), 3-2.8 (m), 2-1.7 (m); m/z 724.46 (M+H)$^+$ and 722.54 (M–H)$^-$.

Example 43

1-(4-Fluorophenyl)-3-[3-(4-fluorophenyl)-3-hydroxypropyl]-4-{4-[N-((S)-1-{N-[(S)-1-(t-butoxycarbonyl)ethyl]carbamoyl}ethyl)carbamoylmethoxy] phenyl}azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), tert-butyl L-alanyl-L-alaninate (25 mg, 0.12 mmol), triethylamine (0.036 ml, 0.26 mmol) and TBTU (31 mg, 0.10 mmol) were mixed (in that order) in DMF (1.5 ml). After 16 hours the mixture was diluted with toluene and the solution was washed with water, hydrochloric acid (2M), water and sodium hydrogen carbonate solution and water. Addition of IPA and removal of the solvents in vacuo gave the title compound. M/z 666.57 (M+H)$^+$ and 664.68 (M−H)$^-$.

Example 44

1-(4-Fluorophenyl)-3-[3-(4-fluorophenyl)-3-hydroxypropyl]-4-{4-[N-((S)-1-{N-[(S)-1-(carboxy)ethyl] carbamoyl}ethyl)carbamoylmethoxy] phenyl}azetidin-2-one 1-(4-Fluorophenyl)-3-[3-(4-fluorophenyl)-3-hydroxypropyl]-4-{4-[N-((S)-1-{N-[(S)-1-(t-butoxycarbonyl)ethyl] carbamoyl}ethyl)carbamoylmethoxy]phenyl}azetidin-2-one (Example 43; 54 mg, 0.081 mmol) was dissolved in formic acid (2 ml). After 16 hours the formic acid was removed in vacuo and the residue was dissolved in methanol (4 ml) and aqueous ammonia (25%, 0.2 ml). After 6 hours the mixture was purified by preparative HPLC using a gradient of MeCN/ammonium acetate buffer to give the title compound (15 mg, 30%). NMR (CD$_3$OD, 400 MHz) 7.4-7.2 (m, 6H), 7.1-6.9 (m, 6H), 4.8 (m, 1H), 4.7-4.5 (m, 1H), 4.5 (s, 2H), 4.45 (q, 1H), 4.3-4.2 (m, 1H), 3.2 (q, 1H), 3.1-3.0 (m, 1H), 2-1.8 (m, 4H), 1.4-1.2 (dd, 6H); m/z 610.57 (M$^+$H)$^+$ and 608.53 (m−H)$^-$.

Example 45

1-(4-Fluorophenyl)-3-[3-(4-fluorophenyl)-3-hydroxypropyl]-4-(4-{N-[N-(methoxycarbonylmethyl)carbamoylmethyl]carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), methyl glycylglycinate (19 mg, 0.13 mmol), triethyl amine (0.036 ml, 0.26 mmol) and TBTU (31 mg, 0.10 mmol) were mixed (in that order) in DMF (1.5 ml). After 16 hours the mixture was diluted with toluene and the solution was washed with water, hydrochloric acid (2M), water and sodium hydrogen carbonate solution and water. Addition of IPA and removal of the solvents in vacuo gave the title compound. M/z 596.50 (M+H)$^+$ and 594.45 (M−H)$^-$.

Example 46

1-(4-Fluorophenyl)-3-[3-(4-fluorophenyl)-3-hydroxypropyl]-4-(4-{N-[N-(carboxymethyl) carbamoylmethyl]carbamoylmethoxy}phenyl)azetidin-2-one A solution of 1-(4-fluorophenyl)-3-[3-(4-fluorophenyl)-3-hydroxypropyl]-4-(4-{N-[N-(methoxycarbonylmethyl)carbamoylmethyl]carbamoylmethoxy}phenyl)azetidin-2-one (Example 45; 44 mg, 0.074 mmol) in THF (4 ml) was added to a stirred solution of lithium hydroxide (10 mg, 0.43 mmol) in water (2 ml). After 16 hours the mixture was carefully neutralized with hydrochloric acid. Purification by preparative HPLC using a gradient of MeCN/ammonium acetate buffer gave the title compound (17 mg, 40%). NMR (CD$_3$OD, 400 MHz) 7.4-7.2 (m, 6H), 7.1-6.9 (m, 6H), 4.8 (m, 1H), 4.7-4.6 (m, 1H), 4.6 (s, 2H), 3.95 (s, 2H), 3.8 (s, 2H), 3.1-3.05 (m, 1H), 2-1.8 (m, 4H).

Example 47

1-(4-Fluorophenyl)-3-[3-(4-fluorophenyl)-3-hydroxypropyl]-4-(4-{N-[(S)-1,3-bis-(ethoxycarbonyl)propyl]carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), diethyl L-glutamate (19 mg, 0.093 mmol), triethylamine (0.036 ml, 0.26 mmol) and TBTU (31 mg, 0.10 mmol) were mixed (in that order) in DMN (1.5 ml). After 16 hours the mixture was diluted with toluene and the solution was washed with water, hydrochloric acid (2M), water and sodium hydrogen carbonate solution and water. Addition of IPA and removal of the solvents in vacuo gave the title compound. M/z 653.56 (M+H)$^+$ and 651.60 (M−H)$^-$.

Example 48

1-(4-Fluorophenyl)-3-[3-(4-fluorophenyl)-3-hydroxypropyl]-4-(4-{N-[(S)-1,3-bis-(carboxy) propyl] carbamoylmethoxy}phenyl)azetidin-2-one To a solution of 1-(4-fluorophenyl)-3-[3-(4-fluorophenyl)-3-hydroxypropyl]-4-(4-{N-[(S)-1,3-bis-(ethoxycarbonyl) propyl]carbamoylmethoxy}phenyl)azetidin-2-one (Example 47; 30 mg, 0.046 mmol) in ethanol (4 ml) was added 3.75 M sodium hydroxide solution (0.05 ml, 0.19 mmol). After 16 hours more 3.75M sodium hydroxide solution (0.05 ml, 0.19 mmol) was added. The ethanol was removed in vacuo and THF (2.5 ml) and water (1.5 ml) were added. After 24 hours the reaction mixture was purified by preparative HPLC using a gradient of MeCN/ammonium acetate buffer to give the title compound (11 mg, 40%). NMR (CD$_3$OD, 400 MHz) 7.5-6.9 (m), 5-4.8 (m), 4.75-4.6 (m), 4.5 (s), 4.45 (m), 4.4-4.3 (br s), 3.1-3.05 (m), 2.3-2.1 (m), 2-1.8 (m); m/z 597.52 (M+H)$^+$ and 595.49 (M−H)$^-$.

Example 49

1-(4-Fluorophenyl)-3-[3-(4-fluorophenyl)-3-hydroxypropyl]-4-(4-{N-[(S)-1-(t-butoxycarbonyl)-5-(t-butoxycarbonylamino)pentyl] carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), tert-butyl N$^6$-(tert-butoxycarbonyl)-L-lysinate (39 mg, 0.13 mmol), triethyl amine (0.036 ml, 0.26 mmol) and TBTU (31 mg, 0.096 mmol) were mixed in DMF (1.50 ml). The mixture was stirred for 16 hours and then diluted with water and toluene. The organic phase was washed with hydrochloric acid, water, sodium bicarbonate solution and then water. IPA was added to the organic phase and the solvents were removed in vacuo to give the title compound (39 mg, 81%). M/z 752.68 (M+H)$^+$ and 750.79 (M−H)$^-$.

Example 50

1-(4-Fluorophenyl)-3-[3-(4-fluorophenyl)-3-hydroxypropyl]-4-(4-{N-[(S)-1-(carboxy)-5-(amino)pentyl] carbamoylmethoxy}phenyl)azetidin-2-one 1-(4Fluorophenyl)-3-[3-(4-fluorophenyl)-3-hydroxypropyl]-4-(4-{N-[(S)-1-(t-butoxycarbonyl)-5-(t-butoxycarbonylamino)pentyl]carbamoylmethoxy}phenyl)azetidin-2-one (Example 49; 39 mg, 0.052 mmol) was kept in formic acid (2 ml) for 64 hours. The acid was removed in vacuo and the residue was dissolved in methanol (4 ml) and aqueous ammonia (25%, 0.4 ml). After 16 hours the solvent was removed in vacuo and the residue was purified by preparative HPLC using a gradient of MeCN/ammonium acetate buffer to give the title compound (7 mg, 23%). NMR (CD$_3$OD, 400 MHz) 7.4-7.2 (m, 6H), 7.05-6.95 (m, 6H), 4.8 (m, 1H), 4.65-4.6 (m, 1H), 4.5 (s, 2H), 4.35-4.3 (m, 1H), 3.1-3.05 (m, 1H), 2.9-2.8 (m, 2H), 2-1.6 (m, 6H), 1.5-1.2 (m, 4H).

Example 51

1-(4-Fluorophenyl)-3-[3-(4-fluorophenyl)-3-hydroxypropyl]-4-(4-{N-[2-(t-butoxycarbonyl)ethyl]carbamoylmethoxy}phenyl)azetidin-2-one A mixture of 1-(4-fluorophenyl)-3-[3-(4-fluorophenyl)-3-hydroxypropyl]-4-(4-carboxymethoxyphenyl)azetidin-2-one (Method 2; 47 mg, 0.101 mmol), tert-butyl β-alaninate (48 mg, 0.33 mmol), triethylamine (0.07 ml, 0.5 mmol), and TBTU (42 mg, 0.13 mmol) were mixed in DMF (1 ml) and left overnight. The mixture was diluted with diethyl ether and washed with potassium hydrogen sulphate solution and sodium carbonate solution. The organic phase was dried (magnesium sulphate) and the solvent was removed in vacuo to give the title compound (38 mg, 64%). M/z 595.54 (M+H)$^+$ and 593.61 (M−H)$^-$.

Example 52

1-(4-Fluorophenyl)-3-[3-(4-fluorophenyl)-3-hydroxypropyl]-4-(4-{N-[2-(carboxy)ethyl]carbamoylmethoxy}phenyl)azetidin-2-one 1-(4-Fluorophenyl)-3-[3-(4-fluorophenyl)-3-hydroxypropyl]-4-(4-{N-[2-(t-butoxycarbonyl)ethyl]carbamoylmethoxy}phenyl)azetidin-2-one (Example 51; 38 mg, 0.064 mmol) was dissolved in formic acid (2 ml). After 16 hours the acid was removed in vacuo with the aid of MeCN. After complete removal of the solvents the residue was dissolved in methanol (5 ml) and aqueous ammonia (25%, 1 ml). Hydrolysis was complete in 2 hours and purification by HPLC using a gradient of MeCN/ammonium acetate buffer gave the title compound (20 mg, 59%). NMR (CD$_3$OD, 400 MHz) 7.4-7.2 (m, 6H), 7.1-6.9 (m, 6H), 4.8 (m, 1H), 4.7-4.6 (m, 1H), 4.5 (s, 2H), 3.5 (t, 2H), 3.1-3.05 (m, 1H), 2.4 (t, 2H), 2-1.8 (m, 4H); m/z 539.42 (M+H)$^+$ and 537.50 (M−H)$^-$.

Example 53

1-(4-Fluorophenyl)-3-[3-(4-fluorophenyl)-3-hydroxypropyl]-4-(4-{N-[(R)-1-(t-butoxycarbonyl)ethyl]carbamoylmethoxy}phenyl)azetidin-2-one 1-(4-Fluorophenyl)-3-[3-(4-fluorophenyl)-3-hydroxypropyl]-4-(4-carboxymethoxyphenyl)azetidin-2-one (Method 2; 30 mg, 0.064 mmol), tert-butyl D-alaninate hydrochloride (50 mg, 0.28 mmol), triethylamine (0.05 ml, 0.36 mmol) and TBTU (31 mg, 0.096 mmol) were stirred in DMP (1 ml) for 3 hours. The mixture was diluted with toluene and washed with water, hydrochloric acid, water, sodium bicarbonate solution and water. IPA was added to the organic phase and the solvents were removed in vacuo to give 30 mg (79%) of the title compound. M/z 595.48 (M+H)$^+$ and 593.56 (M−H)$^-$.

Example 54

1-(4-Fluorophenyl)-3-[3-(4-fluorophenyl)-3-hydroxypropyl]-4-(4-{N-[(R)-1-(carboxy)ethyl]carbamoylmethoxy}phenyl)azetidin-2-one 1-(4-Fluorophenyl)-3-[3-(4-fluorophenyl)-3-hydroxypropyl]-4-(4-{N-[(R)-14-(t-butoxycarbonyl)ethyl]carbamoylmethoxy}phenyl)azetidin-2-one (Example 54; 30 mg, 0.05 mmol) was dissolved in formic acid (2 ml). After 16 hours the acid was removed in vacuo and the residue was dissolved in methanol (3 ml) and aqueous ammonia (25%, 0.2 ml). The progress was followed by HPLC and after completion the mixture was purified by HPLC using a gradient of MeCN/ammonium acetate buffer to give the title compound (17 mg, 63%). NMR (CD$_3$OD, 400 MHz) 7.4-7.2 (m, 6H), 7.1-6.9 (m, 6H), 4.8 (m, 1H), 4.7-4.6 (m, 1H), 4.5 (s, 2H), 4.3-4.2 (s, 1H), 3.1-3.05 (m, 1H), 2.2-1.8 (m, 4H), 1.5-1.4 (m, 3H).

Preparation of Starting Materials

The starting materials for the Examples above are either commercially available or are readily prepared by standard methods from known materials. For example, the following reactions are an illustration, but not a limitation, of some of the starting materials used in the above reactions.

Method 1

1-(4-Fluorophenyl)-3-[3-(4-fluorophenyl)-3-hydroxypropyl]-4-(4-t-butoxycarbonylmethoxy phenyl)azetidin-2-one 1-(4-Fluorophenyl)-3-[3-(4-fluorophenyl)-3-hydroxypropyl]-4-(4-hydroxyphenyl) azetidin-2-one (*J. Med. Chem.* 1998, 41, 973-980; 50 mg, 0.122 mmol), tert-butylbromoacetate (24 μl, 0.165 mmol), sodium carbonate (80 mg, 0.76 mmol) and a catalytic amount of caesium carbonate were added to MeCN (3 ml) and the mixture was stirred for 1.5 hours at 50° C. The solids were filtered off and the solvent was evaporated under reduced pressure. Purification of the residue by column chromatography using DCM/EtOAc (100/7) as eluent gave 35 mg, (55%) of the title compound. NMR (300 MHz): 1.45 (s, 9H), 1.8-2.1 (m, 4H), 2.25-2.3 (m, 1H), 3.05-3.15 (m, 1H), 4.5 (s, 2H), 4.55-4.6 (m, 1H), 4.75 (bs, 1H), 6.9-7.3 (m, 12H); m/z 524.3.

Method 2

1-(4-Fluorophenyl)-3-[3-(4-fluorophenyl)-3-hydroxypropyl]-4-(4-carboxymethoxyphenyl)azetidin-2-one 1-(4-Fluorophenyl)-3-[3-(4-fluorophenyl)-3-hydroxypropyl]-4-(4-t-butoxycarbonyl methoxyphenyl)azetidin-2-one (Method 1; 50 mg, 0.096 mmol) was added to formic acid (3 ml) and the mixture was stirred for 1.5 hours at room temperature. The solvent was evaporated under reduced pressure and methanol (3 ml) and triethylamine (150 μl) were added to the residue. The mixture was stirred for 2 hours at room temperature and the solvents were evaporated under reduced pressure. The residue was purified by preparative HPLC using MeCN/ammonium acetate buffer (35:65) as eluent. The collected fractions were lyophilised to obtain 32 mg (56%) of the title compound. NMR (300 MHz, CD$_3$OD): 1.8-1.95 (m, 4H), 3.1 (bs, 1H), 4.4 (s, 2H), 4.55-4.65 (m, 1H), 4.8 (bs, 1H), 6.9-7.35 (m, 12H); m/z 466.1 (M−H)$^-$.

Method 3 tert-Butyl N-((2R)-2-{[(benzyloxy)carbonyl]amino}-2-phenylethanoyl)glycinate (2R)-{[(benzyloxy)carbonyl]amino}(phenyl)acetic acid (Z-(R)-Phg-OH) (10 g, 35.0 mmol) and tert-butylglycine hydrochloride (6.3 g, 37.4 mmol) was dissolved in DCM (200 ml) with 2,6-lutidine (8.2 ml, 70.4 mmol). After stirring 5 minutes at 0° C. TBTU (12.4 g, 38.6 mmol) was added and stirring was continued 1 hours 30 minutes at 0° C. and 3 hours 45 minutes at room temperature. The reaction mixture was washed with water (2×100 ml), dried (magnesium sulphate) and purified with flash chromatography (DCM:EtOAc 7:1→5:1) to give the tide compound (13 g, 94%). NMR (500 MHz): 1.45 (s, 9 H), 3.84 (d, 1 H), 4.00 (dd, 1 H), 5.10 (m, 2 H), 5.28 (br s, 1 H), 6.13 (br s, 1 H), 6.23 (br s, 1 H), 7.30-7.44 (m, 10 H).

Method 4 tert-Butyl N-[(2R)-2-amino-2-phenylethanoyl]glycinate tert-Butyl N-((2R)-2-{[(benzyloxy)carbonyl]amino}-2-phenylethanoyl)glycinate (Method 3; 12.8 g, 32.2 mmol) was dissolved in EtOH (99%, 200 ml) and toluene (50 ml). Pd/C (10%, 0.65 g) was added and hydrogenation was performed at atmospheric pressure for 5 hours 30 minutes at room temperature. The reaction mixture was filtered through diatomaceous earth and the solvents were evaporated to give the title compound (8.4 g, 99%). NMR (600 MHz): 1.45 (s, 9 H), 3.93 (m, 2 H), 4.54 (s, 1 H), 7.31-7.42 (m, 5 H), 7.51 (br s, 1 H)

Method 5 tert-Butyl N-((2R)-2-{[(benzyloxy)carbonyl]amino}-2-phenylethanoyl)-O-(tert-butyl)-L-serinate (2R)-{[(Benzyloxy)carbonyl]amino}(phenyl)acetic acid (Z-(R)-Phg-OH) (2.0 g, 7.0 mmol) and tert-butyl O-(tert-butyl)-L-serinate (2.0 g, 7.9 mmol) and 2.6-lutidine were dissolved in DCM (30 ml). After stirring 5 minutes at 0° C. TBTU (2.5 g, 7.8 mmol) was added and stirring was continued 30 minutes at 0° C. and 4 hours at room temperature. The reaction mixture was washed with water (2×100 ml), dried and purified with flash chromatography (DCM) to give the title compound (3.3 g, 97%). NMR (300 MHz, CD$_3$OD): 1.05 (s, 9H), 1.45 (s, 9H), 3.4-3.8 (m, 2H), 4.5 (bs, 1H), 4.85 (s, 2H), 5.1 (s, 2H), 5.4 (s, 1H), 7.25-7.5 (m, 10 H).

Method 6 tert-Butyl N-[(2R)-2-amino-2-phenylethanoyl]-O-(tert-butyl)-L-serinate tert-Butyl N-((2R)-2-{[(benzyloxy)carbonyl]amino}-2-phenylethanoyl)-O-(tert-butyl)-L-serinate (Method 5; 3.3 g, 6.8 mmol) was dissolved in EtOH (95%, 30 ml) and a cat amount of Pd/C (5%)(50% in water) was added and hydrogenation was performed at atmospheric pressure for 3 hours at room temperature. The reaction mixture was filtered through diatomaceous earth and the solvent was evaporated to give the title compound (2.35 g, 98%). NMR (500 MHz, CD$_3$OD): 1.1 (s, 9H), 1.45 (s, 9H), 3.45-3.8 (m, 2H), 4.5 (t, 1H), 4.55 (s, 1H), 4.85 (s, 2H), 7.3-7.5 (m, 5H).

Method 7

1-(4-Fluorophenyl)-3-[2-(4-fluorophenoxy)ethyl]-4-[4-(t-butoxycarbonylmethoxy phenyl]azetidin-2-one A mixture of 1-(4-fluorophenyl)-3-[2-(4-fluorophenoxy) ethyl]-4-(4-hydroxyphenyl)azetidin-2-one (Prepared according to Bioorg. Med. Chem. Lett. 1996, 6, 1271-1274; 1.00 g, 2.53 mmol), t-butyl bromoacetate (0.42 ml, 2.79 mmol) and caesium carbonate (1.00 g, 3.07 mmol) in MeCN (10 ml) was stirred at 40° C. for 90 minutes. The suspension was filtered and the solid material was washed with MeCN (5 ml) and EtOAc (5 ml). The filtrate was concentrated and the residue was purified by flash chromatography using a mixture of hexane and EtOAc (7:2) as eluent. The title compound was obtained as a colourless oil (1.045 g; 81%). NMR (600 MHz) 1.45 (s, 9H), 2.25-2.45 (m, 2H), 3.20-3.30 (m, 1H), 4.00-4-10 (m, 1H), 4.10-4.20 (m, 1H), 4.50 (s, 2H), 4.80 (d, 1H), 6.75-7.00 (m, 8H), 5 7.20-7.30 (m, 4H); m/z: 501.2.

Method 8

1-(4-Fluorophenyl)-3-[2-(4-fluorophenoxy)ethyl]-4-[4-(carboxymethoxy)phenyl]azetidin-2-one A solution of 1-(4-fluorophenyl)-3-[2-(4-fluorophenoxy) ethyl]-4-[4-(t-butoxycarbonylmethoxy)phenyl]azetidin-2-one (Method 7; 1.045 g, 2.05.1 mmol) in formic acid (4 ml) was stirred at room temperature for 22 hours. The solvent was removed under reduced pressure and the residue was dissolved in DCM (10 ml). The organic layer was successively washed with a saturated solution of sodium hydrogen carbonate (aq; 5 ml), water (5 ml) and brine (5 ml), dried and concentrated to give the title compound as a white solid (0.941 g; ~quantitative yield). NMR (400 MHz) 2.25-2.45 (m, 2H), 3.20-3.30 (m, 1H), 4.00-4.20 (m, 2H), 4.65 (s, 2H), 4.80 (d, 1H), 6.75-6.80 (m, 2H), 6.85-7.00 (m, 6H), 7.20-7.30 (m, 4H); m/z: 454.0.

Method 9

3-(R)-4-(R)-1-(Phenyl)-3-(phenylethylsulphanyl)-4-[4-(carboxymethoxy)phenyl]azetidin-2-one 3-(R)-4-(R)-1-(Phenyl)-3-(phenylethylsulphanyl)-4-[4-(t-butoxycarbonylmethoxy) phenyl]azetidin-2-one (Method 15; 220 mg) was stirred in formic acid (2 ml) for 20 hours at ambient temperature. The formic acid was then evaporated. Toluene was added and evaporated twice to give the title compound (180 mg). NMR 400 MHz, CD$_3$OD): 2.86-3.00 (m, 4H), 4.03 (d, 1H), 4.66 (s, 2H), 4.87 (d, 1H), 6.93-7.35 (m, 14H).

Method 10

3-(R)-4-(R)-1-(Phenyl)-3-(4-fluorobenzoylmethylsulphanyl)-4-[4-(carboxymethoxy)phenyl]azetidin-2-one A solution of 3-(R)-4-(R)-1-(phenyl)-3-(4-fluorobenzoylmethylsulphanyl)-4-(4-hydroxyphenyl)azetidin-2-one (synthesized according to WO 96/16037; 0.100 g, 0.245 mmol), caesium carbonate (0.040 g, 0.123 mmol) and t-butyl bromoacetate (0.019 ml, 0.129 mmol) in MeCN (0.5 ml) was stirred at room temperature for 10 minutes, after which more caesium carbonate (0.040 g, 0.123 mmol) and t-butyl bromoacetate (0.019 ml, 0.129 mmol) were added. After 7 hours water (5 ml) and AcOH (0.05 ml) were added to the reaction mixture and the organic solvent was removed under reduced pressure. The water layer was extracted twice with DCM (2×5 ml) and the combined organic layers were washed with brine, dried over magnesium sulphate and concentrated. The residue was purified twice by flash chromatography using heptane:EtOAc (3:1) as eluent, which gave a colourless oil (0.066 g). M/z: 522.1. This oil was dissolved in formic acid (3 ml) and the solution was stirred at room temperature for 18 hours. The solvent was removed under reduced pressure and the residue was purified by preparative HPLC, using a gradient of 20-50% MeCN in 0.1M ammonium acetate buffer as eluent. The title compound was obtained as a white solid (0.025 g; 22%). NMR (CD$_3$COOD, 400 MHz) 4.20 (d, 1H), 4.25 (s, 2H), 4.70 (s, 2H), 5.00 (d, 1H), 6.90-7.10 (m, 2H), 7.00-7.40 (m, 9H), 8.00-8.10 (m, 2H); m/z: 465.9.

Method 11

3-(R)-4-(R)-1-(Phenyl)-3-(thien-3-ylcarbonylmethylsulphanyl)-4-[4-(carboxymethoxy) phenyl]azetidin-2-one A solution of 3-(R)-4-(R)-1-(phenyl)-3-(thien-3-ylcarbonylmethylsulphanyl)-4-(4-hydroxyphenyl)azetidin-2-one (synthesized according to WO 96/16037; 0.100 g, 0.253 mmol), caesium carbonate (0.043 g, 0.132 mmol) and t-butyl bromoacetate (0.019 ml, 0.126 mmol) in MeCN (6 ml) was stirred at room temperature for 10 minutes, after which more caesium carbonate (0.040 g, 0.123 mmol) and t-butyl bromoacetate (0.019 ml, 0.126 mmol) were added. After 7 hours water (7 ml) and AcOH (0.05 ml) were added and the solvent was removed under reduced pressure. The water layer was extracted twice with DCM (2×3 ml) and the combined organic layers were washed with brine, dried over magnesium sulphate and concentrated. The residue was purified by flash chromatography using heptane:EtOAc (3:1) as eluent, which gave 0.103 g of a colourless oil (m/z: 510.1). This oil was dissolved in formic acid (3 ml) and the solution was stirred for 18 hours at room temperature. The solvent was removed under reduced pressure and the residue was dissolved in DCM. The solution was washed two times with water and one time with brine, dried over magnesium sulphate and concentrated. This gave a colourless oil which was used without further purification (0.079 g). M/z: 453.9.

Method 12

1-(4-Fluorophenyl)-3-(2-chloroethyl)-4-(4-hydroxyphenyl) azetidin-2-one

A stirring mixture of 1-(4-fluorophenyl)-3-(2-chloroethyl)-4-[4-(benzyloxy)phenyl]azetidin-2-one (prepared according to Bioorg. Med. Chem. Lett. 1996, 6, 1271-1274; 2.00 g, 4.88 mmol), Pd(OH)$_2$/C (0.500 g, 20%) and cyclohexene (6 ml) in MeOH (60 ml) was heated to 70° C. After 2 hours, the reaction mixture was cooled to room temperature and was filtered through diatomaceous earth. The solvent was removed under reduced pressure to give the title compound (1.57 g; -quantitative yield). No further purification was necessary. NMR (CD$_3$OD, 400 MHz) 2.20-2.40 (m, 2H), 3.20-3.40 (m, 1H), 3.70 (t, 2H), 4.85 (d, 1H), 6.75-6.80 (m, 2H), 6.90-7.00 (m, 2H), 7.15-7.30 (m, 4H); m/z: 320.0.

Method 13

1-(4-Fluorophenyl)-3-[2-(4-fluorophenylthio)ethyl]-4-(4-hydroxyphenyl)azetidin-2-one To a stirring solution of 1-(4-fluorophenyl)-3-(2-chloroethyl)-4-(4-hydroxyphenyl)azetidin-2-one (Method 12; 0.750 g, 2.35 mmol) in MeCN (10 ml) was added 4-fluorothiophenol (0.500 ml, 4.60 mmol) and triethylamine (0.500 ml, 3.59 mmol) at room temperature. After 20 hours there were still start materiel left (approximately 20%, LC/MS) and more 4-fluorothiophenol (0.250 ml, 2.30 mmol) and triethylamine (0.170 ml, 1.22 mmol) were added. After 24 hours, the solvent was removed under reduced pressure and the residue was partitioned between water (20 ml) and EtOAc (20 ml). The organic layer was washed with brine (5 ml), dried over magnesium sulphate and concentrated. The residue was refluxed in heptane for 30 minutes before the title compound was filtered off as a grey solid (0.946 g; 98%). NMR (CD$_3$OD, 400 MHz) 2.00-2.20 (m, 2H), 3.05 (t, 2H), 3.25 (dt, 1H), 4.75 (d, 1H), 6.75-6.80 (m, 2H), 6.90-7.05 (m, 4H), 7.15-7.40 (m, 6H); m/z: 412.0.

Method 14 tert-Butyl (2S)-2-{[(2R)-2-amino-2-(4-hydroxyphenyl)acetyl]amino}butanoate hydrochloride tert-butyl (2S)-2-{[(2R)-2-{[(benzyloxy)carbonyl]amino}-2-(4-hydroxyphenyl)acetyl]amino}butanoate (Method 18, 47 g, 106.2 mmol) was dissolved in 400 ml 95.5% ethanol. Pd/C (5%, 3.0 g) was added and the mixture was hydrogenated under H$_2$(g) at 1 bar pressure at ambient temperature. The hydrogenation was terminated after 20 hours and the catalyst was filtered off on SiO$_2$ and washed with ethanol. The filtrate was concentrated and the residue (ca 35 g) was dissolved in 300 ml MeCN. Pyridine hydrochloride (14 g) was added and the mixture was left to crystallize for 2.5 days. The formed salt was filtered off and washed with 2×50 ml MeCN. The solid was dried under vacuum at 40° C. to yield 29.6 g (81%) of a white crystalline product. NMR (300 MHz, DMSO-d$_6$): 0.64 (t, 3H), 1.39 (s, 9H), 1.40-1.70 (m, 2H), 3.98-4.04 (m, 1H), 4.90 (brs, 1H), 6.78 (d, 2H), 7.32 (d, 2H), 8.63 (brs, 3H), 8.79 (d, 1H), 9.83 (brs, 1H).

Method 15

3-(R)-4-(R)-1-(Phenyl)-3-(phenylethylsulphanyl)-4-[4-(t-butoxycarbonylmethoxy) phenyl]azetidin-2-one A mixture of 3-R)-4-(R)-1-(phenyl)-3-(phenylethylsulphanyl)-4-(4-hydroxyphenyl)azetidin-2-one (synthesized according to WO 96/16037; 0.5 g, 1,33 mmol), t-butyl bromoacetate (0.31 g, 1.58 mmol), sodium carbonate (0.56 g, 5.28 mmol) and cesium carbonate (0.12 g, 0.36 mmol) in MeCN was stirred at 50° C. overnight. The reaction mixture was filtered and the solvent was removed under reduced pressure. The residue was purified by chromatography (EtOAc: isohexane, 1:6) to give the title compound 220 mg (33%). M/z 490.1.

Method 16

1-(4-Fluorophenyl)-3-[2-(4-fluorophenylthio)ethyl]-4-[4-(t-butoxycarbonylmethoxy)phenyl]azetidin-2-one A suspension of 1-(4-fluorophenyl)-3-[2-(4-fluorophenylthio)ethyl]-4-(4-hydroxyphenyl)azetidin-2-one (Method 13; 0.800 g, 1.944 mmol), t-butyl bromoacetate (0.32 ml, 2.17 mmol) and caesium carbonate (0.700 g, 2.15 mmol) in MeCN (15 ml) was stirred at room temperature for 2 hours. The solvent was removed under reduced pressure and the residue was partitioned between water (20 ml) and DCM (20 ml). The water layer was extracted once more with DCM (10 ml) and the combined organic layers were washed with brine, dried over magnesium sulphate and concentrated. The residue was purified by flash chromatography using heptane:EtOAc (4:1) as eluent The title compound was obtained as a colourless oil (0.884 g; 87%). NMR (400 MHz) 1.45 (s, 9H), 2.00-2.30 (m, 2H), 2.90-3.10 (m, 2H), 3.15-3.25 (m, 1H), 4.50 (s, 2H), 4.60 (d, 1H), 6.85-7.00 (m, 6H), 7.15-7.35 (m, 6H); m/z: 526.2.

Method 17

1-(4-Fluorophenyl)-3-[2-(4-fluorophenylthio)ethyl]-4-[4-(carboxymethoxy)phenyl]azetidin-2-one A solution of 1-(4-fluorophenyl)-3-[2-(4-fluorophenylthio)ethyl]-4-[4-(t-butoxycarbonylmethoxy)phenyl]azetidin-2-one (Method 16; 0.880 g, 1.67 mmol) in formic acid (5 ml) was stirred at room temperature for 19 hours. The solvent was removed under reduced pressure and the residue was dissolved in DCM (25 ml). The organic layer was washed twice with water (1×10 ml and 1×5 ml) and once with brine (5 ml), dried over magnesium sulphate and concentrated. This gave the title compound as a colourless oil (0.800 g; ~quantitative yield). NMR (CD$_3$COOD, 400 MHz) 2.10-2.30 (m, 2H), 3.10 (dt, 2H), 3.30-3.40 (m, 1H), 4.75 (s, 2H), 4.80 (d, 1H), 6.95-7.05 (m, 6H), 7.25-7.40 (m, 6H); m/z: 470.2.

Method 18 tert-Butyl (2S)-2-{[(2R)-2-{[(benzyloxy)carbonyl]amino}-2-(4-hydroxyphenyl)acetyl]amino}butanoate (R)-N-Benzyloxycarbonyl-4-hydroxyphenylglycine (J. Chem. Soc. Perkin Trans. 1, EN, 7, 1991, 1629-1635; 24.9 g, 82.6 mmol), (S)-2-aminobutyric acid t-butyl ester hydrochloride (18.6 g, 95.0 mmol) and N-methylmorpholine (23.0 g, 227.4 mmol) were dissolved in 220 ml DMF. TBTU (33.7 g, 105.0 mmol) was added in portions over 10 min. The reaction mixture was stirred for 1 hour at ambient temperature. Approximately 100 ml solvent was evaporated from the solution. Water (250 ml) was added to the remaining solution, which caused the product to precipitate. The mixture was left overnight then the solid was filtered off and washed with 30% methanol (200 ml) and hexane (100 ml). The solid was dispersed in 100 ml t-butyl methyl ether and stirred for 1 hour. The solid was filtered off, washed with t-butyl methyl ether (100 ml) and dried under vacuum at 40° C. to yield 34.7 g (95%). NMR (300 MHz, DMSO-$_6$): 0.71 (t, 3H), 1.37 (s, 9H), 1.40-1.70 (m, 2H), 3.91-4.01 (m, 1H), 5.02 (d, 2H), 5.23 (d, 1H), 6.67 (d, 2H), 7.22 (d, 2H), 7.27-7.36 (m, 5H), 7.67-7.74 (m, 1H), 8.32 (d, 1H), 9.37 (brs, 1H).

The invention claimed is:

1. A compound of formula (I):

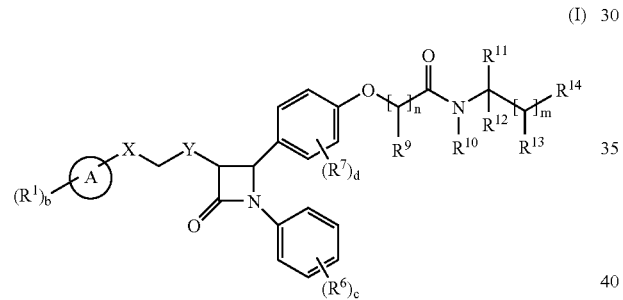

wherein:

Ring A is selected from phenyl or thienyl;

X is selected from —$CR^2R^3$—, —O—, —$NR^x$— and —$S(O)_a$—; wherein $R^x$ is hydrogen or $C_{1-6}$alkyl, and a is 0-2;

Y is selected from —$CR^4R^5$—, —O—, —$NR^z$— and —$S(O)_a$—; wherein $R^z$ is hydrogen or $C_{1-6}$alkyl, and a is 0-2; wherein there is at least one —$CR^2R^3$— or —$CR^4R^5$— group;

$R^1$ is independently selected from halo, hydroxy, $C_{1-6}$alkyl, $C_{1-6}$alkoxy and $C_{1-6}$alkylS(O)$_a$ wherein a is 0 to 2; wherein $R^1$ is independently optionally substituted on carbon by one or more halo, $C_{1-6}$alkoxy and hydroxy;

b is 0-3; wherein the values of $R^1$ may be the same or different;

$R^2$ and $R^3$ are independently selected from hydrogen, hydroxy, $C_{1-6}$alkyl, $C_{1-6}$alkoxy and $C_{1-6}$alkanoyloxy; wherein $R^2$ and $R^3$ may be independently optionally substituted on carbon by one or more halo or hydroxy; or $R^2$ and $R^3$ together form an oxo group;

$R^4$ and $R^5$ are independently selected from hydrogen, hydroxy, $C_{1-6}$alkyl, $C_{1-6}$alkoxy and $C_{1-6}$alkanoyloxy; or $R^4$ and $R^5$ together form an oxo group;

$R^6$ is independently selected from halo, nitro, cyano, hydroxy, amino, carboxy, formyl, carbamoyl, carbamoyloxy, mercapto, sulphamoyl, $C_{1-6}$alkyl, $C_{2-6}$alkenyl, $C_{2-6}$alkenyloxy, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, $C_{1-6}$alkanoyl-N-($C_{1-6}$alkyl)amino, $C_{1-6}$alkylsulphonylamino, $C_{1-6}$alkylsulphonyl-N-($C_{1-6}$alkyl)amino, N-($C_{1-6}$alkyl)carbamoyl, N,N-($C_{1-6}$alkyl)$_2$carbamoyl, N-($C_{1-6}$alkyl)carbamoyloxy, N,N-($C_{1-6}$alkyl)$_2$carbamoyloxy, $C_{1-6}$alkylS(O)$_a$ wherein a is 0 to 2, $C_{1-6}$alkoxycarbonyl, $C_{1-6}$alkoxycarbonylamino, $C_{1-6}$alkoxycarbonyl-N-($C_{1-6}$alkyl)amino, $C_{1-6}$alkoxycarbonyloxy, $C_{1-6}$alkoxycarbonylamino, ureido, N'-($C_{1-6}$alkyl)ureido, N-($C_{1-6}$alkyl)ureido, N',N'-($C_{1-6}$alkyl)$_2$ureido, N'-($C_{1-6}$alkyl)-N-($C_{1-6}$alkyl)ureido, N',N'-($C_{1-6}$alkyl)$_2$-N-($C_{1-6}$alkyl)ureido, N-($C_{1-6}$alkyl)sulphamoyl, N,N-($C_{1-6}$alkyl)$_2$sulphamoyl and phenyl; wherein $R^7$ is independently optionally substituted on carbon by one or more halo, $C_{1-6}$alkoxy, hydroxy, amino, carboxy, $C_{1-6}$alkoxycarbonyl, carbamoyl, N-($C_{1-6}$alkyl)carbamoyl, N,N-($C_{1-6}$alkyl)$_2$carbamoyl, $C_{1-6}$alkanoylamino, $C_{1-6}$alkanoyl-N-($C_{1-6}$alkyl)amino, phenyl, phenoxy, benzoyl, phenyl$C_{1-6}$alkyl and phenyl$C_{1-6}$alkoxy;

c is 0-5; wherein the values of $R^6$ may be the same or different;

$R^7$ is independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

d is 0-4; wherein the values of $R^7$ may be the same or different;

$R^9$ is hydrogen, $C_{1-4}$alkyl, carbocyclyl or heterocyclyl; wherein $R^9$ may be optionally substituted on carbon by one or more substituents selected from $R^{23}$; and wherein if said heterocyclyl contains an —NH— group, that nitrogen may be optionally substituted by a group selected from $R^{24}$;

$R^{10}$ is hydrogen or $C_{1-4}$alkyl;

$R^{11}$ and $R^{12}$ are independently selected from hydrogen, $C_{1-4}$alkyl, carbocyclyl or heterocyclyl; or $R^{11}$ and $R^{12}$ together form $C_{2-6}$alkylene; wherein $R^{11}$ and $R^{12}$ or $R^{11}$ and $R^{12}$ together may be independently optionally substituted on carbon by one or more substituents selected from $R^{25}$; and wherein if said heterocyclyl contains an —NH— moiety, that nitrogen may be optionally substituted by one or more $R^{26}$;

$R^{13}$ is hydrogen, $C_{1-4}$alkyl, carbocyclyl or heterocyclyl; wherein $R^{13}$ may be optionally substituted on carbon by one or more substituents selected from $R^{27}$; and wherein if said heterocyclyl contains an —NH— moiety, that nitrogen may be optionally substituted by one or more $R^{28}$;

$R^{14}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_e$-$R^{29}$—($C_{1-10}$alkylene)$_f$-, heterocyclyl-($C_{1-10}$alkylene)$_g$-$R^{30}$—($C_{1-10}$alkylene)$_h$-, carboxy, sulpho, sulphino, phosphono, —P(O)(O$R^{31}$)(O$R^{32}$), —P(O)(OH)(O$R^{31}$), —P(O)(OH)($R^{31}$) or —P(O)(O$R^{31}$)($R^{32}$) wherein $R^{31}$ and $R^{32}$ are independently selected from $C_{1-6}$alkyl; wherein $R^{14}$ may be optionally substituted on carbon by one or more substituents selected from $R^{33}$; and wherein if said heterocyclyl contains an —NH— group, that nitrogen may be optionally substituted by a group selected from $R^{34}$; or $R^{14}$ is a group of formula (IA):

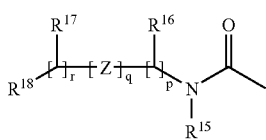

(IA)

wherein:

Z is —N($R^{35}$)—, —N($R^{35}$)C(O)—, —O—, and —S(O)$_a$—; wherein a is 0-2 and $R^{35}$ is hydrogen or $C_{1-4}$alkyl;

$R^{15}$ is hydrogen or $C_{1-4}$alkyl;

$R^{16}$ and $R^{17}$ are independently selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl, heterocyclyl, sulpho, sulphino, amidino, phosphono, —P(O)(O$R^{36}$)(O$R^{37}$), —P(O)(OH)(O$R^{36}$), —P(O)(OH)($R^{36}$) or —P(O)(O$R^{36}$)($R^{37}$), wherein $R^{36}$ and $R^{37}$ are independently selected from $C_{1-6}$alkyl; wherein $R^{16}$ and $R^{17}$ may be independently optionally substituted on carbon by one or more substituents selected from $R^{38}$; and wherein if said heterocyclyl contains an —NH— group, that nitrogen may be optionally substituted by a group selected from $R^{39}$;

$R^{18}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, $C_{1-10}$alkoxycarbonyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, carbocyclyl, carbocyclyl$C_{1-10}$alkyl, heterocyclyl, heterocyclyl$C_{1-10}$alkyl, carbocyclyl-($C_{1-10}$alkylene)$_e$-$R^{40}$—($C_{1-10}$alkylene)$_f$- or heterocyclyl-($C_{1-10}$alkylene)$_g$-$R^{41}$—($C_{1-10}$alkylene)$_h$-, carboxy, sulpho, sulphino, phosphono, —P(O)(O$R^{42}$)(O$R^{43}$), —P(O)(OH)(O$R^{42}$), —P(O)(OH)($R^{42}$) or —P(O)(O$R^{42}$)($R^{43}$) wherein $R^{42}$ and $R^{43}$ are independently selected from $C_{1-6}$alkyl; wherein $R^{18}$ may be optionally substituted on carbon by one or more substituents selected from $R^{44}$; and wherein if said heterocyclyl contains an —NH— group, that nitrogen may be optionally substituted by a group selected from $R^{45}$; or $R^{18}$ is a group of formula (IB):

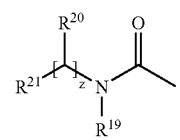

(IB)

wherein:

$R^{19}$ is selected from hydrogen or $C_{1-4}$alkyl;

$R^{20}$ is selected from hydrogen, halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, carbocyclyl, heterocyclyl, sulpho, sulphino, amidino, phosphono, —P(O)(O$R^{46}$)(O$R^{47}$), —P(O)(OH)(O$R^{46}$), —P(O)(OH)($R^{46}$) or —P(O)(O$R^{46}$)($R^{47}$), wherein $R^{46}$ and $R^{47}$ are independently selected from $C_{1-6}$alkyl; where $R^{20}$ may be independently optionally substituted on carbon by one or more substituents selected from $R^{48}$; and wherein if said heterocyclyl contains an —NH— group, that nitrogen may be optionally substituted by a group selected from $R^{49}$;

$R^{21}$ is selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N-($C_{1-10}$alkyl)amino, N,N-($C_{1-10}$alkyl)$_2$amino, $C_{1-10}$alkanoylamino, N-($C_{1-10}$alkyl)carbamoyl, N,N-($C_{1-10}$alkyl)$_2$carbamoyl, $C_{1-10}$alkylS(O)$_a$ wherein a is 0 to 2, N-($C_{1-10}$alkyl)sulphamoyl, N,N-($C_{1-10}$alkyl)$_2$sulphamoyl, N-($C_{1-10}$alkyl)sulphamoylamino, N,N-($C_{1-10}$alkyl)$_2$sulphamoylamino, $C_{1-10}$alkoxycarbonylamino, carbocyclyl, carbocyclyl$C_{1-10}$alkyl, heterocyclyl, heterocyclyl$C_{1-10}$alkyl, carbocyclyl-($C_{1-10}$alkylene)$_e$-$R^{50}$—($C_{1-10}$alkylene)$_f$-, heterocyclyl-($C_{1-10}$alkylene)$_g$-$R^{51}$—($C_{1-10}$alkylene)$_h$-, carboxy, sulpho, sulphino, phosphono, —P(O)(O$R^{52}$)(O$R^{53}$), —P(O)(OH)(O$R^{52}$), —P(O)(OH)($R^{52}$) or —P(O)(O$R^{53}$)($R^{53}$) wherein $R^{52}$ and $R^{53}$ are independently selected from $C_{1-6}$alkyl; wherein $R^{21}$ may be independently optionally substituted on carbon by one or more $R^{54}$; and wherein if said heterocyclyl contains an —NH— group, that nitrogen may be optionally substituted by a group selected from $R^{55}$;

p is 1-3; wherein the values of $R^{16}$ may be the same or different;

q is 0-1;

r is 0-3; wherein the values of $R^{17}$ may be the same or different;

m is 0-2; wherein the values of $R^{13}$ may be the same or different;

n is 1-2; wherein the values of $R^{9}$ may be the same or different;

z is 0-3; wherein the values of $R^{20}$ may be the same or different;

$R^{23}$, $R^{25}$, $R^{27}$, $R^{33}$, $R^{38}$, $R^{44}$, $R^{48}$ and $R^{54}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, $C_{1-10}$alkoxycarbonyl, N-($C_{1-10}$alkyl)amino, N,N-($C_{1-10}$ alkyl)$_2$amino, C$_{1-10}$alkanoylamino, N-(C$_{1-10}$alkyl)carbamoyl, N,N-(C$_{1-10}$alkyl)$_2$carbamoyl, C$_{1-10}$alkylS(O)$_a$ wherein a is 0 to 2, N-(C$_{1-10}$alkyl)sulphamoyl, N,N-(C$_{1-10}$alkyl)$_2$sulphamoyl, N-(C$_{1-10}$alkyl)sulphamoylamino, N,N-(C$_{1-10}$alkyl)$_2$sulphamoylamino, C$_{1-10}$alkoxycarbonylamino, carbocyclyl, carbocyclylC$_{1-10}$alkyl, heterocyclyl, heterocyclylC$_{1-10}$alkyl, carbocyclyl-(C$_{1-10}$alkylene)$_e$-R$^{56}$—(C$_{1-10}$alkylene)$_f$-, heterocyclyl-(C$_{1-10}$alkylene)$_g$-R$^{57}$—(C$_{1-10}$alkylene)$_h$-, carboxy, sulpho, sulphino, amidino, phosphono, —P(O)(OR$^{58}$)(OR$^{59}$), —P(O)(OH)(OR$^{58}$), —P(O)(OH)(R$^{58}$) or —P(O)(OR$^{59}$)(R$^{59}$), wherein R$^{58}$ and R$^{59}$ are independently selected from C$_{1-6}$alkyl; wherein R$^{23}$, R$^{25}$, R$^{27}$, R$^{33}$, R$^{38}$, R$^{44}$, R$^{48}$ and R$^{54}$ may be independently optionally substituted on carbon by one or more R$^{60}$; and wherein if said heterocyclyl contains an —NH— group, that nitrogen may be optionally substituted by a group selected from R$^{61}$;

R$^{24}$, R$^{26}$, R$^{28}$, R$^{34}$, R$^{39}$, R$^{45}$, R$^{49}$, R$^{55}$ and R$^{61}$ are independently selected from C$_{1-6}$alkyl, C$_{1-6}$alkanoyl, C$_{1-6}$alkylsulphonyl, sulphamoyl, N-(C$_{1-6}$alkyl)sulphamoyl, N,N-(C$_{1-6}$alkyl)$_2$sulphamoyl, C$_{1-6}$alkoxycarbonyl, carbamoyl, N-(C$_{1-6}$alkyl)carbamoyl, N,N-(C$_{1-6}$alkyl)$_2$carbamoyl, benzyl, phenethyl, benzoyl, phenylsulphonyl and phenyl;

R$^{29}$, R$^{30}$, R$^{40}$, R$^{41}$, R$^{50}$, R$^{51}$, R$^{56}$ and R$^{57}$ are independently selected from —O—, —NR$^{62}$—, —S(O)$_x$—, —NR$^{62}$C(O)NR$^{63}$—, —NR$^{62}$C(S)NR$^{63}$—, —OC(O)N=C—, —NR$^{62}$C(O)— or —C(O)NR$^{62}$—; wherein R$^{62}$ and R$^{63}$ are independently selected from hydrogen or C$_{1-6}$alkyl, and x is 0-2;

R$^{60}$ is selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2; or a pharmaceutically acceptable salt, or a prodrug thereof.

2. A compound of formula (I) according to claim 1 wherein X is selected from —CH$_2$—, —CH(OH)—, —C(O)—, —O— —S—, —S(O)— and —S(O)$_2$—; or a pharmaceutically acceptable salt, or a prodrug thereof.

3. A compound of formula (I) according to claim 1 wherein Y is —CH$_2$—, —S— or —S(O)—; or a pharmaceutically acceptable salt, or a prodrug thereof.

4. A compound of formula (I) according to any one of claims 1 to 3 wherein R$^1$ is halo; or a pharmaceutically acceptable salt, or a prodrug thereof.

5. A compound of formula (I) according to any one of claims 1 to 3 wherein b is 0-1; or a pharmaceutically acceptable salt, or a prodrug thereof.

6. A compound of formula (I) according to any one of claims 1 to 3 wherein R$^6$ is halo; or a pharmaceutically acceptable salt, or a prodrug thereof.

7. A compound of formula (I) according to any one of claims 1 to 3 wherein c is 0-1; or a pharmaceutically acceptable salt, or a prodrug thereof.

8. A compound of formula (I) according to any one of claims 1 to 3 wherein d is 0; or a pharmaceutically acceptable salt, or a prodrug thereof.

9. A compound of formula (I) according to any one of claims 1 to 3 wherein R$^9$ is hydrogen; or a pharmaceutically acceptable salt, or a prodrug thereof.

10. A compound of formula (I) according to any one of claims 1 to 3 wherein R$^{10}$ is hydrogen; or a pharmaceutically acceptable salt, or a prodrug thereof.

11. A compound of formula (I) according to any one of claims 1 to 3 wherein R$^{11}$ and R$^{12}$ are independently selected from hydrogen, C$_{1-4}$alkyl or carbocyclyl; wherein R$^{11}$ and R$^{12}$ may be independently optionally substituted on carbon by one or more substituents selected from R$^{25}$; wherein R$^{25}$ is selected from hydroxy, amino, carbamoyl, C$_{1-10}$alkoxycarbonyl, C$_{1-10}$alkoxycarbonylamino, carbocyclyl or carboxy; wherein R$^{25}$ may be optionally substituted on carbon by one or more R$^{60}$; wherein R$^{60}$ is hydroxy; or a pharmaceutically acceptable salt, or a prodrug thereof.

12. A compound of formula (I) according to any one of claims 1 to 3 wherein R$^{13}$ is hydrogen; or a pharmaceutically acceptable salt, or a prodrug thereof.

13. A compound of formula (I) according to any one of claims 1 to 3 wherein R$^{14}$ is hydroxy, C$_{1-10}$alkyl, C$_{1-10}$alkoxy, C$_{1-10}$alkoxycarbonyl, carboxy or sulpho; wherein R$^{14}$ may be optionally substituted on carbon by one or more substituents selected from R$^{33}$; or R$^{14}$ is a group of formula (IA) (as depicted above in claim 1) wherein:

R$^{15}$ hydrogen;

R$^{16}$ and R$^{17}$ are independently selected from hydrogen, carboxy, C$_{1-6}$alkyl and C$_{1-6}$alkoxycarbonyl;

R$^{18}$ is selected from hydroxy, C$_{1-10}$alkyl, C$_{1-10}$alkoxy, C$_{1-10}$alkoxycarbonyl, carboxy and sulpho;

p is 1;

q is 0;

r is 0 or 1;

m is 0 or 1;

n is 1; and

R$^{33}$ is hydroxy; or a pharmaceutically acceptable salt, or a prodrug thereof.

14. A compound of formula (I) according to any one of claims 1 to 3 wherein m is 0 or 1; or a pharmaceutically acceptable salt, or a prodrug thereof.

15. A compound of formula (I) according to any one of claims 1 to 3 wherein n is 1; or a pharmaceutically acceptable salt, or a prodrug thereof.

16. A compound of formula (I) (as depicted in claim 1) wherein:

Ring A is selected from phenyl or thienyl;

X is selected from —CH$_2$—, —CH(OH)—, —C(O)—, —O— —S—, —S(O)— and —S(O)$_2$—;

Y is —CH$_2$—, —S— or —S(O)—;

R$^1$ is fluoro;

b is 0-1;

R$^6$ is fluoro;

c is 0-1;

d is 0;

R$^9$ hydrogen;

R$^{10}$ hydrogen;

One of R$^{11}$ and R$^{12}$ is hydrogen and the other is selected from hydrogen, methyl, hydroxymethyl, 2-carbamoylethyl, 2-(ethoxycarbonyl)ethyl, 2-carboxyethyl, 4-(t-butoxycarbonylamino)butyl, 4-aminobutyl, isobutyl, phenyl, 4-hydroxyphenyl and 4-hydroxybenzyl;

R$^{13}$ is hydrogen;

$R^{14}$ is hydroxy, pentyl, methoxy, ethoxycarbonyl, t-butoxycarbonyl, carboxy or sulpho; wherein $R^{14}$ may be optionally substituted on carbon by one or more substituents selected from $R^{33}$; or $R^{14}$ is a group of formula (IA) (as depicted above) wherein:

$R^{15}$ hydrogen;

$R^{16}$ and $R^{17}$ are independently selected from hydrogen, carboxy, $C_{1-6}$alkyl and t-butoxycarbonyl;

$R^{18}$ is selected from hydroxy, methyl, t-butoxy, ethoxycarbonyl, t-butoxycarbonyl, carboxy and sulpho;

p is 1;

q is 0;

r is 0 or 1;

m is 0 or 1;

n is 1; and $R^{33}$ is hydroxy; or a pharmaceutically acceptable salt, or a prodrug thereof.

17. A compound of formula (I) (as depicted in claim 1) selected from:

- 1-(4-fluorophenyl)-3-[3-(4-fluorophenyl)-3-hydroxypropyl]-4-{4-[N-((R)-α-{N-(S)-[1-(carboxy)-2-(hydroxy)ethyl]carbamoyl}benzyl)carbamoylmethoxy]phenyl}azetidin-2-one;
- 1-(4-fluorophenyl)-3-[3-(4-fluorophenyl)-3-hydroxypropyl]-4-(4-{N-[(R)-α-(carboxy) benzyl]carbamoylmethoxy}phenyl)azetidin-2-one;
- 1-(4-fluorophenyl)-3-[3-(4-fluorophenyl)-3-hydroxypropyl]-4-{4-[N-(carboxymethyl) carbamoylmethoxy]phenyl}azetidin-2-one;
- 1-(4-fluorophenyl)-3-[3-(4-fluorophenyl)-3-hydroxypropyl]-4-(4-{N-[N-(carboxymethyl) carbamoylmethyl] carbamoylmethoxy}phenyl)azetidin-2-one;
- 1-(4-fluorophenyl)-3-[3-(4-fluorophenyl)-3-hydroxypropyl]-4-{4-[N-(2-hydroxyethyl) carbamoylmethoxy]phenyl}azetidin-2-one;
- 1-(4-fluorophenyl)-3-[3-(4-fluorophenyl)-3-hydroxypropyl]-4-{4-[N-(2-methoxyethyl) carbamoylmethoxy]phenyl}azetidin-2-one;
- 3-(R)-4-(R)-1-(phenyl)-3-(4-fluorobenzoylmethylsulphanyl)-4-{4-[N-(carboxymethyl) carbamoylmethoxy]phenyl}azetidin-2-one;
- 3-(R)-4-(R)-1-(phenyl)-3-[2-(4-fluorophenyl)-2-hydroxyethylsulphanyl]-4-{4-[N-(carboxymethyl)carbamoylmethoxy]phenyl}azetidin-2-one;
- 3-(R)-4-(R)-1-(phenyl)-3-[2-(thien-3-yl)-2-hydroxyethylsulphanyl]-4-{4-[N-(cabroxymethyl) carbamoylmethoxy]phenyl}azetidin-2-one;
- 3-(R)-4-(R)-1-(phenyl)-3-[2-(thien-3-yl)-2-hydroxyethylsulphanyl]-4-{4-[N-((R)-α-{N-[(S)-1-(carboxy)-2-(hydroxy)ethyl]carbamoyl}benzyl)carbamoylmethoxy]phenyl}azetidin-2-one;
- 3-(R)-4-(R)-1-(phenyl)-3-(4-fluorobenzoylmethylsulphanyl)-4-(4-[N-((R)-α-{N-[(S)-1-(carboxy)-2-(hydroxy)ethyl]carbamoyl}benzyl)carbamoylmethoxy]phenyl}azetidin-2-one; and
- 3-(R)-4-(R)-1-(phenyl)-3-[2-(4-fluorophenyl)-2-hydroxyethylsulphanyl]-4-{4-[N-((R)-α{N-[(S)-1-(carboxy)-2-(hydroxy)ethyl]carbamoyl}benzyl)carbamoylmethoxy]phenyl}azetidin-2-one;

or a pharmaceutically acceptable salt, or a prodrug thereof.

18. A process for preparing a compound of formula (I) or a pharmaceutically acceptable salt, or a prodrug thereof which process (wherein variable groups are, unless otherwise specified, as defined in claim 1) comprises of:

Process 1) reacting a compound of formula (II):

with a compound of formula (III):

wherein L is a displaceable group;

Process 2) reacting an acid of formula (IV):

or an activated derivative thereof; with an amine of formula (V):

Process 3): for compounds of formula (I) wherein $R^{14}$ is a group of formula (IA); reacting a compound of formula (VI) wherein $R^{14}$ is carboxy, or an activated derivative thereof, with an amine of formula (VI):

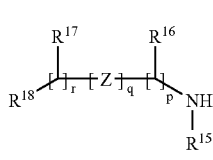

(VI)

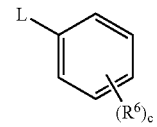

(XI)

Process 4): for compounds of formula (I) wherein $R^{14}$ is a group of formula (IA), Z is —N($R^{35}$)C(O)— and q is 1; reacting an acid of formula (VII):

wherein L is a displaceable group;

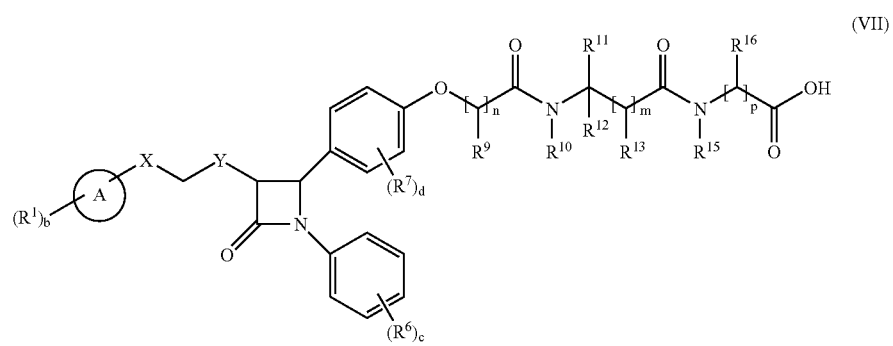

(VII)

or an activated derivative thereof with an amine of formula (VIII):

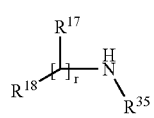

(VIII)

Process 7): for compounds of formula (I) wherein X is selected from —O—, —NR$^x$— and —S(O)$_a$— wherein a is 0; reacting a compound of formula (XII):

Process 5): for compounds of formula (I) wherein $R^{14}$ is a group of formula (IA) and $R^{18}$ is a group of formula (IB); reacting an acid of formula (I) wherein $R^{14}$ is a group of formula (IA) and $R^{18}$ is carboxy, or an activated derivative thereof, with an amine of formula (IX)

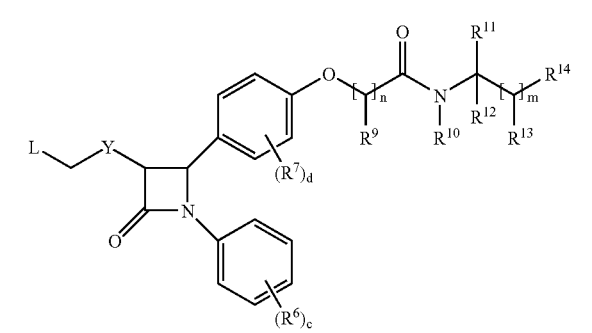

(XII)

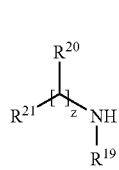

(IX)

Process 6): reacting a compound of formula (X):

wherein L is a displaceable group; with a compound of formula (XIII):

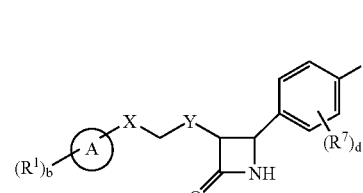

(X)

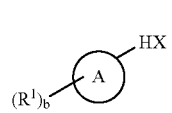

(XIII)

Process 8): for compounds of formula (I) wherein X is selected from —O—, —NR$^x$— and —S(O)$_a$— wherein a is 0; reacting a compound of formula (XIV):

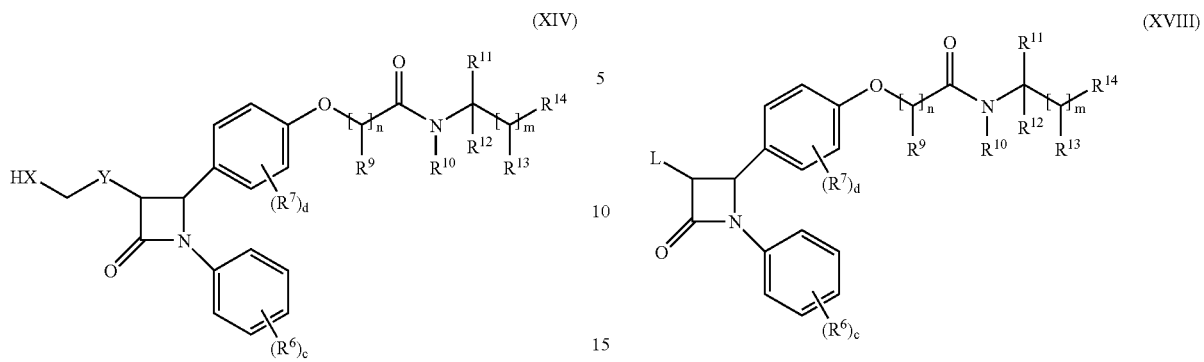

with a compound of formula (XV):

wherein L is a displaceable group;

Process 9): for compounds of formula (I) wherein Y is selected from —O—, —NR$^z$— and —S(O)$_a$— wherein a is 0; reacting a compound of formula (XVI):

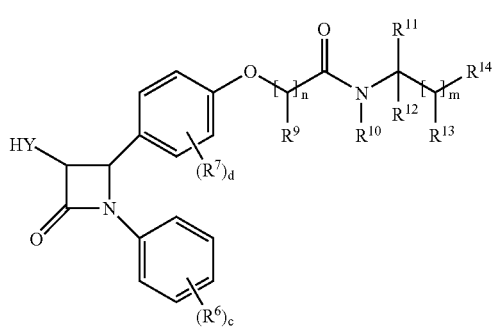

with a compound of formula (XVII):

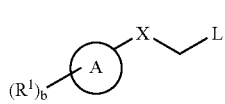

wherein L is a displaceable group;

Process 10): for compounds of formula (I) wherein Y is selected from —O—, —NR$^z$— and —S(O)$_a$— wherein a is 0; reacting a compound of formula (XVIII):

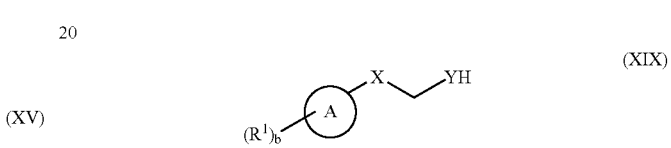

wherein L is a displaceable group; with a compound of formula (XIX):

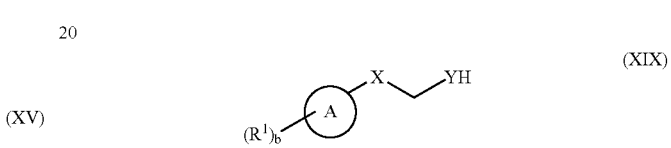

Process 11): for compounds of formula (I) wherein X or Y is —S(O)$_a$— and a is 1 or 2; oxidizing a compound of formula (I) wherein X or Y is —S(O)$_a$— and a is 0 (for compounds of formula (I) wherein and a is 1 or 2) or a is 1 (for compounds of formula (I) wherein and a is 2);

and thereafter if necessary or desirable:
  i) removing any protecting groups;
  ii) forming a pharmaceutically acceptable salt, or a prodrug; or
  iii) separating two or more enantiomers.

19. A pharmaceutical composition which comprises a compound of formula (I), or a pharmaceutically acceptable salt, or a prodrug thereof, as claimed in any one of claims 1-3, in association with a pharmaceutically-acceptable diluent or carrier.

20. A method for producing a cholesterol absorption inhibitory effect in a warm-blooded animal in need of such treatment which comprises administering to said animal an effective amount of a compound of formula (I), or a pharmaceutically acceptable salt, or a prodrug thereof, as claimed in any one of claims 1-3.

21. A method of treating hyperlipidaemic conditions in a warm-blooded animal in need of such treatment which comprises administering to said animal an effective amount of a compound of formula (I), or a pharmaceutically acceptable salt, or a prodrug thereof, as claimed in any one of claims 1-3.

22. A combination of a compound of formula (I), or a pharmaceutically acceptable salt, or a prodrug thereof, as claimed in any one of claims 1-3, and an HMG Co—A reductase inhibitor, or a pharmaceutically acceptable salt, or a prodrug thereof.

23. A combination according to claim 22 wherein the HMG Co—A reductase inhibitors is selected from fluvastatin, lovastatin, pravastatin, simvastatin, atorvastatin, cerivastatin, bervastatin, dalvastatin, pitvastatin, mevastatin and rosuvastatin, or a pharmaceutically acceptable salt, or a prodrug thereof.

24. A pharmaceutical composition which comprises a combination according to claim 22, in association with a pharmaceutically acceptable diluent or carrier.

25. A method for producing a cholesterol absorption inhibitory effect in a warm-blooded animal in need of such treatment which comprises administering to said animal an effective amount of a combination according to claim 22.

26. A method of treating a hyperlipidaemic condition in a warm-blooded animal in need of such treatment which comprises administering to said animal an effective amount of a combination according to claim 22.

27. The method of claim 20 wherein the warm-blooded animal is a human.

28. The method of claim 21 wherein the warm-blooded animal is a human.

29. The method of claim 25 wherein the warm-blooded animal is a human.

30. The method of claim 26 wherein the warm-blooded animal is a human.

31. A method for producing a cholesterol absorption inhibitory effect in a warm-blooded animal in need of such treatment, which method comprises administering to said animal an effective amount of the pharmaceutical composition according to claim 24.

32. The method of claim 31 wherein the warm-blooded animal is a human.

33. A method of treating a hyperlipidaemic condition in a warm-blooded animal in need of such treatment, which method comprises administering to said animal an effective amount of the pharmaceutical composition according to claim 24.

34. The method of claim 33 wherein the warm-blooded animal is a human.

35. A combination of a compound of formula (I), or a pharmaceutically acceptable salt, or a prodrug thereof, as claimed in any one of claims 1-3, and a PPAR alpha and/or gamma agonist, or a pharmaceutically acceptable salt, or a prodrug thereof.

36. A combination according to claim 35 wherein the PPAR alpha and/or gamma agonist is selected from WY-14643, clofibrate, fenofibrate, bezafibrate, GW 9578, pioglitazone, rosiglitazone, eglitazone, proglitazone, BMS 298585, BRL-49634, KRP-297, JTT-501, SB 213068, GW 1929, GW 7845, GW 0207, L-796449, L-165041, and GW 2433, or a pharmaceutically acceptable salt, or a prodrug thereof.

37. A combination according to claim 35 wherein the PPAR alpha and/or gamma agonist is fenofibrate, or a pharmaceutically acceptable salt, or a prodrug thereof.

* * * * *